(12) United States Patent
Collins et al.

(10) Patent No.: US 9,480,696 B2
(45) Date of Patent: Nov. 1, 2016

(54) PROTON-MOTIVE FORCE STIMULATION TO POTENTIATE AMINOGLYCOSIDE ANTIBIOTICS AGAINST PERSISTENT BACTERIA

(75) Inventors: James J. Collins, Newton, MA (US); Kyle R. Allison, Flint, MI (US); Mark P. Brynildsen, Pennington, NJ (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 175 days.

(21) Appl. No.: 14/115,528

(22) PCT Filed: May 4, 2012

(86) PCT No.: PCT/US2012/036492
§ 371 (c)(1),
(2), (4) Date: Feb. 25, 2014

(87) PCT Pub. No.: WO2012/151474
PCT Pub. Date: Nov. 8, 2012

(65) Prior Publication Data
US 2015/0366889 A1 Dec. 24, 2015

Related U.S. Application Data

(60) Provisional application No. 61/482,417, filed on May 4, 2011.

(51) Int. Cl.
| | | |
|---|---|---|
| *A61K 31/70* | (2006.01) | |
| *A61K 31/7004* | (2006.01) | |
| *A61K 31/7036* | (2006.01) | |
| *A61K 45/06* | (2006.01) | |
| *A61K 31/047* | (2006.01) | |

(52) U.S. Cl.
CPC ......... *A61K 31/7036* (2013.01); *A61K 31/047* (2013.01); *A61K 31/7004* (2013.01); *A61K 45/06* (2013.01)

(58) Field of Classification Search
CPC ........... A61K 31/7036; A61K 31/047; A61K 31/7004
See application file for complete search history.

(56) References Cited

U.S. PATENT DOCUMENTS 6,352,978 B1 * 3/2002 Perdiguer ............ A61K 9/0043 424/78.04
7,618,651 B2 * 11/2009 Murthy ................ A61K 31/165 424/488

FOREIGN PATENT DOCUMENTS

CN 101 002 802 7/2007

OTHER PUBLICATIONS

CN 101670094 A, published Mar. 17, 2010, machine translation.*
Song, Hearing Research 94 (1996) 87-93.*
Allison et al., Current Opinion in Microbiology, 14(5):593-598 (2011). "Heterogeneous bacterial persisters and engineering approaches to eliminate them."
Allison et al., Nature, 473(7346):216-221 (2011). "Metabolite-enabled eradication of bacterial persisters by aminoglycosides."
Mates et al., Proceedings of the National Academy of Sciences, 79(21):6693-6697 (1982). "Membrane potential and gentamicin uptake in *Staphylococcus-aureus*."
Nicita et al., Drugs under Experimental and Clinical Research, 7(4):549-554 (1981). "Intra operative antibiotic perfusion in the renal artery in patients with infection induced staghorn calculi."
Taber et al., Microbiological Reviews, 51(4):439-457 (1987). "Bacterial uptake of aminoglycoside antibiotics."
Campbell, B.D. & Kadner, R.J. Relation of aerobiosis and ionic strength to the uptake of dihydrostreptomycin in *Escherichia coli*. Biochim Biophys Acta 593, pp. 1-10, 1980.
Chittapragada M. et al., Aminoglycosides: Molecular Insights on the Recognition of RNA and Aminoglycoside Mimics, Perspectives in Medicinal Chemistry, 3, pp. 21-37, 2009.
Davis, B. D. Mechanism of bactericidal action of aminoglycosides. Microbiol. Rev. 51 , pp. 341-350, 1987.
Kohanski, M. A., Dwyer, D. J., Hayete, B., Lawrence, C. A. & Collins, J. i. A common mechanism of cellular death induced by bactericidal antibiotics. Cell 130, pp. 797-810, 2007.
Magnet, S. & Blanchard, J. S. Molecular insights into aminoglycoside action and resistance. Chem. Rev. 105, pp. 477-497, 2005.
Spoering, A. L. & Lewis, K. Biofilms and planktonic cells of Pseudomonas aeruginosa have similar resistance to killing by antimicrobials. J. Bacteriol. 183, pp. 6746-6751, 2001.
Taber, H. W., Mueller, J. P., Miller, P. F. & Arrow, A. S. Bacterial uptake of aminoglycoside antibiotics. Microbiol. Rev. 51 , pp. 439-457, 1987.
Vakulenko, S. B. & Mobashery, S. Versatility of aminoglycosides and prospects for their future. Clin. Microbiol. Rev. 16, pp. 430-450, 2003.
Walters, M.C., 3rd, Roe, F., Bugnicourt, A., Franklin, M.J. & Stewart, P.S. Contributions of antibiotic penetration, oxygen limitation, and low metabolic activity to tolerance of Pseudomonas aeruginosa biofilms to ciprofloxacin and tobramycin. Antimicrob Agents Chemother 47, pp. 317-323, 2003.
Weisblum, B. & Davies, J. Antibiotic inhibitors of the bacterial ribosome. Bacteriol. Rev. 32, pp. 493-528, 1968.

* cited by examiner

*Primary Examiner* — Layla Berry
(74) *Attorney, Agent, or Firm* — Nixon Peabody LLP; Ronald I. Eisenstein

(57) ABSTRACT

Provided herein are compositions and methods to improve treatment of chronic infections, and reduce, delay, or inhibit formation of biofilms, using specific combinations of aminoglycoside antibiotics and high, localized concentrations of one or more PMF stimulating compounds. These novel methods are easily adapted to clinical settings as toxicity and efficacy of the antibiotics and metabolites used have already been studied in vivo, and as dosing for both the antibiotics and metabolites are known. These approaches and therapeutic methods are also useful with non-metabolic chemicals that induce proton-motive force in bacteria.

48 Claims, 50 Drawing Sheets

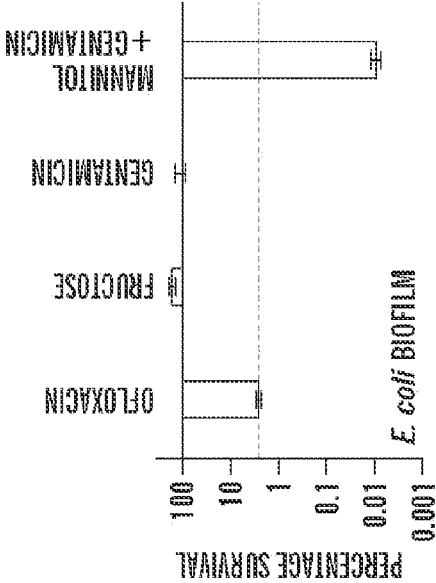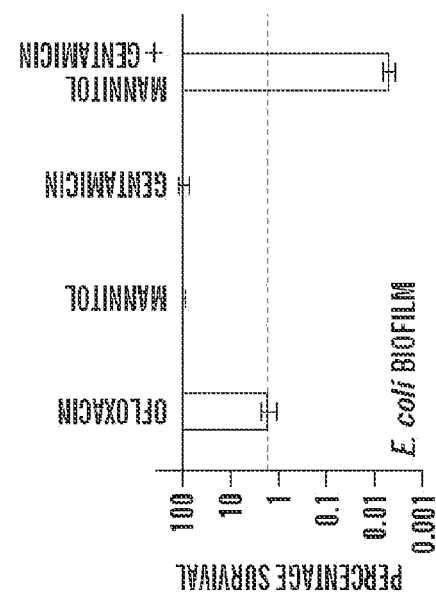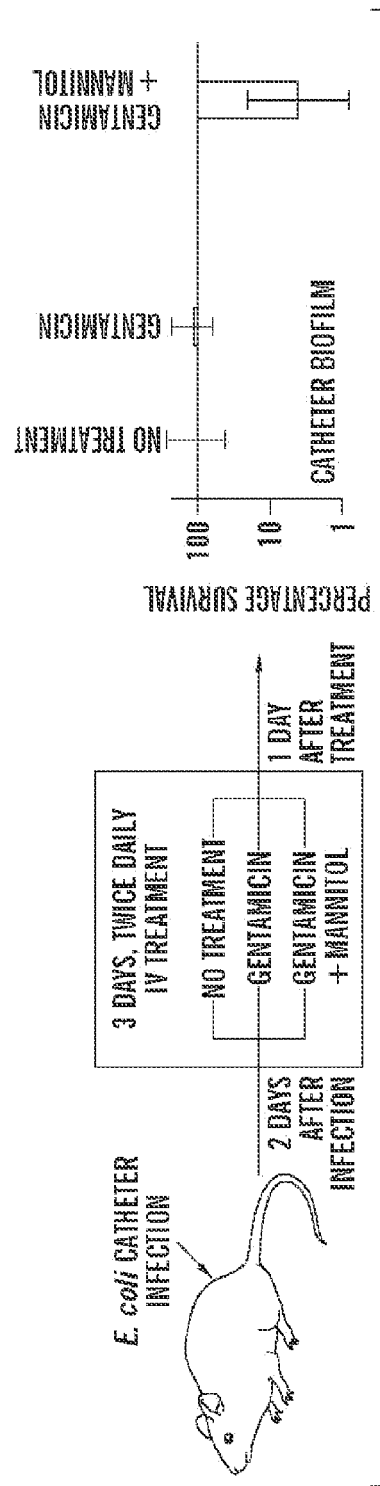
FIG. 3B
FIG. 3C
FIG. 3D

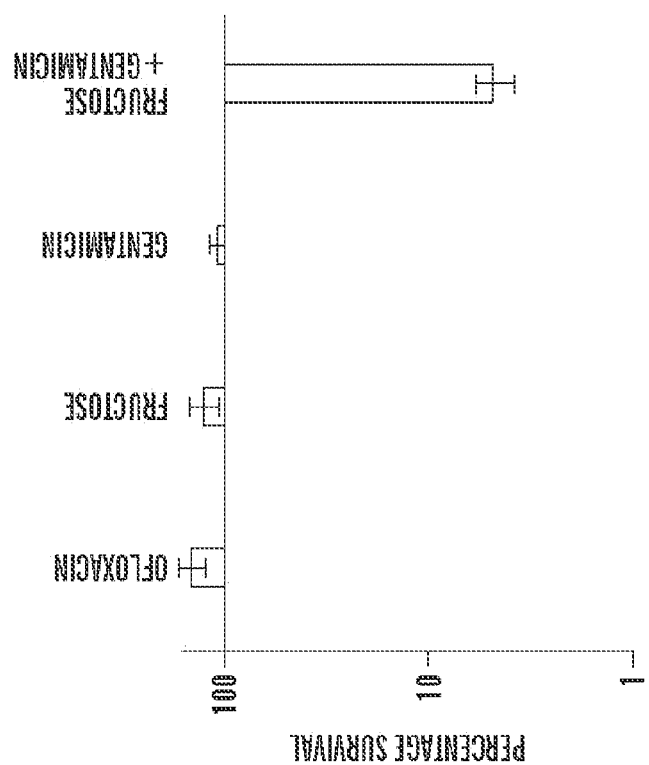
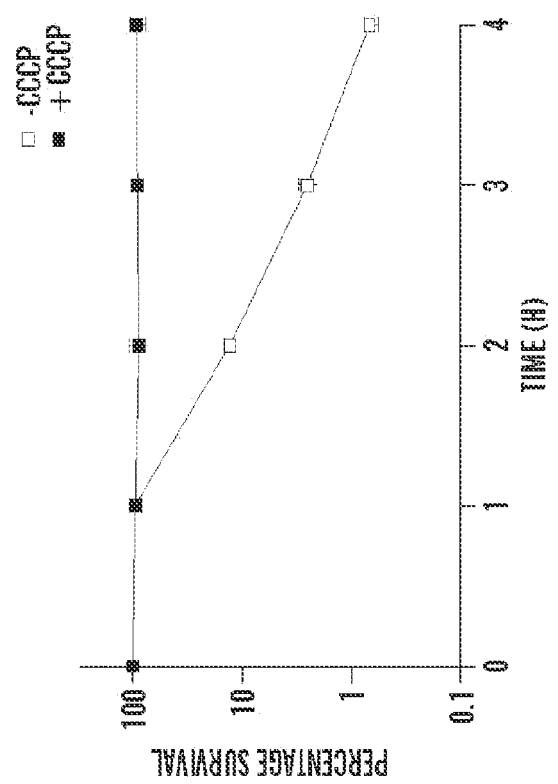
FIG. 4D
FIG. 4C

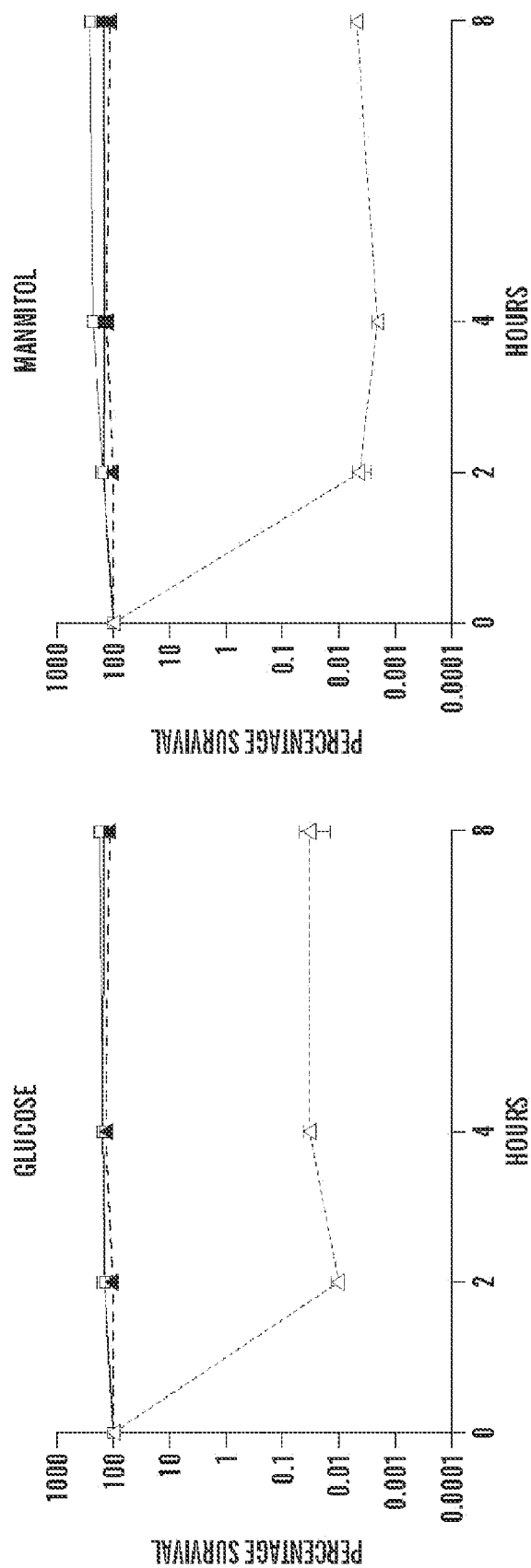

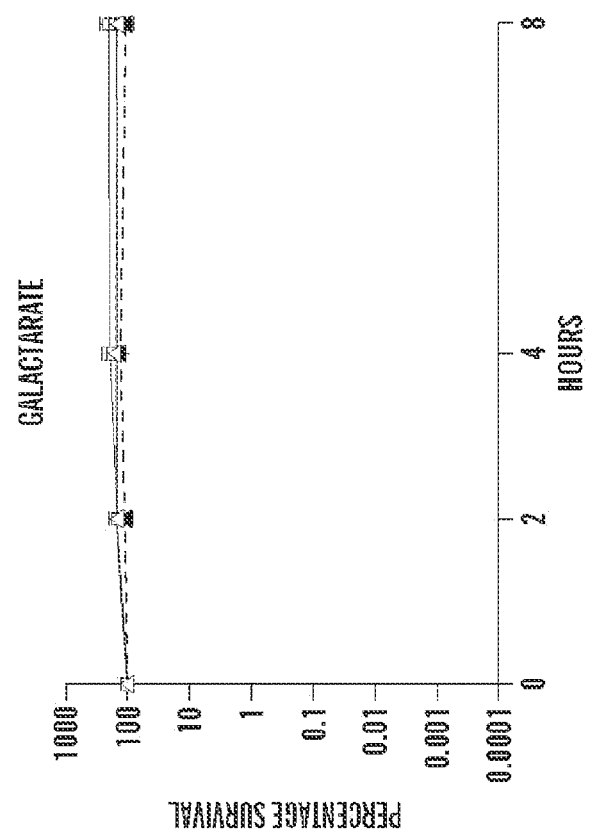
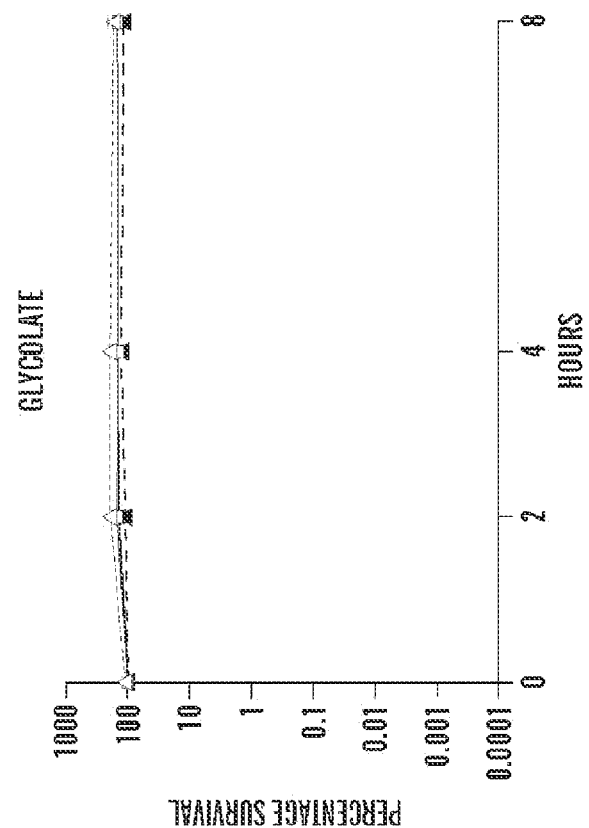

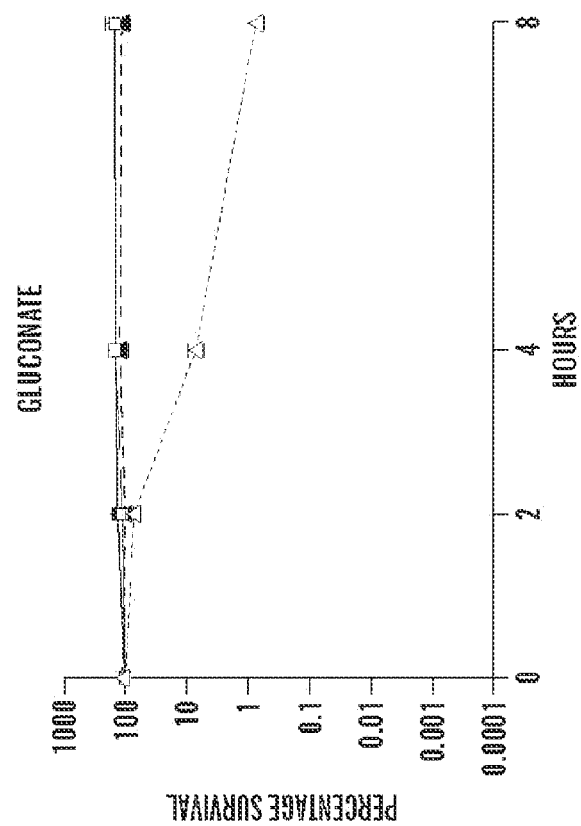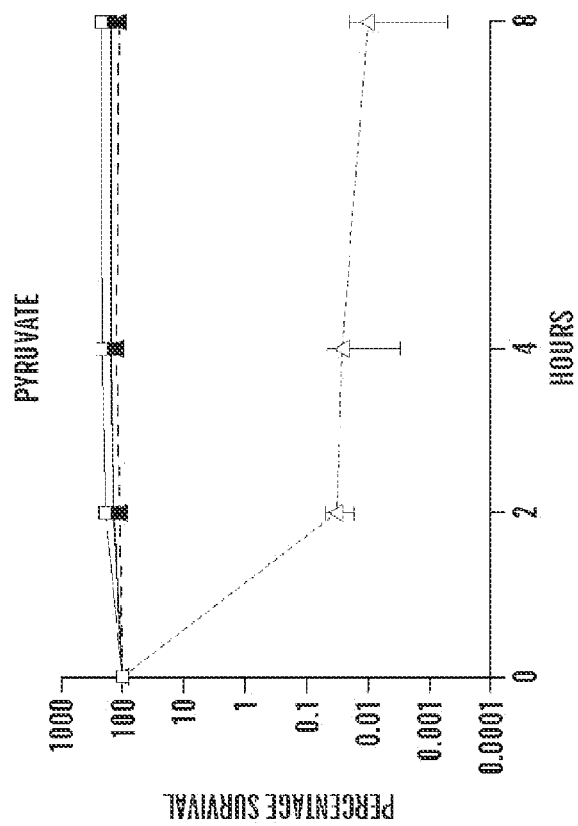
FIG. 7H
FIG. 7G

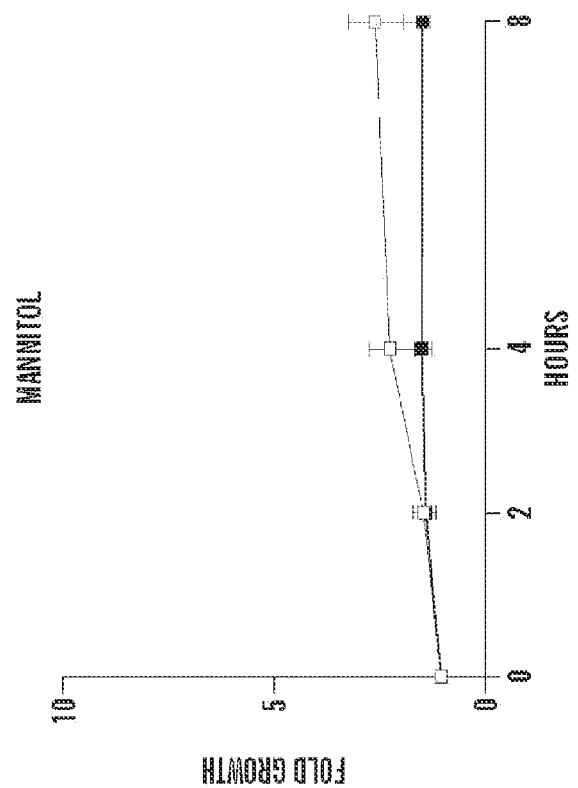
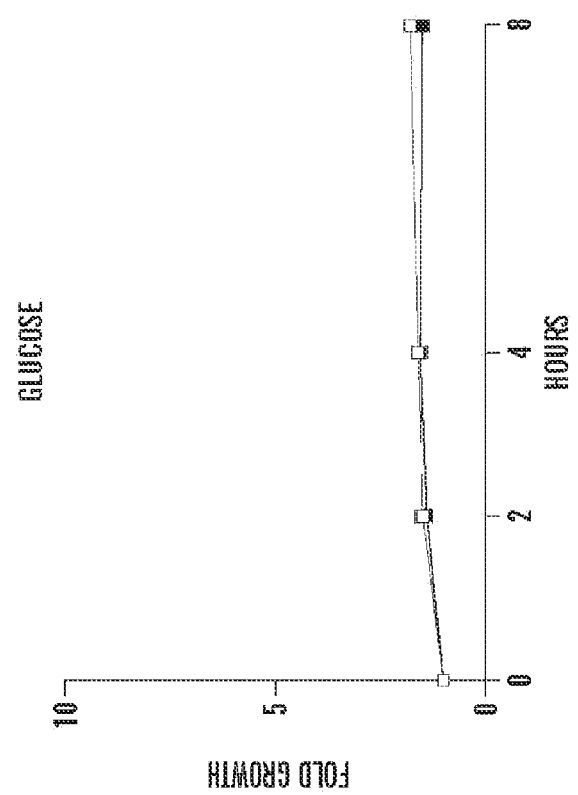
FIG. 8A
FIG. 8B

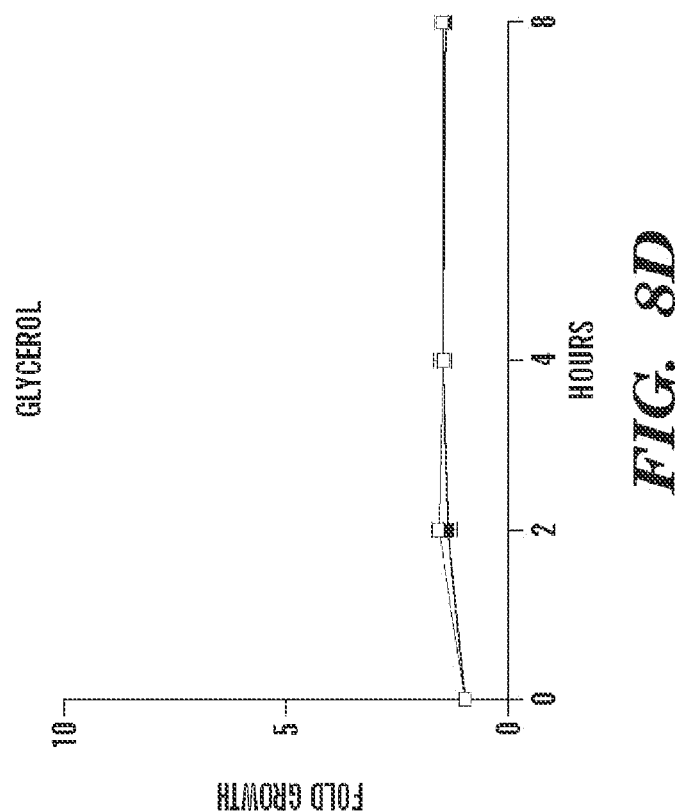
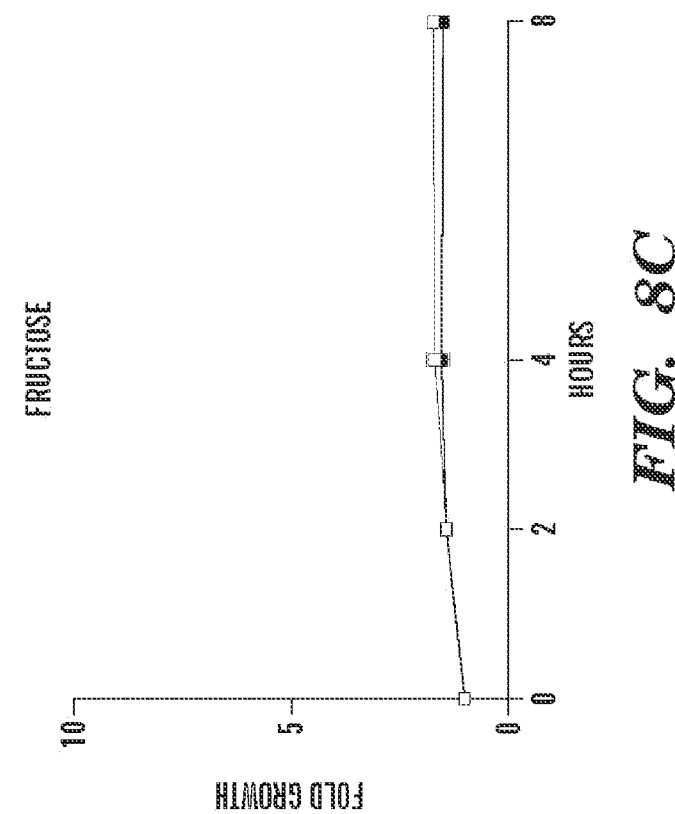

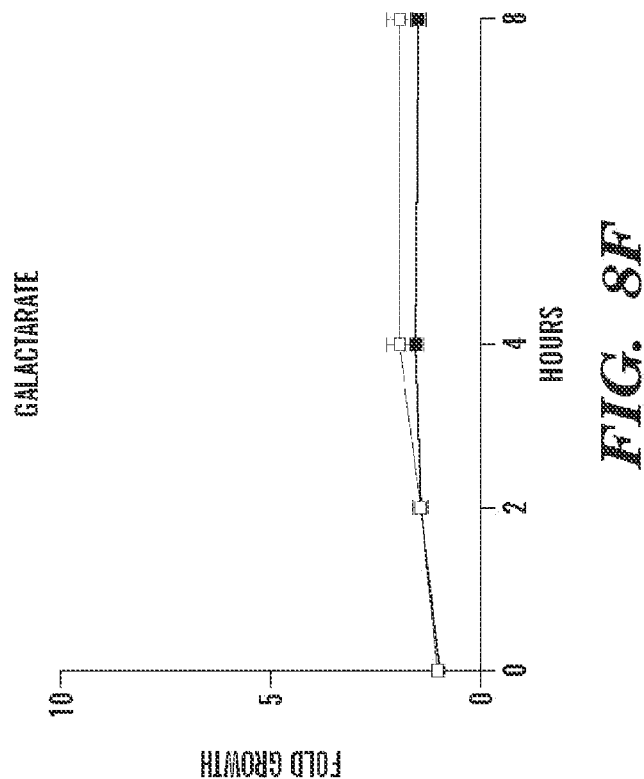
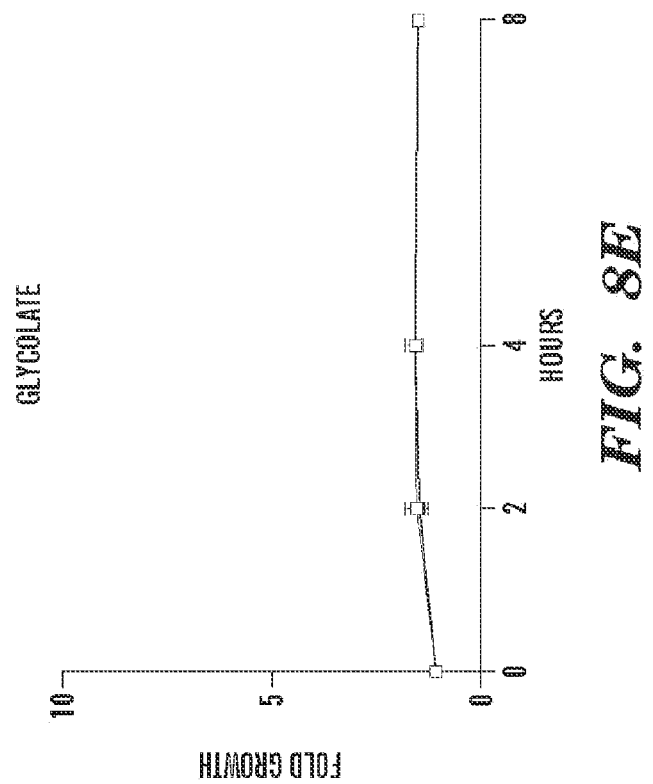

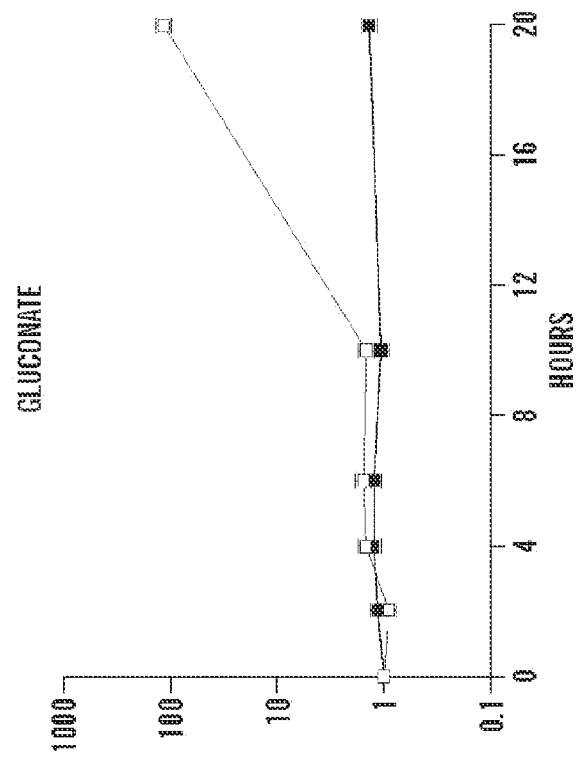
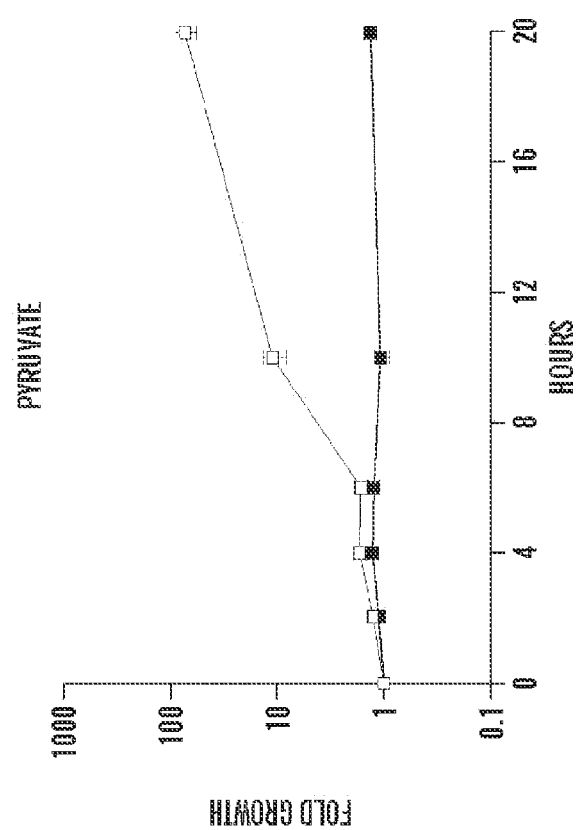
FIG. 9H
FIG. 9G

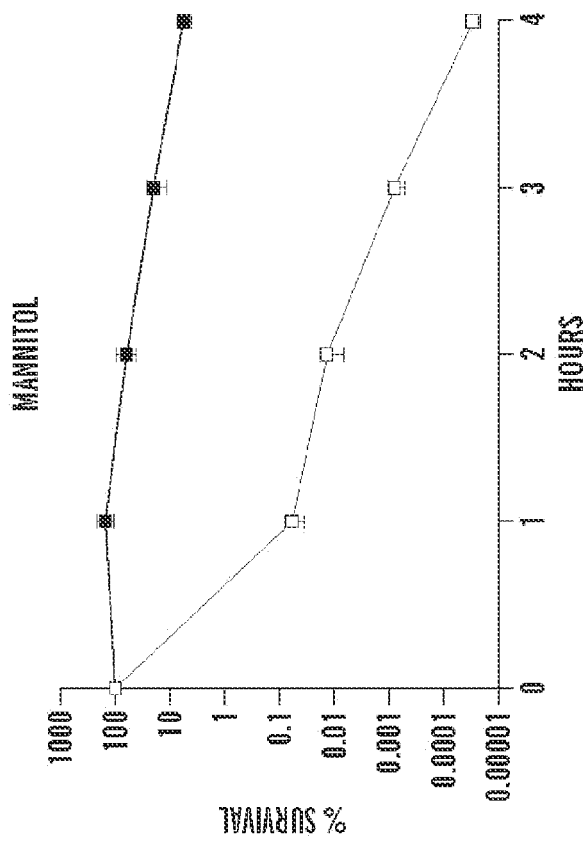
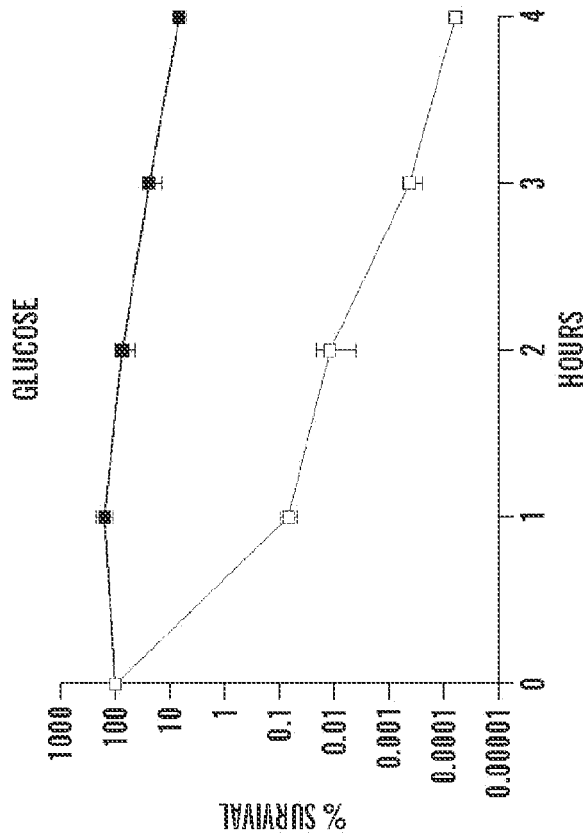
FIG. 13A
FIG. 13B

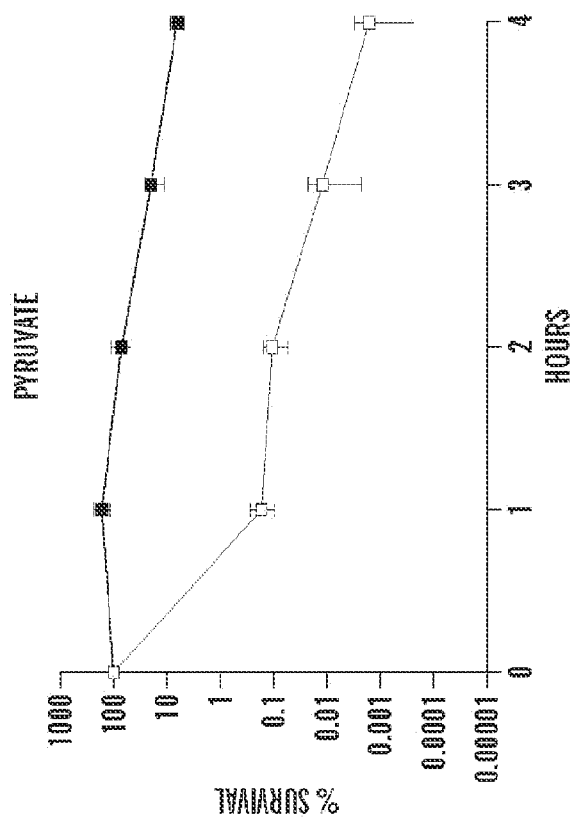
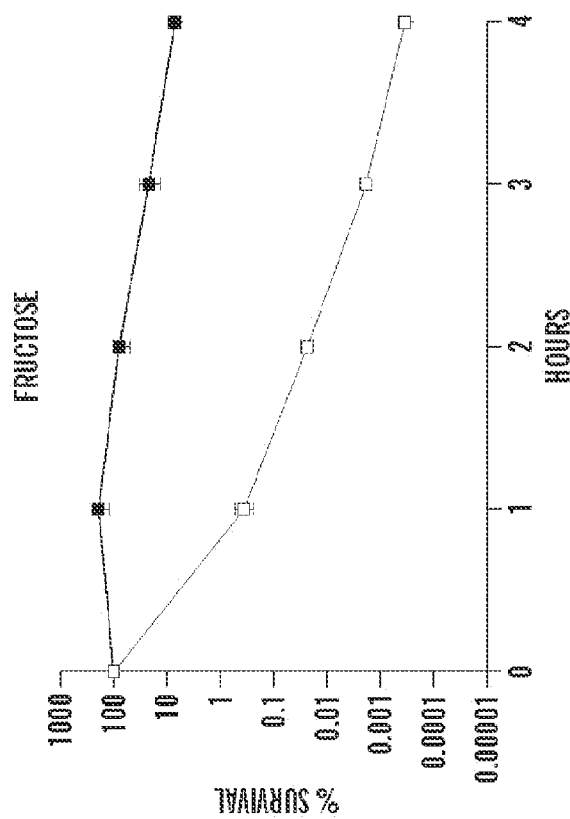
FIG. 13C
FIG. 13D

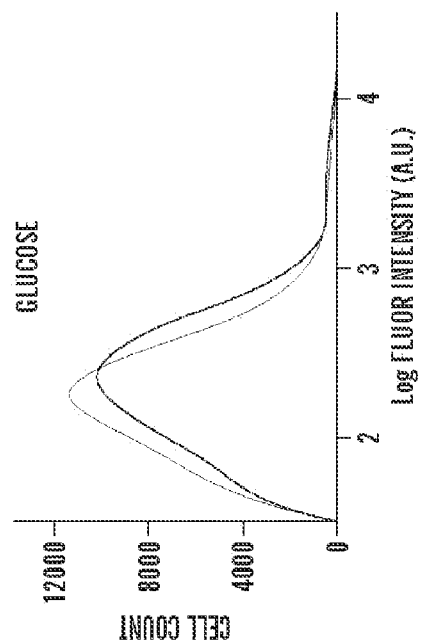
FIG. 15A GLUCOSE
FIG. 15B MANNITOL
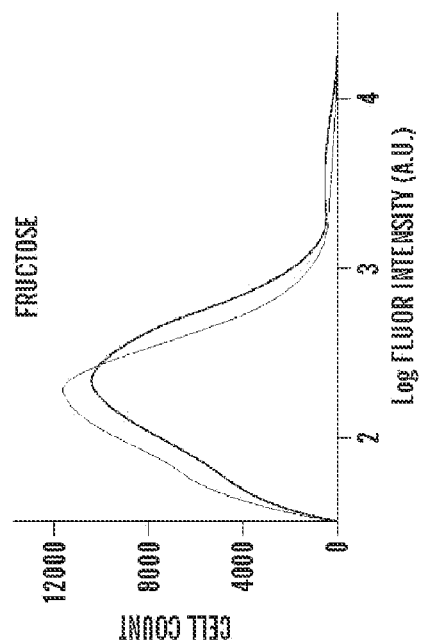
FIG. 15C FRUCTOSE
FIG. 15D GLYCEROL

PROTON-MOTIVE FORCE STIMULATION TO POTENTIATE AMINOGLYCOSIDE ANTIBIOTICS AGAINST PERSISTENT BACTERIA

CROSS-REFERENCE TO RELATED APPLICATIONS

This application is a 35 U.S.C. §371 National Phase Entry Application of International Application No. PCT/US2012/036492, filed May 4, 2012, which designates the United States, and which claims benefit under 35 U.S.C. §119(e) of U.S. Provisional Patent Application Ser. No. 61/482,417 filed May 4, 2011, the contents of each of which are incorporated herein by reference in their entireties.

GOVERNMENT SUPPORT

This invention was made with Government Support under Contract No. OD003644-04 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Nov. 1, 2013, is named 701586-070612_SL and is 7,057 bytes in size.

FIELD OF THE INVENTION

The field of the invention relates to elimination of bacterial persistence and treatment of chronic infections.

BACKGROUND

Bacterial persisters refer to a dormant sub-population of cells tolerant to antibiotic treatment and are considered an important source of chronic and recurrent infection. Bacterial persistence is distinguished from antibiotic resistance by the fact that persisters are not genetically different from antibiotic susceptible cells. Instead, persistence results from phenotypic population heterogeneity within an isogenic population. Viewed as part of an epigenetic survival strategy, persisters forfeit rapid growth in order to gain tolerance to diverse stresses including antibiotics. Genetic studies have uncovered a number of cellular phenomena involved in bacterial persistence, including toxin-antitoxin modules and the stringent response. In addition, glycerol, glyoxylate, and phosphate metabolism have been found to affect persistence, indicating that the cellular metabolic state plays a crucial role in the persister phenotype. Genetic studies have also indicated a role for the DNA damage response in the formation of persisters, indicating that persistence may be, in part, inducible. While these advances have expanded our understanding of persister formation they have not addressed how to eliminate bacterial persisters.

SUMMARY OF THE INVENTION

Bacterial persistence is a state in which a sub-population of dormant cells, termed herein as "bacterial persisters," tolerates antibiotic treatment. Bacterial persisters have been implicated in biofilms and chronic and recurrent infections. Despite this clinical relevance, there are currently no ready means for eradicating persisters. As described herein, the inventors discovered that high, localized concentrations of specific proton-motive force inducing metabolic stimuli (metabolites), such as, for example, those involved in glycolysis, the pentose-phosphate pathway (PPP), or the Enter-Douderoff pathway (EDP), such as, for example, glucose, mannitol, fructose, or pyruvate, permit aminoglycoside killing of both Gram-negative (*Escherichia coli*) and Gram-positive (*Staphylococcus aureus*) persisters. The inventors demonstrate therein that this potentiation is effective in both aerobic and anaerobic conditions and works by facilitating aminoglycoside uptake. Additionally, the inventors demonstrate herein that aminoglycosides in combination with high, localized concentrations of specific metabolites, such as, for example, sugars such as glucose, mannitol, fructose, and pyruvate, can be used to treat *E. coli* and *S. aureus* biofilms. The inventors have established that these approaches can improve in vivo treatment of chronic infections, such as in a mouse urinary tract infection model. The work described herein establishes novel metabolic-based strategies for eradicating bacterial persisters and highlights the critical importance of metabolic environment to antibiotic treatment. The methods described herein take into account the requirement of aminoglycosides uptake on proton-motive force generation, and that metabolites that induce proton-motive force in persistent bacteria induce killing of persisters in an uptake-dependent manner.

Accordingly, in some aspects provided herein are methods for treating a chronic or persisting bacterial infection, the methods comprising administering to a subject having or at risk for a chronic or persisting bacterial infection an effective amount of an aminoglycoside antibiotic and an effective amount of at least one proton motive force (PMF) stimulating compound as an adjuvant. Alo provided herein, in some aspects, are methods for treating a chronic or persisting bacterial infection, comprising: administering to a subject having a chronic or persisting bacterial infection and undergoing treatment with an aminoglycoside antibiotic, an effective amount of at least one proton motive force stimulating compound as an adjuvant.

In some embodiments of these methods and all such methods described herein, the aminoglycoside antibiotic is streptomycin, gentamicin, kanamycin A, or tobramycin.

In some embodiments of these methods and all such methods described herein, the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin.

In some embodiments of these methods and all such methods described herein, the PMF stimulating compound is a compound that enters upper glycolysis in bacteria.

In some embodiments of these methods and all such methods described herein, the PMF stimulating compound is a sugar. In some embodiments, the sugar is glucose, mannitol, fructose, or a combination thereof.

In some embodiments of these methods and all such methods described herein, the PMF stimulating compound is a glycolysis product of a sugar. In some embodiments, the glycolysis product is pyruvate.

In some embodiments of these methods and all such methods described herein, the PMF stimulating compound is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

In some embodiments of these methods and all such methods described herein, the aminoglycoside antibiotic is gentamicin and the at least one PMF stimulating compound is mannitol.

In some embodiments of these methods and all such methods described herein, the aminoglycoside antibiotic is gentamicin and the at least one PMF stimulating compound is fructose.

In some embodiments of these methods and all such methods described herein, the aminoglycoside antibiotic is tobramycin and the at least one PMF stimulating compound is mannitol.

In some embodiments of these methods and all such methods described herein, the bacterial infection comprises one or more gram positive or gram negative organisms. In some embodiments, the bacterial infection comprises one or more of *Escherichia* coli or *Staphylococcus aureus*. In some embodiments, the bacterial infection comprises one or more of species of *Pseudomonas, Proteus, Serratia, Citrobacter, Enterobacter, Klebsiella, Pseudomonas, Acinetobacter*, or *Enterobacter*.

In some embodiments of these methods and all such methods described herein, the bacterial infection is a hospital-acquired infection. In some embodiments, the hospital-acquired infection is caused by methicillin-resistant *Staphylococcus aureus* or multidrug resistant *Pseudomonas aeruginosa*.

In some embodiments of these methods and all such methods described herein, the bacterial infection is characterized by biofilm formation.

In some embodiments of these methods and all such methods described herein, the infection is recurrent.

In some embodiments of these methods and all such methods described herein, the subject having or at risk for a chronic or persisting infection has a urinary tract infection; infective endocarditis; an infection of the skin, nose, ears, and/or eyes; external burns; an infection associated with cystic fibrosis; a prosthetic valve infection; a native valve infection' an infection associated with endometritis; an infections associated with febrile neutropenia; an intraabdominal infections; meningitis; an infections associated with osteomyelitis; an infection associated with pelvic inflammatory disease; an infection associated with peritonitis; an infection associated with pneumonia; an infections associated with pyelonephritis; an infection associated with skin or soft tissue; an infection associated with surgery, or an infection associated with tularemia.

In some embodiments of these methods and all such methods described herein, the subject having or at risk for a chronic or persisting infection is an immunocompromised subject. In some embodiments, the immunocompromised subject is Human Immunodeficiency Virus-positive; a subject with cystic fibrosis; or a subject having chronic obstructive pulmonary disease.

In some embodiments of these methods and all such methods described herein, the subject having or at risk for a chronic or persisting infection has had, is having, or will have an invasive medical procedure.

In some embodiments of these methods and all such methods described herein, the subject having or at risk for a chronic or persisting infection has an in-dwelling medical device.

In some embodiments of these methods and all such methods described herein, the aminoglycoside antibiotic and PMF stimulating compound are administered topically.

In some embodiments of these methods and all such methods described herein, the aminoglycoside antibiotic and PMF stimulating compound are administered intravenously.

In some embodiments of these methods and all such methods described herein, the aminoglycoside antibiotic and PMF stimulating compound are administered intramuscularly.

In some embodiments of these methods and all such methods described herein, the aminoglycoside antibiotic is not administered via oral administration.

Also provided herein, in other aspects, are methods of inhibiting or delaying biofilm formation or colonization on a surface. Such methods comprise contacting a surface with an effective amount of an aminoglycoside antibiotic and an effective amount one or more PMF stimulating compounds.

In some embodiments of these methods and all such methods described herein, the aminoglycoside antibiotic is streptomycin, gentamicin, kanamycin A, or tobramycin.

In some embodiments of these methods and all such methods described herein, the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin.

In some embodiments of these methods and all such methods described herein, the one or more PMF stimulating compounds is a compound that enters upper glycolysis in bacteria.

In some embodiments of these methods and all such methods described herein, the one or more PMF stimulating compounds is a sugar. In some embodiments, the sugar is glucose, mannitol, fructose, or a combination thereof.

In some embodiments of these methods and all such methods described herein, the one or more PMF stimulating compounds is a glycolysis product of a sugar. In some embodiments, the glycolysis product is pyruvate.

In some embodiments of these methods and all such methods described herein, the one or more PMF stimulating compounds is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

In some embodiments of these methods and all such methods described herein, the aminoglycoside antibiotic is gentamicin and the one or more PMF stimulating compounds is mannitol.

In some embodiments of these methods and all such methods described herein, the aminoglycoside antibiotic is gentamicin and the one or more PMF stimulating compounds is fructose.

In some embodiments of these methods and all such methods described herein, the aminoglycoside antibiotic is tobramycin and the one or more PMF stimulating compounds is mannitol.

In some embodiments of these methods and all such methods described herein, the biofilm comprises one or more gram positive or gram negative organisms.

In some embodiments of these methods and all such methods described herein, the surface is a surface of an in-dwelling medical device.

Also provided herein, in some aspects, are uses of an aminoglycoside antibiotic and one or more proton motive force (PMF) stimulating compounds for treating a chronic infection. In some aspects, provided herein are uses of one or more proton motive force (PMF) stimulating compounds for treating a chronic infection in a subject administered an aminoglycoside antibiotic.

In some embodiments of these uses and all such uses described herein, the aminoglycoside antibiotic is streptomycin, gentamicin, kanamycin A, or tobramycin.

In some embodiments of these uses and all such uses described herein, the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin.

In some embodiments of these uses and all such uses described herein, the one or more PMF stimulating compounds is a compound that enters upper glycolysis in bacteria.

In some embodiments of these uses and all such uses described herein, the one or more PMF stimulating compounds is a sugar. In some embodiments of these uses, the sugar is glucose, mannitol, fructose, or a combination thereof.

In some embodiments of these uses and all such uses described herein, the one or more PMF stimulating compounds is a glycolysis product of a sugar. In some embodiments of these uses, the glycolysis product is pyruvate.

In some embodiments of these uses and all such uses described herein, the one or more PMF stimulating compounds is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

In some embodiments of these uses and all such uses described herein, the aminoglycoside antibiotic is gentamicin and the at least one PMF stimulating compound is mannitol.

In some embodiments of these uses and all such uses described herein, the aminoglycoside antibiotic is gentamicin and the at least one PMF stimulating compound is fructose.

In some embodiments of these uses and all such uses described herein, the aminoglycoside antibiotic is tobramycin and the one or more PMF stimulating compounds is mannitol.

In some embodiments of these uses and all such uses described herein, the chronic infection comprises one or more gram positive or gram negative organisms.

In some embodiments of these uses and all such uses described herein, the chronic infection comprises one or more of *Escherichia coli* or *Staphylococcus aureus*. In In some embodiments of these uses, the chronic infection comprises one or more of species of *Pseudomonas, Proteus, Serratia, Citrobacter, Enterobacter, Klebsiella, Pseudomonas, Acinetobacter,* or *Enterobacter.*

In some embodiments of these uses and all such uses described herein, the chronic infection is a hospital-acquired infection. In some embodiments of these uses, the hospital-acquired infection is caused by methicillin-resistant *Staphylococcus aureus* or multidrug resistant *Pseudomonas aeruginosa.*

In some embodiments of these uses and all such uses described herein, the chronic infection is a urinary tract infection; infective endocarditis; an infection of the skin, nose, ears, and/or eyes; external burns; an infection associated with cystic fibrosis; a prosthetic valve infection; a native valve infection' an infection associated with endometritis; an infections associated with febrile neutropenia; an intraabdominal infections; meningitis; an infections associated with osteomyelitis; an infection associated with pelvic inflammatory disease; an infection associated with peritonitis; an infection associated with pneumonia; an infection associated with pyelonephritis; an infection associated with skin or soft tissue; an infection associated with surgery, or an infection associated with tularemia.

In some embodiments of these uses and all such uses described herein, the chronic infection is characterized by biofilm formation.

In some embodiments of these uses and all such uses described herein, the chronic infection is recurrent.

DEFINITIONS

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory-Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed.. John Wiley and Sons, Inc.) and Current Protocols in Immunology (CPI) (John E. Coligan, et. al., ed. John Wiley and Sons, Inc.), which are all incorporated by reference herein in their entireties.

It is understood that the following detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

BRIEF DESCRIPTION OF THE DRAWINGS

FIGS. 3A-3D depict a mechanism for metabolite-enabled eradication of persisters (3A) and clinically relevant experiments (3B-3D). 3A. Metabolite-enabled eradication of persisters proceeds through catabolism of carbon sources, thereby generating NADH, the production of which does not require the PPP, EDP or TCA cycle. The electron transport chain oxidizes NADH and contributes to PMF, which facilitates aminoglycoside uptake and the killing of persisters. The quinones (Q), NADH dehydrogenases (NDH) and central metabolism, including pyruvate (pyr) and acetyl-CoA (A-CoA), are depicted. 3B. Percentage survival of E. coli biofilms after treatment with ofloxacin, mannitol, gentamicin or mannitol plus gentamicin. Because quinolones have high efficacy against Gram-negative biofilms, as compared to other antibiotics[15,20], ofloxacin was used as a benchmark for high biofilm killing. 3C. Percentage survival of E. coli biofilms after treatment with ofloxacin, fructose, gentamicin or fructose plus gentamicin. 3D. Schematic of in vivo experiments in mice (left panel). The right panel shows survival of E. coli biofilms on urinary-tract-inserted catheters after treatment with gentamicin (1 mg kg$^{-1}$) or mannitol (1.5 g kg$^{-1}$) plus gentamicin (1 mg kg$^{-1}$). Means±s.e.m. are presented throughout (n≥3).

FIGS. 4A-4D demonstrate fructose induces PMF-dependent killing of S. aureus persisters by an aminoglycoside. 4A. Percentage survival of, S. aureus persisters after treatment with gentamicin and different metabolites. 4B. Percentage survival of S. aureus persisters after 4-h treatment with fructose and different classes of antibiotics. 4C. Percentage survival of S. aureus persisters after 4-h treatment with gentamicin and fructose, with or without CCCP 4D. Percentage survival of S. aureus biofilms after 4-h treatment with ofloxacin, fructose, gentamicin or fructose plus gentamicin. Means±s.e.m. are presented throughout (n≥3).

FIGS. 8A-8J demonstrate metabolite ability to induce growth in E. coli persisters. Growth data from FIGS. 7A-7J were plotted on a linear scale to show fold growth induced by metabolites. In all plots, black lines indicate no treatment and light lines indicate treatment with carbon source. Plots 8A-8J fold growth data for persisters in M9 plus the following carbon sources: 8A, 10 mM glucose; 8B, 10 mM mannitol; 8C, 10 mM fructose; 8D, 20 mM glycerol; 8E, 30 mM glycolate; 8F, 10 mM galactarate; 8G, 20 mM pyruvate; 8H, 10 mM gluconate; 8I, 12 mM arabinose; and 8J, 12 mM ribose.

FIGS. 9A-9J demonstrate metabolite-induced resuscitation of persisters after 100-fold dilution. Persister cells were incubated for four hours in M9 minimal media plus carbon sources entering metabolism at specific points in glycolysis, the pentose phosphatepathway, and the entner-douderoff pathway. Solid lines indicate growth of persisters on carbon sources. In all plots, solid black lines indicate cell counts of persisters in M9 without carbon source. Plots 9A-9J show growth of persisters in M9 plus the following carbon sources: 9A, 10 mM glucose; 9B, 10 mM mannitol; 9C, 10 mM fructose; 9D, 20 mM glycerol; 9E, 30 mM glycolate; 9F, 10 mM galactarate; 9G, 20 mM pyruvate; 9H, 10 mM gluconate; 9I, 12 mM arabinose; and 9J, 12 mM ribose.

FIGS. 13A-13F demonstrate metabolite-enabled eradication of stationary phase E. coli. Survival of wild-type (EMG2) in stationary phase treated with 10 µg/mL gentamicin with and without carbon source. In all plots, dark lines indicate cultures treated solely with gentamicin and lighter lines indicate cultures treated with gentamicin plus carbon source. Plots 13A-13F show percent survival of persisters in M9 plus the following carbon sources: 13A, 10 mM glucose; 13B, 10 mM mannitol; 13C, 10 mM fructose; 13D, 20 mM pyruvate; 13E, 20 mM glycerol; and 13F, 12 mM arabinose.

FIGS. 15A-15J demonstrate glycolate affects the uptake of Texas Red probe in stationary phase E. coli. Representative histograms of uptake of Texas Red by stationary phase E. coli treated with the following carbon sources: 15A, 10 mM glucose; 15B, 10 mM mannitol; 15C, 10 mM fructose; 15D, 20 mM glycerol; 15E, 30 mM glycolate; 15F, 10 mM galactarate; 15G, 20 mM pyruvate; 15H, 10 mM gluconate; 15I, 12 mM arabinose; and 15J, 12 mM ribose. Light lines indicate samples treated with carbons source and darker lines indicate samples that were not treated with carbon source.

DETAILED DESCRIPTION

Figure 1B:
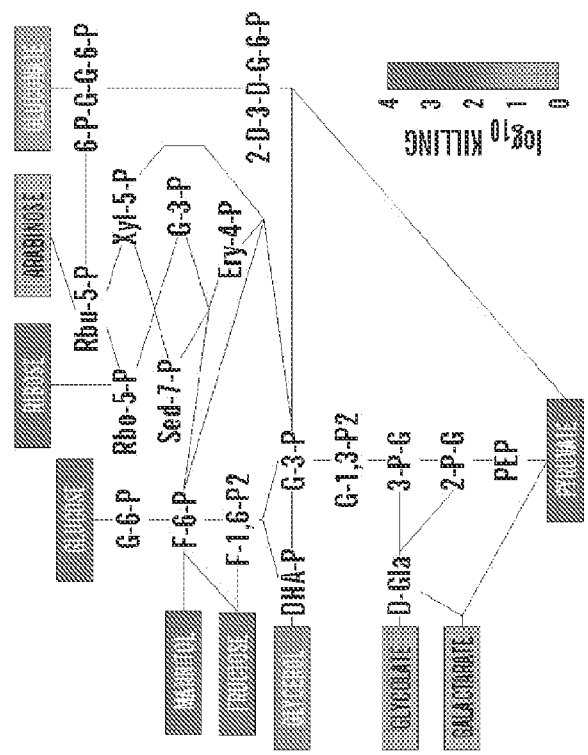
FIGS. 1A-1D demonstrate specific metabolites enable aminoglycoside killing of E. coli bacterial persisters. 1A. Survival of persisters after 2-hour treatment with gentamicin and respective metabolite. 1B. Metabolite-induced persister elimination superimposed on metabolic network. 1C. Survival of bacterial persisters after the following treatments: no treatment, mannitol, gentamicin, gentamicin and mannitol, ofloxacin, ofloxacin and mannitol, ampicllin, or ampicillin and mannitol. 1D. Metabolite-induced Gent-TR uptake by stationary phase cells superimposed on metabolic network (see also FIG. 14). Means±s.e.m. are presented (n≥3).

The compositions, approaches, and methods described herein provide inexpensive and efficient methods to improve treatment of chronic infections, and reduce, delay, or inhibit formation of biofilms. Because many aminoglycosides have increased toxicity at higher doses, the therapeutic compositions and methods described herein comprising proton-motive force stimulating compounds permit lower dosages of aminoglycoside antibiotics to be used with increased efficacy. These novel methods are easily adapted to clinical settings as toxicity and efficacy of the antibiotics and metabolites used have already been studied in vivo, and as dosing for both the antibiotics and metabolites have been established. These approaches and therapeutic methods are also useful with non-metabolic chemicals that induce proton-motive force in bacteria. Additionally, the approaches and methods described herein of inducing proton-motive force can be used to potentiate other classes of antibiotics that also require proton-motive force for uptake.

There are few methods to eliminate persistent bacteria. The antimicrobial field is primarily focused on developing new antibiotics, which is time consuming and costly as it requires the discovery of novel compounds with antibacterial properties, and subsequent in vivo toxicity and efficacy experiments for candidate antibiotics. The approaches and methods described herein improve existing antibiotics, through mechanistic understanding of their activity, and development of PMF stimulating adjuvants or variants thereof, such as, for example, glucose, mannitol, fructose, or pyruvate, that induce proton-motive force.

Accordingly, provided herein are novel combinations of aminoglycosides and adjuvants that stimulate proton-motive force for use in therapeutic compositions and methods, such as intravenous and topical treatment of chronic infections, including for example, biofilm formation during or after surgical interventions. In addition to such therapeutic uses, the combinations of aminoglycosides and PMF stimulating adjuvants described herein are useful for compositions and methods of removing and reducing biofilms and persistent bacteria in non-treatment settings, such as, for example, bacteria-contaminated surfaces and liquids.

Aminoglycosides and Proton-motive Force Stimulating Compounds

Provided herein, in some aspects, are compositions, such as therapeutic compositions, comprising an effective amount of an aminoglycoside antibiotic and an effective amount of one or more PMF stimulating compounds or adjuvants that stimulate proton-motive force.

As used herein, the term "aminoglycoside antibiotic" refers to any naturally occurring drug, or semi-synthetic or synthetic derivative, comprising a highly-conserved aminocyclitol ring (ring II), which is a central scaffold that is linked to various amino-modified sugar moieties, that has antibiotic activity, as the term is defined herein. The ability to inhibit or reduce the growth of, or kill, one or more microorganisms is referred to herein as "antibiotic activity." The aminocyclitol ring is comprised primarily of 2-deoxystreptamine (2-DOS) and has 1,3-diamino functionality and three or four hydroxyl groups that provide anchoring points for aminosugar moieties. Aminoglycosides can be divided into 3 subclasses depending on the substitution pattern: 4-monosubsituted, or 4,5- or 4,6-disubsituted. Aminoglycosides in each subclass show close structural resemblance. Aminoglycosides have several mechanisms of antibiotic activity, including, but not limited to, inhibition of protein synthesis; interfering with proofreading processes during translation, and causing increased rate of error in synthesis with premature termination; inhibition of ribosomal translocation where the peptidyl-tRNA moves from the A-site to the P-site; disruption of bacterial cell membrane integrity; and/or binding to bacterial 30S ribosomal subunit.

Aminoglycosides have antibiotic activity against infections involving aerobic, gram-negative bacteria, such as, for example, *Pseudomonas, Acinetobacter*, and *Enterobacter*. In addition, some Mycobacteria, including the bacteria that cause tuberculosis, are susceptible to aminoglycosides. Aminoglycosides are also useful for empiric therapy for serious infections such as, for example, septicemia, intraabdominal infections, urinary tract infections, and respiratory tract infections, including nosocomial respiratory tract infections. Infections caused by gram-positive bacteria can also be treated with aminoglycosides, in some embodiments of the compositions and methods described herein. Non-limiting examples of aminoglycosides useful in the compositions and methods described herein include streptomycin, gentamicin, kanamycin A, tobramycin, neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, and paromomycinlividomycin, and derivatives thereof of each of these aminoglycoside antibiotics, including synthetic and semi-synthetic derivatives. Chemical structures of three representative classes of exemplary aminoglycoside antibiotics and their substitution sites for use in the methods and compositions described herein are provided below. As understood by one of skill in the art, any compound or derivative having variations of the chemical structures provided below, and having antibiotic activity, are suitable for use in embodiments of the methods and compositions provided herein (see, for example, "Aminoglycosides: Molecular Insights on the Recognition of RNA and Aminoglycoside Mimics," Chittapragada M. et al., Perspectives in Medicinal Chemistry, 2009: 3 21-37, the contents of which are herein incorporated by reference in their entireties).

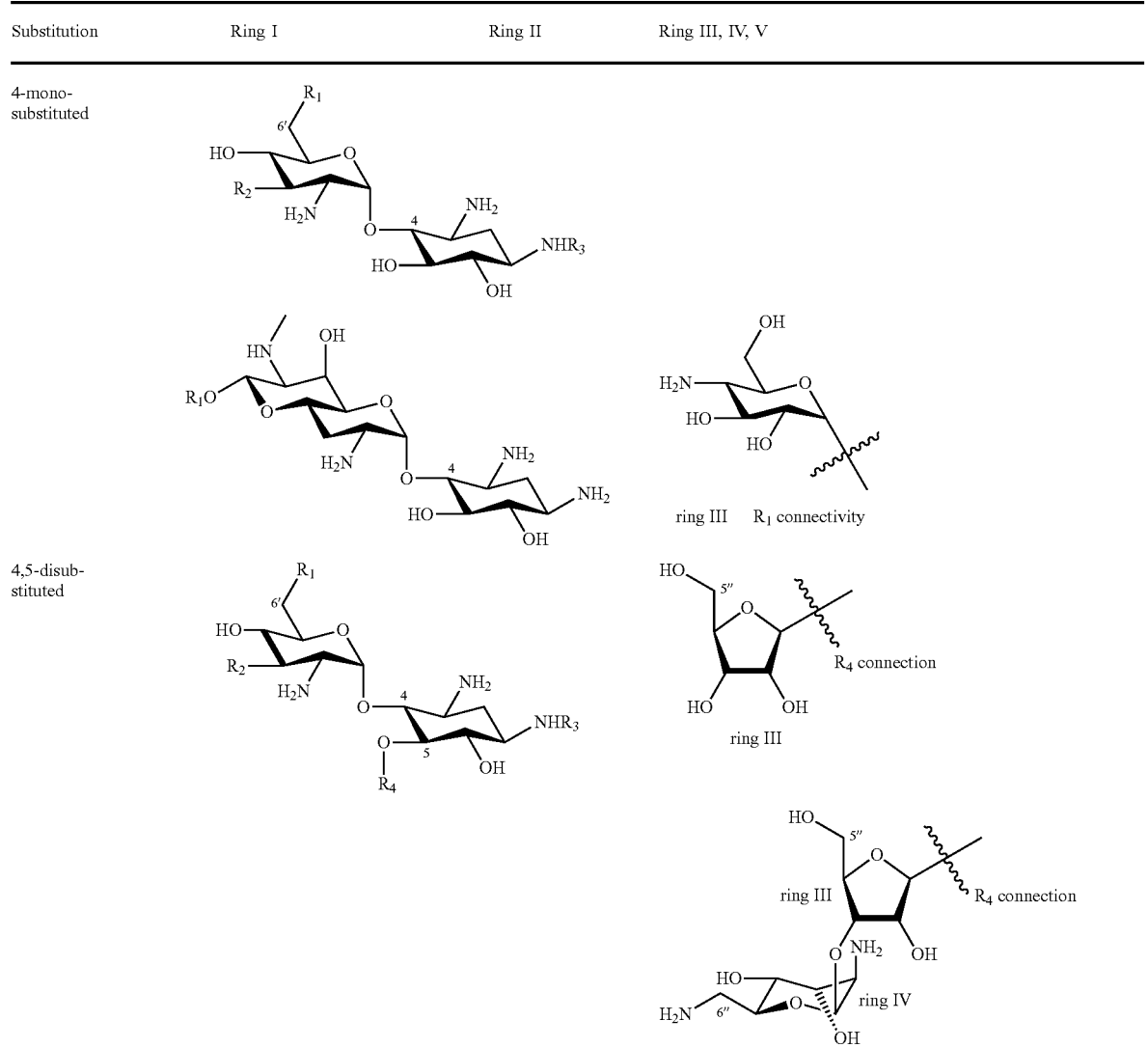

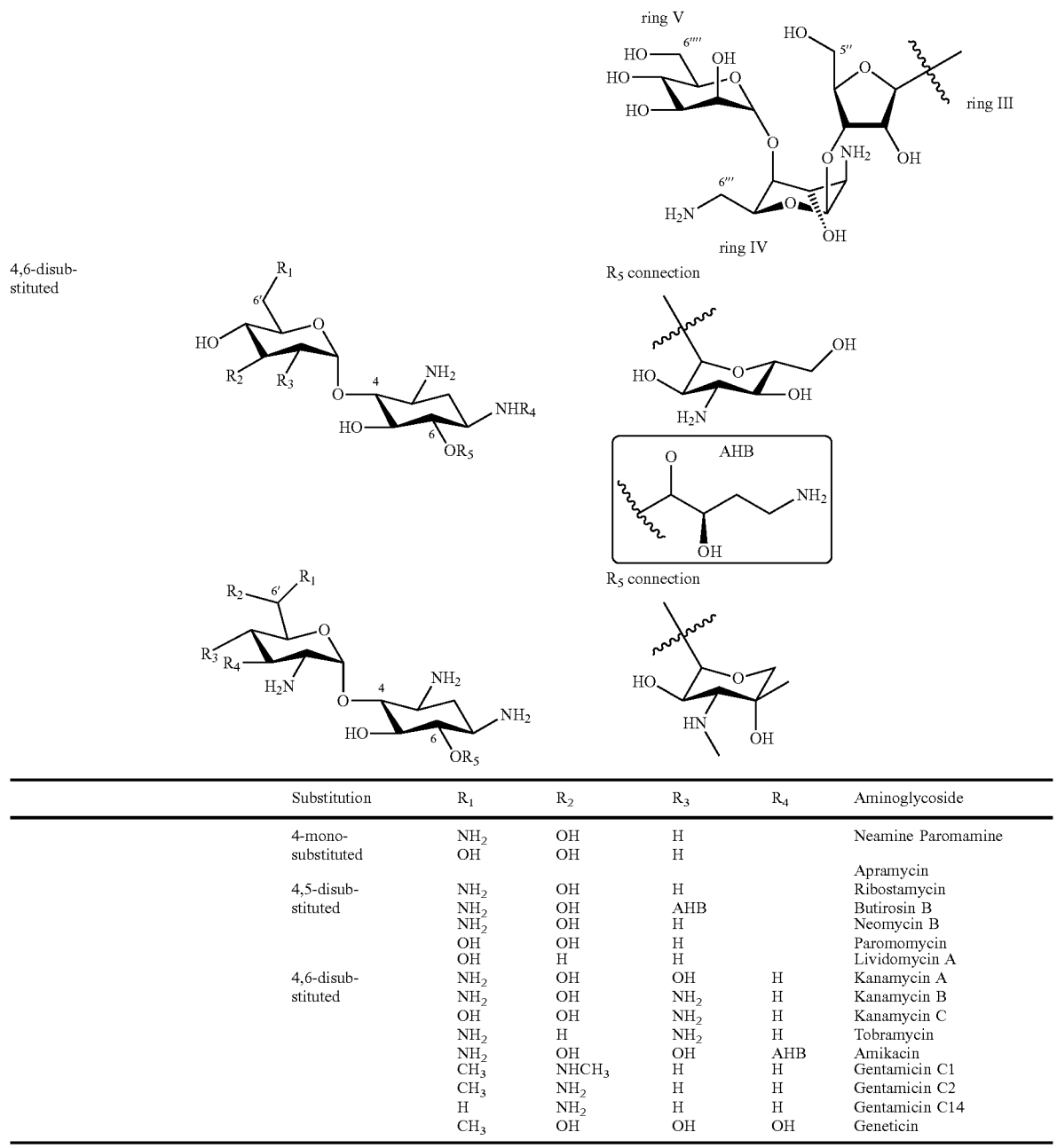

| Substitution | $R_1$ | $R_2$ | $R_3$ | $R_4$ | Aminoglycoside |
| --- | --- | --- | --- | --- | --- |
| 4-mono-substituted | $NH_2$ | OH | H | | Neamine Paromamine |
| | OH | OH | H | | |
| | | | | | Apramycin |
| 4,5-disubstituted | $NH_2$ | OH | H | | Ribostamycin |
| | $NH_2$ | OH | AHB | | Butirosin B |
| | $NH_2$ | OH | H | | Neomycin B |
| | OH | OH | H | | Paromomycin |
| | OH | H | H | | Lividomycin A |
| 4,6-disubstituted | $NH_2$ | OH | OH | H | Kanamycin A |
| | $NH_2$ | OH | $NH_2$ | H | Kanamycin B |
| | OH | OH | $NH_2$ | H | Kanamycin C |
| | $NH_2$ | H | $NH_2$ | H | Tobramycin |
| | $NH_2$ | OH | OH | AHB | Amikacin |
| | $CH_3$ | $NHCH_3$ | H | H | Gentamicin C1 |
| | $CH_3$ | $NH_2$ | H | H | Gentamicin C2 |
| | H | $NH_2$ | H | H | Gentamicin C14 |
| | $CH_3$ | OH | OH | OH | Geneticin |

Accordingly, in some embodiments of the compositions and methods described herein, the aminoglycoside antibiotic is streptomycin. Streptomycin is a protein synthesis inhibitor, and binds to the small 16S rRNA of the 30S subunit of the bacterial ribosome, interfering with the binding of formyl-methionyl-tRNA to the 30S subunit. This leads to codon misreading, eventual inhibition of protein synthesis and ultimately death of microbial cells through mechanisms that are still not understood. Streptomycin is an antibiotic that inhibits both Gram-positive and Gram-negative bacteria, and is therefore a useful broad-spectrum antibiotic. Exemplary chronic infections that can be treated using the compositions and methods described herein comprising streptomycin as the aminoglycoside antibiotic include, but are not limited to, infective endocarditis caused by *enterococcus* when the organism is not sensitive to Gentamicin, tuberculosis in combination with other anti-TB drugs, and plague (*Yersinia pestis*). Streptomycin is also useful in the compositions and methods described herein for use in veterinary medicine applications, such as in treatments against gram negative bacteria in large animals (e.g., horses, cattle, sheep etc.). Streptomycin can also be used, in some embodiments of the compositions and methods described herein, as a pesticide, to combat the growth of bacteria, fungi, and algae. Streptomycin inhibits/reduces bacterial and fungal diseases of certain fruit, vegetables, seed, and ornamental crops, and inhibits/reduces algae in ornamental ponds and aquaria, as well as inhibits/reduces fireblight on apple and pear trees.

In some embodiments of the compositions and methods described herein, the aminoglycoside antibiotic is kanamycin or kanamycin A. Kanamycin interacts with the 30S subunit of prokaryotic ribosomes. Kanamycin A induces substantial amounts of mistranslation and indirectly inhibits translocation during protein synthesis. Kanamycin A is available in oral, intravenous, and intramuscular forms; can be administered via aerosol formulation or irrigation, and can be used to treat a wide variety of infections; and is used in form of the sulfate.

In some embodiments of the compositions and methods described herein, the aminoglycoside antibiotic is gentamicin. Gentamicin is an aminoglycoside antibiotic, used to treat many types of bacterial infections, particularly those caused by Gram-negative organisms. Gentamicin is a bactericidal antibiotic that works, in part, by binding the 30S subunit of the bacterial ribosome, interrupting protein synthesis. Like other aminoglycosides, when gentamicin is given orally, it is not systemically active. This is because it is not absorbed to any appreciable extent from the small intestine. Gentamicin can be administered intravenously, intramuscularly or topically to treat infections, in different embodiments of the methods and compositions described herein. It appears to be completely eliminated unchanged in the urine. Gentamicin is one of the few heat-stable antibiotics that remain active even after autoclaving, which makes it particularly useful in the preparation of some microbiological growth media. It can be used, for example, during orthopedic surgery when high temperatures are required for the setting of cements (e.g. hip replacements). Gentamicin is active against a wide range of human bacterial infections, mostly Gram-negative bacteria including, for example, *Pseudomonas*, *Proteus*, *Serratia*, and the Gram-positive *Staphylococcus* species. Gentamicin is also useful against *Yersinia pestis*, its relatives, and *Francisella tularensis* (the organism responsible for Tularemia seen often in hunters and/or trappers).

In some embodiments of the compositions and methods described herein, the aminoglycoside antibiotic is tobramycin. Tobramycin is an aminoglycoside antibiotic with activity against Gram-positive and Gram-negative bacteria. Tobramycin acts by inhibiting synthesis of protein in bacterial cells. Tobramycin has been shown to be active against most strains of the following organisms both in vitro and in clinical infections: aerobic and facultative Gram-positive microorganisms, including, for example, *Staphylococcus aureus*; aerobic and facultative Gram-negative microorganisms, including, for example, *Citrobacter* sp., *Enterobacter* sp., *Escherichia coli*, *Klebsiella* sp., *Morganella morganii*, *Pseudomonas aeruginosa*, *Proteus mirabilis*, *Proteus vulgaris*, *Providencia* sp., and *Serratia* sp.

In some embodiments of the compositions and methods described herein, the aminoglycoside antibiotic is netilmicin. Netilmicin is not absorbed from the gut and can therefore be given by injection or infusion. It can be used in the treatment of serious infections particularly those resistant to gentamicin.

In some embodiments of the compositions and methods described herein, the aminoglycoside antibiotic is Sisomicin (BACTOCEAZE or ENSAMYCIN), isolated from fermentation broth of a species of the genus *Micromonospora*. It is a newer broad-spectrum aminoglycoside, most structurally related to gentamicin. Sisomicin is a predictably active aminoglycoside against gram-positive bacteria. Like other aminoglycosides, Sisomicin is bactericidal for sensitive clinical isolates. The Minimum Bactericidal Concentrations (MBC) for Sisomicin have been found to be equivalent or very close to the Minimum Inhibitory Concentrations (MIC). Most clinical isolates of *Pseudomonas aeruginosa* remain susceptible to sisomicin.

In some embodiments of the compositions and methods described herein, the aminoglycoside antibiotic is arbekacin, a semisynthetic aminoglycoside antibiotic. It is primarily used for the treatment of infections caused by multi-resistant bacteria including methicillin-resistant *Staphylococcus aureus* (MRSA). Arbekacin was originally synthesized from dibekacin in 1973. It has been registered and marketed in Japan since 1990 under the trade name HABEKACIN. Generic versions of the drug are also available under such trade names as DECONTASIN and BLUBATOSINE. Arbekacin is used for the short term treatment of multi-resistant bacterial infections, such as, for example, methicillin-resistant *Staphylococcus aureus* (MRSA), as well as enteric bacteria and other eubacteria. Arbekacin works by binding to the bacterial 30S ribosomal subunit, causing misreading of t-RNA which consequently, leaves the bacterium unable to synthesize proteins vital to its growth. Specifically, arbekacin binds to four nucleotides of 16S rRNA and a single amino acid of protein S12. This interferes with decoding site in the vicinity of nucleotide 1400 in 16S rRNA of 30S subunit. This region interacts with the wobble base in the anticodon of tRNA. This leads to misreading of mRNA so incorrect amino acids are inserted into the polypeptide leading to nonfunctional or toxic peptides and the breakup of polysomes into nonfunctional monosomes. Arbekacin, like other aminoglycosides, is not well absorbed from the gastrointestinal tract. Its absorption is markedly improved by parenteral administration. Normal duration of IM or IV arbekacin aminoglycoside antibiotic therapy is 7-10 days, although a longer duration may be necessary in some cases.

In some embodiments of the compositions and methods described herein, the aminoglycoside antibiotic is amikacin, an aminoglycoside antibiotic used to treat different types of bacterial infections. Amikacin works by binding to the bacterial 30S ribosomal subunit, causing misreading of mRNA and leaving the bacterium unable to synthesize proteins vital to its growth. Amikacin is often used for Gram negative bacteria such as *Pseudomonas aeruginosa*, *Acinetobacter*, and *Enterobacter*, including, for example, treating severe, hospital-acquired infections with multidrug resistant *Pseudomonas aeruginosa*, *Acinetobacter*, and *Enterobacter, Serratia marcescens* and *Providencia stuartii* are also included in the spectrum. Amikacin can also be used to treat non tubercular mycobacterial infections and tuberculosis, when first line drugs fail to control the infection. Amikacin can be combined, in some embodiments, with a beta-lactam antibiotic for empiric therapy for people with neutropenia and fever. In some embodiments of the methods and compositions described herein, amikacin can be combined or administered with fosfomycin (also known as phosphomycin, phosphonomycin and the trade names MONUROL and MONURIL), for treatment of certain infections, such as for example, urinary tract infection.

In some embodiments of the compositions and methods described herein, the aminoglycoside antibiotic is neomycin. Neomycin is overwhelmingly used as a topical preparation, such as NEOSPORIN. It can also, in some embodiments, be administered orally. Neomycin is not absorbed from the gastrointestinal tract and has been used as a preventive measure for hepatic encephalopathy and hypercholesterolemia. By killing bacteria in the intestinal tract, it keeps ammonia levels low and prevents hepatic encephalopathy, especially prior to GI surgery. It has also been used to treat small intestinal bacterial overgrowth. Similar to other aminoglycosides, neomycin has excellent activity against Gram-negative bacteria, and has partial activity against Gram-positive bacteria. It is not given intravenously, as neomycin is extremely nephrotoxic (causes kidney damage), especially compared to other aminoglycosides. The exception is when neomycin is included, in very small quantities, as a preservative in some vaccines—typically 0.025 mg per dose.

In some embodiments of the compositions and methods described herein, the aminoglycoside antibiotic is framycetin. Framycetin is commonly sold as SOFRAMYCIN and SOFRA-TULLE. It also exists in veterinary products, as Framycetin sulf. Like neomycin, framycetin has poor systemic absorption. It can be used in topical preparations for infections of the skin, nose, ears, and eyes, for example, in combination with other antibacterial drugs and corticosteroids, in some embodiments. It can also be used for gastrointestinal infections, in some embodiments.

In some embodiments of the compositions and methods described herein, the aminoglycoside antibiotic is paromomycin (brand name HUMATIN), first isolated from *Streptomyces krestomuceticus* in the 1950s. It is also called monomycin and aminosidine. Paromomycin is an antibiotic designed to fight intestinal infections such as cryptosporidiosis, amoebiasis, and leishmaniasis. The route of administration of paromomycin can be intramuscular injection and capsule, in some embodiments.

Provided herein in some embodiments, are combinations of aminoglycoside antibiotics and other antibiotics for potentiation by one or more PMF-stimulating compounds. As used herein, the term "antibiotic" refers to any compound known to one of ordinary skill in the art that will inhibit or reduce the growth of, or kill, one or more microorganisms, including bacterial species and fungal species. Many antibacterial compounds are relatively small molecules with a molecular weight of less than 2000 atomic mass units. The term "antibiotic" includes semi-synthetic modifications of various natural compounds, such as, for example, the beta-lactam antibiotics, which include penicillins (produced by fungi in the genus *Penicillium*), the cephalosporins, and the carbapenems. Accordingly, the term "antibiotic" includes, but is not limited to, aminoglycosides (e.g., gentamicin, streptomycin, kanamycin), β-lactams (e.g., penicillins and cephalosporins), vancomycins, bacitracins, macrolides (e.g., erythromycins), lincosamides (e.g., clindomycin), chloramphenicols, tetracyclines, amphotericins, cefazolins, clindamycins, mupirocins, sulfonamides and trimethoprim, rifampicins, metronidazoles, quinolones, novobiocins, polymixins, gramicidins, or any salts or variants thereof. The antibiotic used in addition to the aminoglycoside antibiotic various embodiments of the therapeutic compositions and methods described herein will depend on the type of bacterial infection.

As demonstrated herein, the inventors have discovered that compounds that stimulate proton-motive force, such as high concentrations (e.g., at least 5 mM or greater, at least 6 mM or greater, at least 7 mM or greater, at least 8 mM or greater, at least 9 mM or greater; at least 10 mM or greater, at least 11 mM or greater, at least 12 mM or greater, at least 13 mM or greater, at least 14 mM or greater; at least 15 mM or greater, at least 16 mM or greater, at least 17 mM or greater, at least 18 mM or greater, at least 19 mM or greater; at least 20 mM or greater, at least 25 mM or greater, at least 50 mM or greater, at least 100 mM or greater, at least 500 mM or greater, or more, or all ranges or amounts in-between) of certain metabolites, unexpectedly enhance the efficacy of known aminoglycoside antibiotics, thereby providing novel combinatorial thereof compositions and methods for treating chronic or persistent bacterial infections. The methods and compositions described herein are formulated to ensure that an effective amount of a proton-motive force (PMF) stimulating compound reaches the site of infection, thus overcoming, for example, the known significantly decreased amounts of blood glucose normally found at the site of an infection. Accordingly, the compositions and methods described herein comprise an effective amount of one or more proton-motive force (PMF) stimulating compounds or adjuvants, in addition to the aminoglycoside antibiotic.

The phrases "proton-motive force (PMF) stimulating compound," "proton-motive force (PMF) stimulating adjuvant," or "adjuvant that stimulates proton-motive force (PMF)," as used herein, refer to an agent or compound, including a metabolite, that causes or facilitates a qualitative or quantitative increase in or stimulates proton gradients used to generate chemiosmotic potential energy in cells known as a "proton motive force," where the potential energy is used for the synthesis of ATP by oxidative phosphorylation. By increasing proton-motive force in persister bacteria, the inventors have discovered that this increases or potentiates aminoglycoside antibiotic uptake and killing of bacteria via catabolism of carbon sources and increased oxidation of NADH.

Accordingly, a proton-motive force (PMF) stimulating compound or adjuvant can increase or stimulate PMF in a cell, such as a bacterial cell, by about at least 10% or more, at least 20% or more, at least 30% or more, at least 40% or more, at least 50% or more, at least 60% or more, at least 70% or more, at least 80% or more, at least 90% or more, at least 95% or more, at least 100%, at least 2-fold greater, at least 5-fold greater, at least 10-fold greater, at least 25-fold greater, at least 50-fold greater, at least 100-fold greater, at least 1000-fold greater, and all amounts in-between, in comparison to a reference or control PMF level in the absence of the proton-motive force (PMF) stimulating compound, or in the presence of the aminoglycoside antibiotic alone. Methods and assays to identify such PMF stimulating compounds can be based on any method known to one of skill in the art, are found throughout the specification, in the drawings, and in the Example section, such as the metabolite potentiation assays described at FIGS. 1A-1D, 7A-7J, 8A-8J, and 9A-9J, for example.

As used herein, the term "adjuvant" refers to an agent which enhances the pharmaceutical effect of another agent, such as an aminoglycoside antibiotic. The PMF stimulating compounds as disclosed herein function as adjuvants to the aminoglycoside antibiotics, by enhancing the effect of the aminoglycoside antibiotics by about at least 10% or more, at least 20% or more, at least 30% or more, at least 40% or more, at least 50% or more, at least 60% or more, at least 70% or more, at least 80% or more, at least 90% or more, at least 95% or more, at least 100%, at least 2-fold greater, at least 5-fold greater, at least 10-fold greater, at least 25-fold greater, at least 50-fold greater, at least 100-fold greater, at least 1000-fold greater and all amounts in-between as compared to use of the aminoglycoside antibiotic alone.

The term "agent" as used herein in reference to a PMF stimulating compound means any compound or substance such as, but not limited to, a small molecule, nucleic acid, polypeptide, peptide, drug, ion, etc. An "agent" can be any chemical, entity, or moiety, including, without limitation, synthetic and naturally-occurring proteinaceous and non-proteinaceous entities. In some embodiments, an agent is a nucleic acid, a nucleic acid analogue, a protein, an antibody, a peptide, an aptamer, an oligomer of nucleic acids, an amino acid, or a carbohydrate, and includes, without limitation, proteins, oligonucleotides, ribozymes, DNAzymes, glycoproteins, siRNAs, lipoproteins, aptamers, and modifications and combinations thereof etc. In certain embodiments, as described herein, agents are metabolites. Compounds can be known to have a desired activity and/or property, e.g., potentiate aminoglycoside activity, or can be selected from a library of diverse compounds, using screening methods known to one of ordinary skill in the art.

As used herein, the term "small molecule" refers to a chemical agent which can include, but is not limited to, a peptide, a peptidomimetic, an amino acid, an amino acid analog, a polynucleotide, a polynucleotide analog, an aptamer, a nucleotide, a nucleotide analog, an organic or inorganic compound (e.g., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Accordingly, in some embodiments of the compositions and methods described herein, the proton-motive force (PMF) stimulating compound is a metabolite or a metabolic stimuli, such as, for example, a compound or a variant thereof that enters upper glycolysis in bacteria. Exemplary metabolites for use as proton-motive force (PMF) stimulating compounds in some embodiments of the compositions and methods described herein include, but are not limited to, sugarsand their analogs, such as, glucose, mannitol, and fructose, and analogs thereof, and their metabolites, such as the glycolysis product pyruvate. In some embodiments, metabolites for use as proton-motive force (PMF) stimulating compounds in the compositions and methods described herein include, but are not limited to, lactate, glucosamine, sorbitol, n-acetyl glucosamine, n-acetyl muramic acid, maltose, galactosamine, trehaloseribose, arabinose, gluconate, glycerol, galactarate, and analogs or derivatives thereof. The inventors have discovered high concentrations of metabolites and metabolic stimuli, preferably localized at the site of an infection, result in increased PMF and potentiation of aminoglycoside antibiotic uptake. Accordingly, in some embodiments of the methods and compositions described herein, the effective concentration of a proton-motive force (PMF) stimulating compound being used is at least 2.5 mM, at least 5 mM or greater, at least 6 mM or greater, at least 7 mM or greater, at least 8 mM or greater, at least 9 mM or greater; at least 10 mM or greater, at least 11 mM or greater, at least 12 mM or greater, at least 13 mM or greater, at least 14 mM or greater; at least 15 mM or greater, at least 16 mM or greater, at least 17 mM or greater, at least 18 mM or greater, at least 19 mM or greater; at least 20 mM or greater, at least 25 mM or greater, at least 50 mM or greater, at least 100 mM or greater, at least 500 mM or greater, or more, or all ranges or amounts in-between.

Glucose analogs that can be used in some embodiments of the methods and compositions described herein are known in the art and include, but are not limited to, glucose derivatives such as D-(+)-2-deoxyglucose, D-(+)-2-amino-2-deoxy-glucose or N-acetyl D-(+)-2-amino-2-deoxyglucose; D-mannose and mannose derivatives; D-glucose and D-glucose derivatives, including but not limited to D-3-amino-3-deoxy-glucose and D-2-amino-2-deoxy-glucose; and D-galactose and galactose derivatives including but not limited to D-2-deoxy-D-galasctose, D-4-amino-4-deoxy-galactose and D-2-amino-2-deoxy-galactose. The glucose or glucose moiety thus can differ from D-glucose or a derivative such as 2-DG and 2-glucosamine in that it is an epimer thereof. In addition, the glucose or glucose analog moiety can be a fluorinated derivative of any of the foregoing compounds. Moreover, the oxygen in the ring of any of the foregoing compounds can be substituted with an isostere selected from the group consisting of S, sulfone, and the like. For example, the glucose analog can be 5-thio-D-glucose or a derivative thereof. The term "glucose analog" also includes glucose derivatives, including, but not limited to, derivatives having (C1-C12)acyl groups or (C1-C12)akyl groups attached via —O— or —NH— groups at the 3- and 4-positions of the glucose molecules. Additionally, the glucose derivative may have a solubility or partitioning effector or component attached at the 1-, 3-, or 4-positions.

The type of bacterial infection being treated can be used to determine, in some embodiments, what particular combination of aminoglycoside antibiotic and one or more PMF stimulating compounds to be given or administered to a subject, using the methods and compositions described herein. For example, in some embodiments of the compositions and methods described herein, the aminoglycoside antibiotic is gentamicin and the proton-motive force (PMF) stimulating compound is mannitol. In some embodiments of the compositions and methods described herein, the aminoglycoside antibiotic is gentamicin and the proton-motive force (PMF) stimulating compound is fructose. In some embodiments of the compositions and methods described herein, when the infection is caused by a Staphyloccocus species, for example, the proton-motive force (PMF) stimulating compound preferably used is fructose.

Chronic or Persisting Infections and Methods of Treatment or Inhibition Thereof

As demonstrated herein, administration of an effective amount of an aminoglycoside antibiotic and an effective amount one or more PMF stimulating compounds can be used in methods of treatment of chronic or persistent bacterial infections. Infections in which bacteria are either slow-growing, persistent, or in a biofilm pose a serious clinical challenge for therapy because cells in these states exhibit tolerance to the activity of antimicrobial agents, such as antibiotics. Osteomyelitis, infective endocarditis, chronic wounds, infections related to in-dwelling devices, infections resulting from second- and third-degree burns, and bacterial infections that are secondary complications of respiratory or mucosal conditions, such as those arising from cystic fibrosis, sinusistis, and viral infections, are non-limiting examples of infections that harbor persistent bacterial cells. Because most antimicrobial agents exert maximal activity against rapidly dividing cells, antimicrobial therapies for these infections are not optimal, requiring protracted treatment times, high and sometimes toxic antibiotic doses, and demonstrating higher failure rates. In contrast, the novel methods and compositions described herein, which combine an effective amount of an aminoglycoside antibiotic and an effective amount one or more PMF stimulating compounds, permits increased efficacy of known aminoglycoside antibiotics, by enhancing their uptake via PMF stimulation in bacterial cells, such as persister cells.

Accordingly, in some aspects, provided herein are methods for treating a chronic or persisting bacterial infection, the methods comprising administering to a subject having or at risk for a chronic or persisting bacterial infection an effective amount of an aminoglycoside antibiotic and an effective amount of at least one proton motive force (PMF) stimulating compound as an adjuvant. The methods described herein can, in some aspects and embodiments, be used to inhibit, delay formation of, treat, and/or prevent or provide prophylactic treatment of chronic infections and infections by persistent bacteria, including bacterial infections caused by slow growing, stationary-phase or biofilm-forming bacteria in animals, including humans.

In some aspects, provided herein are methods for inhibiting a chronic or persisting bacterial infection, the methods comprising administering to a patient having or at risk for a chronic or persisting bacterial infection an effective amount of an aminoglycoside antibiotic and an effective amount of at least one proton motive force (PMF) stimulating compound as an adjuvant.

In some aspects, provided herein are methods for preventing a chronic or persisting bacterial infection, the methods comprising administering to a patient having or at risk for a chronic or persisting bacterial infection an effective amount of an aminoglycoside antibiotic and an effective amount of at least one proton motive force (PMF) stimulating compound as an adjuvant.

In some aspects, provided herein are methods for treating a subject having an infection caused by persister bacterial cells, the methods comprising administering to a patient having an infection caused by persister bacterial cells an effective amount of an aminoglycoside antibiotic and an effective amount of at least one proton motive force (PMF) stimulating compound as an adjuvant.

In some aspects, provided herein are methods for treating a chronic or persisting bacterial infection, comprising: administering to a patient having a chronic or persisting bacterial infection and undergoing treatment with an aminoglycoside antibiotic, an effective amount of at least one proton motive force stimulating compound as an adjuvant.

The terms "persistent cell" or "persister bacterial cells" are used interchangeably herein and refer to a metabolically dormant subpopulation of microorganisms, typically bacteria, which are not sensitive to antimicrobial agents such as antibiotics. Persisters typically are not responsive, i.e. are not killed or inhibited by antibiotics, as they have, for example, non-lethally downregulated the pathways on which the antibiotics act. Persisters can develop at non-lethal (or sub-lethal) concentrations of the antibiotic.

In some embodiments of these methods and all such methods described herein, the aminoglycoside antibiotic is selected from streptomycin, gentamicin, kanamycin A, neomycin B, neomycin C, framycetin, paromomycin, ribostamycin, amikacin, arbekacin, bekanamycin (kanamycin B), dibekacin, tobramycin, spectinomycin, hygromycin B, paromomycin sulfate, netilmicin, sisomicin, isepamicin, verdamicin, astromicin, neamine, ribostamycin, and paromomycinlividomycin. In some embodiments of these methods and all such methods described herein, the aminoglycoside antibiotic is selected from streptomycin, gentamicin, and kanamycin A. In some embodiments of these methods and all such methods described herein, the aminoglycoside antibiotic is tobramycin.

In some embodiments of these methods and all such methods described herein, the proton-motive force (PMF) stimulating compound is a metabolite or a metabolic stimuli, such as, for example, a compound that enters upper glycolysis in bacteria, or a variant thereof. In some embodiments of these methods and all such methods described herein, the proton-motive force (PMF) stimulating compound is selected from glucose, mannitol, fructose, and pyruvate. In some embodiments, metabolites for use as proton-motive force (PMF) stimulating compounds in the compositions and methods described herein include, but are not limited to, lactate, glucosamine, sorbitol, n-acetyl glucosamine, n-acetyl muramic acid, maltose, galactosamine, trehaloseribose, arabinose, gluconate, glycerol, galactarate, and analogs or derivatives thereof. In some embodiments of these methods and all such methods described herein, the proton-motive force (PMF) stimulating compound is selected from ribose, arabinose, gluconate, glycerol, and galactarate.

As used herein, the terms "inhibit", "decrease," "reduce," "inhibiting" and "inhibition" have their ordinary and customary meanings to generally mean a decrease by a statistically significant amount, and include inhibiting the growth or cell division of a persistent, slow growing, stationary-phase causing a chronic infection, and/or biofilm bacteria, as well as killing such bacteria. Such inhibition is an inhibition of about 1% to about 100% of the growth of the bacteria versus the growth of bacteria in the absence of the effective amount of the aminoglycoside antibiotic and the effective amount one or more PMF stimulating compounds. Preferably, the inhibition is an inhibition of about at least 10%, at least 20%, at least 30%, at least 40%, at least 50%, at least 60%, at least 70%, at least 80%, at least 90%, at least 95%, at least 98%, at least 99%, up to including 100%, of the growth or survival of the bacteria in comparison to a reference or control level in the absence of the effective amount of the aminoglycoside antibiotic and the effective amount one or more PMF stimulating compounds.

The terms "subject" and "individual" are used interchangeably herein, and refer to an animal, for example a human, recipient of the aminoglycoside antibiotic and the one or more PMF stimulating compounds, such as, for example, gentamicin and mannitol. For treatment of those disease states which are specific for a specific animal, such as a human subject, the term "subject" refers to that specific animal. The terms 'non-human animals' and 'non-human mammals' are used interchangeably herein, and include mammals such as rats, mice, rabbits, sheep, cats, dogs, cows, pigs, and non-human primates. The term "subject" can also encompass any vertebrate including but not limited to mammals, reptiles, amphibians and fish.

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder, such as a chronic infection, and include one or more of: ameliorating a symptom of a chronic infection or persistent, slow growing, stationary-phase or biofilm bacterial infection in a subject; blocking or ameliorating a recurrence of a symptom of a chronic infection or persistent, slow growing, stationary-phase or biofilm bacterial infection in a subject; decreasing in severity and/or frequency a symptom of a chronic infection or persistent, slow growing, stationary-phase or biofilm bacterial infection in a subject; and stasis, decreasing, or inhibiting growth of a chronic infection or persistent, slow growing, stationary-phase or biofilm bacterial infection in a subject. Treatment means ameliorating, blocking, reducing, decreasing or inhibiting by about 1% to about 100% versus a subject to whom the effective amount of the aminoglycoside antibiotic and the effective amount one or more PMF stimulating compounds has not been administered. Preferably, the ameliorating, blocking, reducing, decreasing or inhibiting is about at least 5%, at least 10%, at least 20% at least 30%, at least 40%, at least 50%, at least 60%, at least 70%, at least 80%, at least 90%, at least 95%, at least 98%, at least 99%, up to including 100% versus a subject to whom the effective amount of the aminoglycoside antibiotic and the effective amount one or more PMF stimulating compounds has not been administered. Treatment is generally considered "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

As used herein, the phrase "alleviating a symptom of a persistent or chronic infection" is ameliorating any condition or symptom associated with the persistent infection. Alternatively, alleviating a symptom of a persistent infection can involve reducing the infectious microbial (such as bacterial) load in the subject relative to such load in an untreated control. As compared with an equivalent untreated control, such reduction or degree of prevention is at least 5%, at least 10%, at least 20%, at least 40%, at least 50%, at least 60%, at least 80%, at least 90%, at least 95%, or 100% as measured by any standard technique. Desirably, the persistent infection is completely cleared as detected by any standard method known in the art, in which case the persistent infection is considered to have been treated. A patient who is being treated for a persistent infection is one who a medical practitioner has diagnosed as having such a condition. Diagnosis can be by any suitable means. Diagnosis and monitoring can involve, for example, detecting the level of microbial load in a biological sample (for example, a tissue biopsy, blood test, or urine test), detecting the level of a surrogate marker of the microbial infection in a biological sample, detecting symptoms associated with persistent infections, or detecting immune cells involved in the immune response typical of persistent infections (for example, detection of antigen specific T cells or antibody production).

As used herein, the terms "preventing" and "prevention" have their ordinary and customary meanings, and include one or more of: preventing chronic infection or colonization of a persistent, slow growing, stationary-phase or biofilm bacteria in a subject, or on a surface or on a porous material; preventing an increase in the growth of a population of a persistent, slow growing, stationary-phase or biofilm bacteria in a subject, or on a surface or on a porous material; preventing development of a disease caused by a persistent, slow growing, stationary-phase or biofilm bacteria in a subject; and preventing symptoms of a chronic infection or disease caused by a persistent, slow growing, stationary-phase or biofilm bacteria in a subject. As used herein, the prevention lasts at least about 0.5 days, 1 day, 2 days, 3 days, 4 days, 5 days, 6 days, 7 days, 10 days, 12 days, 15 days, 20 days, 25 days, 30 days, 35 days, 40 days or more days after administration or application of the effective amount of the aminoglycoside antibiotic and the effective amount one or more PMF stimulating compounds, as described herein.

In some embodiments of the methods of treatment of chronic or persistent bacterial infections or inhibiting the growth of persistent bacteria described herein, the subject or surface can be administered or contacted with a second antibiotic concurrently or along with the effective amount of the aminoglycoside antibiotic and the effective amount one or more PMF stimulating compounds. Suitable second antibiotics include, for example, aminoglycosides (e.g., gentamicin, streptomycin, kanamycin), β-lactams (e.g., penicillins and cephalosporins), vancomycins, bacitracins, macrolides (e.g., erythromycins), lincosamides (e.g., clindomycin), chloramphenicols, tetracyclines, amphotericins, cefazolins, clindamycins, mupirocins, sulfonamides and trimethoprim, rifampicins, metronidazoles, quinolones, novobiocins, polymixins, gramicidins, or any salts or variants thereof.

In some aspects and embodiments of the methods of inhibition, delay of formation, treatment, prophylaxis and prevention of a persistent, slow growing, stationary-phase or biofilm bacteria described herein, the methods can be used for achieving a systemic and/or local effect against relevant bacteria shortly before or after an invasive medical treatment, such as surgery or insertion of an in-dwelling medical device (e.g. joint replacement (hip, knee, shoulder, etc.)). Treatment can be continued after invasive medical treatment, such as post-operatively or during the in-body time of the device.

Accordingly, in some aspects provided herein are methods of inhibiting or preventing formation or colonization of a persistent, slow growing, stationary-phase or biofilm bacteria in a subject before, during, or after an invasive medical treatment, comprising administering to a subject before, during, and/or after an invasive medical treatment an effective amount of an aminoglycoside antibiotic and an effective amount of at least one proton motive force (PMF) stimulating compounds as an adjuvant.

In some such embodiments, the aminoglycoside antibiotic and at least one proton motive force (PMF) stimulating compound can be administered once, twice, thrice or more, from 1 day, 2 days, 3 days, 4 days, 5 days, 6 days, 7 days or more, to 10 hours, 9 hours, 8 hours, 7 hours, 6 hours, 5 hours, 4 hours, 3 hours, 2 hours, or 1 hour or immediately before surgery for permitting a systemic or local presence of the aminoglycoside antibiotic and at least one proton motive force (PMF) stimulating compound. The pharmaceutical composition or glycopeptide antibiotic can, in some embodiments, be administered after the invasive medical treatment for a period of time, such as 1 day, 2 days, 3 days, 4 days, 5 days or 6 days, 1 week, 2 weeks, 3 weeks or more, or for the entire time in which the device is present in the body of the subject.

As used herein, the term "bi-weekly" refers to a frequency of every 13-15 days, the term "monthly" refers a frequency of every 28-31 days and "bi-monthly" refers a frequency of every 58-62 days.

In some embodiments of the methods described herein, the surface of an in-dwelling device is coated by a solution, such as through bathing or spraying, containing a concentration of about 10 μg/ml to about 500 mg/ml of the aminoglycoside antibiotic and at least one proton motive force (PMF) stimulating compound described herein. In particular embodiments, more specific ranges of concentrations of the aminoglycoside antibiotic and at least one proton motive force (PMF) stimulating compound can be used, including: about 10 ug/ml to about 1 mg/ml, about 1 mg/ml to about 100 mg/ml, about 10 mg/ml to about 500 mg/ml, about 50 mg/ml to about 200 mg/ml, about 10 mg/ml to about 100 mg/ml, about 100 mg/ml to about 500 mg/ml. In some embodiments, specific concentrations of the aminoglycoside antibiotic and at least one proton motive force (PMF) stimulating compound can be used, including: about 10 ug/ml, about 50 ug/ml, about 100 ug/ml, about 250 ug/ml, about 500 ug/ml, about 750 ug/ml, about 1 mg/ml, about 5 mg/ml, about 10 mg/ml, about 15 mg/ml, about 20 mg/ml, about 25 mg/ml, about 30 mg/ml, about 40 mg/ml, about 50 mg/ml, about 75 mg/ml, about 100 mg/ml, about 250 mg/ml, about 500 mg/ml, about 600 mg/ml, about 750 mg/ml, and about 900 mg/ml.

In some embodiments of the methods described herein, the concentration of the at least one proton motive force (PMF) stimulating compound is at least 5 mM or greater, at least 6 mM or greater, at least 7 mM or greater, at least 8 mM or greater, at least 9 mM or greater; at least 10 mM or greater, at least 11 mM or greater, at least 12 mM or greater, at least 13 mM or greater, at least 14 mM or greater; at least 15 mM or greater, at least 16 mM or greater, at least 17 mM or greater, at least 18 mM or greater, at least 19 mM or greater; at least 20 mM or greater, at least 25 mM or greater, at least 50 mM or greater, at least 100 mM or greater, at least 500 mM or greater, or more, or all ranges or amounts in-between.

When being applied to an in-dwelling medical device, the surface can be coated by the solution containing an aminoglycoside antibiotic and at least one proton motive force (PMF) stimulating compound before its insertion in the body.

In some embodiments of the methods described herein, a subject refers to a human subject having a chronic infection or at increased risk for a chronic infection or biofilm formation. A subject that has a chronic infection is a subject having objectively measurable bacterial cells present in the subject's body. A subject that has increased risk for a chronic infection includes subjects with an in-dwelling medical device, for example, or a subject having or having had a surgical intervention.

In some embodiments of the aspects described herein, the methods of treating a subject having a chronic infection or at increased risk for a chronic infection, further comprise the step of selecting, diagnosing, or identifying a subject having or at increased risk for chronic infection or biofilm formation. In such embodiments, a subject is identified as having a chronic infection by objective determination of the presence of bacterial cells in the subject's body by one of skill in the art. Such objective determinations can be performed through the sole or combined use of tissue analyses, blood analyses, urine analyses, and bacterial cell cultures, in addition to the monitoring of specific symptoms associated with a chronic infection or biofilm formation.

In some embodiments of the methods described herein, the subject having or at risk for a chronic infection is an immunocompromised subject, such as, for example, HIV-positive patients, who have developed or are at risk for developing pneumonia from either an opportunistic infection or from the reactivation of a suppressed or latent infection; subjects with cystic fibrosis, chronic obstructive pulmonary disease, and other such immunocompromised and/or institutionalized patients.

As used herein, "persistent infections" refer to those infections that, in contrast to acute infections, are not effectively cleared by a host immune response or by antibiotic administration. Persistent infections include for example, latent, chronic and slow infections. In a "chronic infection," the infectious agent can be detected in the subject at all times. However, the signs and symptoms of the disease can be present or absent for an extended period of time. Non-limiting examples of chronic infection include a variety of bacterial infections, as described herein below, as well as secondary bacterial infections resulting from or caused by infection with another agent that suppresses or weakens the immune system, such as chronic viral infections, such as, for example, hepatitis B (caused by heptatitis B virus (HBV)) and hepatitis C (caused by hepatitis C virus (HCV)) adenovirus, cytomegalovirus, Epstein-Barr virus, herpes simplex virus 1, herpes simplex virus 2, human herpesvirus 6, varicella-zoster virus, hepatitis B virus, hepatitis D virus, papilloma virus, parvovirus B19, polyomavirus BK, polyomavirus JC, measles virus, rubella virus, human immunodeficiency virus (HIV), human T cell leukemia virus I, and human T cell leukemia virus II, as well as secondary bacterial infections resulting from or caused by infection with a persistent parasitic persistent infection, such as, for example, *Leishmania, Toxoplasma, Trypanosoma, Plasmodium, Schistosoma*, and Encephalitozoon.

Examples of infectious bacteria include, but are not limited to: *Helicobacterpyloris, Borelia burgdorferi, Legionella pneumophilia, Mycobacteria* sps (such as *M. tuberculosis, M. avium, M. intracellulare, M. kansaii, M. gordonae*), *Staphylococcus aureus, Staphylococcus epidermidis, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus bovis, Streptococcus* (anaerobic sps.), *Streptococcus pneumoniae,* pathogenic *Campylobacter* sp., *Enterococcus* sp., *Haemophilus influenzae, Bacillus anthracis, Bacillus cereus, Bifidobacterium bifidum, corynebacterium diphtheriae, corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus monilifbrmis, Treponema palladium, Treponema pertenue, Leptospira, Actinomyces israelii, Lactobacillus* spp.; *Nocardia* spp.; *Rhodococcus equi* (*coccobacillus*); *Erysipelothrix rhusiopathiae; Actinomyces* spp.; *Clostridium botulinum; Clostridium difficile; Mobiluncus* spp., *Peptostreptococcus* spp.; *Moraxella catarrhalis; Veillonella* spp.; *Actinobacillus actinomycetemcomitans; Acinetobacter baumannii; Bordetella pertussis; Brucella* spp.; *Campylobacter* spp.; *Capnocytophaga* spp.; *Cardiobacterium hominis; Eikenella corrodens; Francisella tularensis; Haemophilus ducreyi; Kingella kingae; Pasteurella multocida; Klebsiella granulomatis; Citrobacter* spp., *Enterobacter* spp.; *Escherichia coli; Klebsiella pneumoniae; Proteus* spp.; *Salmonella enteriditis; Salmonella typhi; Shigella* spp.; *Serratia marcescens; Yersinia enterocolitica; Yersinia pestis; Aeromonas* spp.; *Plesiomonas shigelloides; Vibrio cholerae; Vibrio parahaemolyticus; Vibrio vulnificus; Acinetobacter* spp.; *Flavobacterium* spp.; *Burkholderia cepacia; Burkholderia pseudomallei; Xanthomonas maltophilia* or *Stenotrophomonas maltophila; Bacteroides fragilis; Bacteroides* spp.; *Prevotella* spp.; *Fusobacterium* spp.; *Spirillum minus; Borrelia burgdorferi; Borrelia recurrentis; Bartonella henselae; Chlamydia trachomatis; Chlamydophila pneumoniae; Chlamydophila psittaci; Coxiella burnetii; Ehrlichia chaffeensis; Anaplasma phagocytophilum; Legionella* spp.; *Leptospira* spp.; *Rickettsia rickettsia; Orientia tsutsugamushi;* and *Treponema pallidum.* Mycobacterial infections that can be treated using the methods and compositions described herein include, but are not limited to, those caused by: *M. abscessus, M. africanum, M. asiaticum, Mycobacterium avium* complex (MAC), *M. avium paratuberculosis, M. bovis, M. chelonae, M. fortuitum, M. gordonae, M. haemophilum, M. intracellulare, M. kansasii, M. lentiflavum, M. leprae, M. liflanclii, M. malmoense, M.*

*marinum, M. microti, M. phlei, M. pseudoshottsii, M. scrofillaceum, M. shottsii, M. smegmatis, M. triplex, M. tuberculosis, M. ulcerans, M. uvium,* and *M. xenopi.*

The compositions and methods described herein comprising aminoglycoside antibiotics and PMF stimulating compounds are contemplated for use in treating chronic infections with these bacterial species. Other infectious organisms (such as protists) include: *Plasmodium falciparum* and *Toxoplasma gondii*. The compositions and methods described herein comprising aminoglycoside antibiotics and PMF stimulating compounds are also contemplated for use in treating infections with these species.

Non-limiting examples of disorders/diseases caused by bacterial infections include, but are not limited to, pneumonia, bacterial meningitis, cholera, diphtheria, tuberculosis, anthrax, botulism, brucellosis, campylobacteriosis, typhus, ear infections, including recurrent ear infections, pneumonia, including recurrent pneumonia, gonorrhea, listeriosis, lyme disease, rheumatic fever, pertussis (Whooping Cough), plague, *salmonellosis*, scarlet fever, shigellosis, sinusitis, including chronic sinusitis, syphilis, tetanus, trachoma, tularemia, typhoid fever, and urinary tract infections, including chronic urinary tract infections.

Accordingly, in various embodiments of methods and compositions and methods described herein, the aminoglycoside antibiotic used is determined based on the nature of the bacterial infection or chronic infection in the subject.

For example, in some embodiments of the compositions and methods described herein, if the chronic infection is: infective endocarditis caused by *enterococcus* when the organism is not sensitive to Gentamicin; tuberculosis in combination with other anti-TB drugs; and plague (*Yersinia pestis*), the aminoglycoside antibiotic administered is streptomycin.

In some embodiments of the compositions and methods described herein, the aminoglycoside antibiotic is gentamicin, when the bacterial infection is a Gram-negative organism, such as, for example, *Pseudomonas, Proteus, Serratia,* and when the bacterial infection is Gram-positive *Staphylococcus* species, *Yersinia pestis*, its relatives, and *Francisella tularensis*. In some embodiments of the compositions and methods described herein, the aminoglycoside antibiotic is gentamicin, when the chronic infection being treated or prevented is, for example, bacteremia, bacterial endocarditis, brucellosis, infections associated with external burns, infections associated with cystic fibrosis, endocarditis, prosthetic valve infections due to *S. viridans* and *S. bovis*, native valve infections due to staphylococci, prosthetic valve infections due to staphylococci, native valve or prosthetic valve infections due to penicillin-resistant enterococci, infections associated with endometritis, infections associated with febrile neutropenia, intraabdominal infections, meningitis, infections associated with osteomyelitis, infections associated with pelvic inflammatory disease, infections associated with peritonitis, infections associated with plague, infections associated with pneumonia, infections associated with pyelonephritis, infections associated with skin or soft tissue, infections associated with surgery, and infections associated with tularemia.

In some embodiments of the compositions and methods described herein, the aminoglycoside antibiotic is tobramycin, when the bacterial infection is an aerobic and facultative Gram-positive microorganisms, such as, for example, *Staphylococcus aureus*; or an aerobic and facultative Gram-negative microorganism, such as, for example, *Citrobacter* sp., *Enterobacter* sp., *Escherichia coli*, *Klebsiella* sp., *Morganella morganii*, *Pseudomonas aeruginosa*, *Proteus mirabilis*, *Proteus vulgaris*, *Providencia* sp., and *Serratia* sp. In some embodiments of the compositions and methods described herein, the aminoglycoside antibiotic is tobramycin, when the chronic infection being treated or prevented is, for example, bacteremia, infections associated with external burns, infections associated with cystic fibrosis, endocarditis, infections associated with febrile neutropenia, intraabdominal infections, meningitis, infections associated with osteomyelitis, infections associated with peritonitis, infections associated with pneumonia, infections associated with pyelonephritis, sepsis, shunt infections, infections associated with skin or soft tissue, and infections associated with tularemia.

In some embodiments of the compositions and methods described herein, the aminoglycoside antibiotic is Sisomicin (BACTOCEAZE or ENSAMYCIN), when the bacterial infection is caused by a Gram-positive bacteria, or *Pseudomonas aeruginosa.*

In some embodiments of the compositions and methods described herein, the aminoglycoside antibiotic is arbekacin, when the chronic infection is caused by multi-resistant bacteria, such as, for example, methicillin-resistant *Staphylococcus aureus* (MRSA), as well as enteric bacteria and other eubacteria.

In some embodiments of the compositions and methods described herein, the aminoglycoside antibiotic is amikacin, when the chronic infection is caused by multidrug resistant Gram negative bacteria, such as, for example, *Pseudomonas aeruginosa, Acinetobacter,* and *Enterobacter*, as well as, for example, *Serratia marcescens* and *Providencia stuartii*, and non-tubercular mycobacterial infections and tuberculosis, when first line drugs fail to control the infection.

In some embodiments of the compositions and methods described herein, the aminoglycoside antibiotic is neomycin, when the infection is caused by a Gram-negative bacteria, and, in some embodiments, a Gram-positive bacteria.

In some embodiments of the compositions and methods described herein, the aminoglycoside antibiotic is framycetin, when the infection is a skin, nose, ear, and/or eye infection.

In some embodiments of the compositions and methods described herein, the aminoglycoside antibiotic is paromomycin, when the infection is an intestinal infection, such as, for example, cryptosporidiosis, amoebiasis, and leishmaniasis.

Also provided herein, in some aspects, are methods of inhibiting or delaying the formation of biofilms, comprising administering to a subject in need thereof or contacting a surface with an effective amount of an aminoglycoside antibiotic and an effective amount one or more PMF stimulating compounds.

As used herein, a "biofilm" refers to mass of microorganisms attached to a surface, such as a surface of a medical device, and the associated extracellular substances produced by one or more of the attached microorganisms. The extracellular substances are typically polymeric substances that commonly include a matrix of complex polysaccharides, proteinaceous substances and glycopeptides. The microorganisms can include, but are not limited to, bacteria, fungi and protozoa. In a "bacterial biofilm," the microorganisms include one or more species of bacteria. The nature of a biofilm, such as its structure and composition, can depend on the particular species of bacteria present in the biofilm. Bacteria present in a biofilm are commonly genetically or phenotypically different than corresponding bacteria not in a biofilm, such as isolated bacteria or bacteria in a colony. "Polymicrobic biofilms" are biofilms that include a plurality of bacterial species.

As used herein, the terms and phrases "delaying", "delay of formation", and "delaying formation of" have their ordinary and customary meanings, and are generally directed to increasing the period of time prior to the formation of biofilm, or a slow growing bacterial infection in a subject or on a surface. The delay may be, for example, about 12 hours, about 18 hours, about 24 hours, about 36 hours, about 48 hours, about 60 hours, about 72 hours, about 84 hours, about 96 hours, about 5 days, 6 days, 7 days, 8 days, 9 days, 10 days, or more. Inhibiting formation of a biofilm, as used herein, refers to avoiding the partial or full development or progression of a biofilm, for example, on a surface, such as a surface of an indwelling medical device.

The skilled artisan will understand that the methods of inhibiting and delaying the formation of biofilms can be practiced wherever bacteria, such as persistent, slow-growing, stationary-phase, or biofilm forming bacteria, can be encountered. For example, the methods described herein can be practiced on the surface of or inside of an animal, such as a human; on an inert surface, such as a counter or bench top; on a surface of a piece of medical or laboratory equipment; on a surface of a medical or laboratory tool; or on a surface of an in-dwelling medical device.

In some aspects, provided herein are methods of inhibiting the formation of a biofilm on a surface or on a porous material, comprising applying to or contacting a surface or a porous material upon which a biofilm can form an aminoglycoside antibiotic and one or more PMF stimulating compounds in an amount sufficient to inhibit the formation of a biofilm. In some embodiments of these methods and all such methods described herein, the surface is an inert surface, such as the surface of an in-dwelling medical device.

In some aspects, provided herein are methods of delaying the formation of a biofilm on a surface or on a porous material, comprising applying to or contacting a surface or a porous material upon which a biofilm can form an aminoglycoside antibiotic and one or more PMF stimulating compounds in an amount sufficient to delay the formation of a biofilm. In some embodiments of these methods and all such methods described herein, the surface is an inert surface, such as the surface of an in-dwelling medical device.

In some aspects, provided herein are methods of preventing the colonization of a surface by persistent bacteria, comprising applying to or contacting a surface with an aminoglycoside antibiotic and one or more PMF stimulating compounds in an amount sufficient to prevent colonization of the surface by persistent bacteria.

In the embodiments of the methods described herein directed to inhibiting or delaying the formation of a biofilm, or preventing the colonization of a surface by persistent bacteria, the material comprising the surface or the porous material can be any material that can be used to form a surface or a porous material. In some such embodiments, the material is selected from: polyethylene, polytetrafluoroethylene, polypropylene, polystyrene, polyacrylamide, polyacrylonitrile, poly(methyl methacrylate), polyamide, polyester, polyurethane, polycarbonate, silicone, polyvinyl chloride, polyvinyl alcohol, polyethylene terephthalate, cobalt, a cobalt-base alloy, titanium, a titanium base alloy, steel, silver, gold, lead, aluminum, silica, alumina, yttria stabilized zirconia polycrystal, calcium phosphate, calcium carbonate, calcium fluoride, carbon, cotton, wool and paper.

In embodiments of the methods described herein of inhibiting or delaying the formation of a biofilm, or preventing the colonization of a surface by persistent bacteria, a second antibiotic can be applied concurrently with the aminoglycoside antibiotic and one or more PMF stimulating compounds. Suitable second antibiotics include, for example, aminoglycosides (e.g., gentamicin, streptomycin, kanamycin), β-lactams (e.g., penicillins and cephalosporins), vancomycins, bacitracins, macrolides (e.g., erythromycins), lincosamides (e.g., clindomycin), chloramphenicols, tetracyclines, amphotericins, cefazolins, clindamycins, mupirocins, sulfonamides and trimethoprim, rifampicins, metronidazoles, quinolones, novobiocins, polymixins, gramicidins, or any salts or variants thereof.

In some embodiments of these methods and all such methods described herein, the persistent, slow growing, stationary-phase or biofilm bacteria is any bacterial species or population that comprises persistent cells, can exist in a slow growing or stationary-phase, and/or that can form a biofilm. In some such embodiments, the bacteria is *Staphylococcus aureus*, *Staphylococcus epidermidis*, a vancomycin-susceptible enterococci, a vancomycin-resistant enterococci, a *Staphylococcus* species or a *Streptococcus* species. In some such embodiments, the bacteria is selected from vancomycin (VAN)-susceptible *Enterococcus faecalis* (VSE), VAN-resistant *E. faecalis* (VRE), and *Staph. epidermidis*.

As used herein, the term "contacting" is meant to broadly refer to bringing a bacterial cell and an aminoglycoside antibiotic and one or more PMF stimulating compounds into sufficient proximity that the aminoglycoside antibiotic and one or more PMF stimulating compounds can exert their effects on any bacterial cell present. The skilled artisan will understand that the term "contacting" includes physical interaction between an aminoglycoside antibiotic and one or more PMF stimulating compounds and a bacterial cell, as well as interactions that do not require physical interaction.

The methods described herein further encompass surfaces coated by an aminoglycoside antibiotic and one or more PMF stimulating compounds, and/or impregnated with an aminoglycoside antibiotic and one or more PMF stimulating compounds. Such surfaces include any that can come into contact with a persistent, slow growing, stationary-phase, biofilm bacteria. In some such embodiments, such surfaces include any surface made of an inert material (although surfaces of a living animal are encompassed within the scope of the methods described herein), including the surface of a counter or bench top, the surface of a piece of medical or laboratory equipment or a tool, the surface of a medical device such as a respirator, and the surface of an in-dwelling medical device. In some such embodiments, such surfaces include those of an in-dwelling medical device, such as surgical implants, orthopedic devices, prosthetic devices and catheters, i.e., devices that are introduced to the body of an individual and remain in position for an extended time. Such devices include, but are not limited to, artificial joints, artificial hearts and implants; valves, such as heart valves; pacemakers; vascular grafts; catheters, such as vascular, urinary and continuous ambulatory peritoneal dialysis (CAPD) catheters; shunts, such as cerebrospinal fluid shunts; hoses and tubing; plates; bolts; valves; patches; wound closures, including sutures and staples; dressings; and bone cement.

As used herein, the term "indwelling medical device," refers to any device for use in the body of a subject, such as intravascular catheters (for example, intravenous and intraarterial), right heart flow-directed catheters, Hickman catheters, arteriovenous fistulae, catheters used in hemodialysis and peritoneal dialysis (for example, silastic, central venous, Tenckhoff, and Teflon catheters), vascular access ports, indwelling urinary catheters, urinary catheters, silicone catheters, ventricular catheters, synthetic vascular prostheses (for example, aortofemoral and femoropopliteal), prosthetic heart valves, prosthetic joints, orthopedic implants, penile implants, shunts (for example, Scribner, Torkildsen, central nervous system, portasystemic, ventricular, ventriculoperitoneal), intrauterine devices, tampons, dental implants, stents (for example, ureteral stents), artificial voice prostheses, tympanostomy tubes, gastric feeding tubes, endotracheal tubes, pacemakers, implantable defibrillators, tubing, cannulas, probes, blood monitoring devices, needles, and the like. A subcategory of indwelling medical devices refer to implantable devices that are typically more deeply and/or permanently introduced into the body. Indwelling medical devices can be introduced by any suitable means, for example, by percutaneous, intravascular, intraurethral, intraorbital, intratracheal, intraesophageal, stomal, or other route, or by surgical implantation, for example intraarticular placement of a prosthetic joint.

According to some embodiments of the methods described herein, the in-dwelling medical device is coated by a solution, such as through bathing or spraying, containing a concentration of about 10 ug/ml to about 500 mg/ml of an aminoglycoside antibiotic and one or more PMF stimulating compounds. In some embodiments, more specific ranges of concentrations of the an aminoglycoside antibiotic and one or more PMF stimulating compounds can be used, including: about 10 ug/ml to about 1 mg/ml, about 1 mg/ml to about 100 mg/ml, about 10 mg/ml to about 500 mg/ml, about 50 mg/ml to about 200 mg/ml, about 10 mg/ml to about 100 mg/ml, about 100 mg/ml to about 500 mg/ml. In some embodiments, specific concentrations of an aminoglycoside antibiotic and one or more PMF stimulating compounds can be used, including: about 10 ug/ml, about 50 ug/ml, about 100 ug/ml, about 250 ug/ml, about 500 ug/ml, about 750 ug/ml, about 1 mg/ml, about 5 mg/ml, about 10 mg/ml, about 15 mg/ml, about 20 mg/ml, about 25 mg/ml, about 30 mg/ml, about 40 mg/ml, about 50 mg/ml, about 75 mg/ml, about 100 mg/ml, about 250 mg/ml, about 500 mg/ml, about 600 mg/ml, about 750 mg/ml, and about 900 mg/ml. The in-dwelling medical device can be coated by the solution comprising an aminoglycoside antibiotic and one or more PMF stimulating compounds before its insertion in the body.

Dosing and Modes of Administration

One key advantage of the methods, uses and compositions comprising the aminoglycoside antibiotics and/or PMF stimulating compounds described herein, is the ability of producing marked anti-bacterial effects in a human subject having a chronic infection without causing significant toxicities or adverse effects. By adding PMF stimulating compounds to a therapeutic regimen or method, the dosage of the aminoglycoside antibiotic being administered can, in some embodiments, be reduced relative to the normally administered dosage. The efficacy of the treatments and methods described herein can be measured by various parameters commonly used in evaluating treatment of infections, including but not limited to, reduction in rate of bacterial growth, the presence or number of bacterial cells in a sample obtained from a subject, overall response rate, duration of response, and quality of life.

Accordingly, a "therapeutically effective amount" or "effective amount" of an aminoglycoside antibiotic or one or more PMF stimulating compounds, to be administered to a subject is governed by various considerations, and, as used herein, refers to the minimum amount necessary to prevent, ameliorate, or treat, or stabilize, a disorder or condition, such as chronic infection. An effective amount as used herein also includes an amount sufficient to delay the development of a symptom of a chronic infection, alter the course of a chronic infection (for example but not limited to, slow the progression of a symptom of the chronic infection, such as growth of the bacterial population causing the chronic infection), or reverse a symptom of the chronic infection. Thus, it is not possible to specify the exact "effective amount". However, for any given case, an appropriate "effective amount" can be determined by one of ordinary skill in the art using only routine experimentation.

Effective amounts, toxicity, and therapeutic efficacy of the aminoglycoside antibiotics or one or more PMF stimulating compounds described herein, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the aminoglycoside antibiotics or one or more PMF stimulating compounds), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Depending on the type and severity of the infection, about 1 µg/kg to 100 mg/kg (e.g., 0.1-20 mg/kg) of an aminoglycoside antibiotic, such as gentamicin, or PMF stimulating compound, such as mannitol, is an initial candidate dosage range for administration to the subject, whether, for example, by one or more separate administrations, or by continuous infusion. A typical daily dosage might range from about 1 µg/kg to about 100 mg/kg or more, depending on the factors mentioned above. For repeated administrations over several days or longer, depending on the condition, the treatment is sustained until the infection is treated or cleared, as measured by the methods described above or known in the art. However, other dosage regimens may be useful. The progress of the therapeutic methods described herein is easily monitored by conventional techniques and assays, such as those described herein, or known to one of skill in the art.

For example, gentamicin can be highly nephrotoxic, particularly if multiple doses accumulate over a course of treatment. For this reason gentamicin can be dosed by body weight. Various formulae exist for calculating gentamicin dosage, and are known to those of skill in the art. Also, trough and peak serum levels of gentamicin can be monitored during standard treatment regimens, generally before and after the third dose is infused. A number of factors and determinants should be taken into account when using gentamicin in the methods described herein.

In some embodiments, where neilmcin is the aminoglycoside antibiotic, available dosage forms include 10 mg/mL, 25 mg/1 mL, 50 mg/mL, 100 mg/mL, and 150 mg/1.5 mL.

The duration of the therapeutic methods described herein can continue for as long as medically indicated or until a desired therapeutic effect (e.g., those described herein) is achieved. In certain embodiments, administration of a combination of an aminoglycoside antibiotic and one or more PMF stimulating compounds is continued for at least 1 month, at least 2 months, at least 4 months, at least 6 months, at least 8 months, at least 10 months, at least 1 year, at least 2 years, at least 3 years, at least 4 years, at least 5 years, at least 10 years, at least 20 years, or for at least a period of years up to the lifetime of the subject. In some embodiments of the methods described herein, administration is continued for as long as an in-dwelling device is present in the subject.

The aminoglycoside antibiotics and PMF stimulating compounds described herein, can be administered, individually, but concurrently, in some embodiments, or, in other embodiments, simultaneously, for example in a single formulation comprising both an aminoglycoside antibiotic and one or more PMF stimulating compounds, to a subject, e.g., a human subject, in accordance with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Exemplary modes of administration of the aminoglycoside antibiotics and PMF stimulating compounds, include, but are not limited to, injection, infusion, inhalation (e.g., intranasal or intratracheal), ingestion, rectal, and topical (including buccal and sublingual) administration. Local administration can be used if, for example, extensive side effects or toxicity is associated with the aminoglycoside antibiotic and/or PMF stimulating compounds, and to, for example, permit a high localized concentration of the PMF stimulating compound to the infection site. An ex vivo strategy can also be used for therapeutic applications. Accordingly, any mode of administration that delivers the aminoglycoside antibiotics and PMF stimulating compounds systemically or to a desired surface or target, and can include, but is not limited to, injection, infusion, instillation, and inhalation administration. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of an aminoglycoside antibiotics and PMF stimulating compounds other than directly into a target site, tissue, or organ, such as the lung, such that it enters the subject's circulatory system and, thus, is subject to metabolism and other like processes.

The aminoglycoside antibiotic being used to treat an infection or inhibit biofilm formation in a subject can determine the mode of administration to be used. For example, most aminoglycoside antibiotics are not well-absorbed via the intestine and GI tract, and thus oral administration is ineffective.

Accordingly, in some embodiments of the methods described herein, when the aminoglycoside antibiotic is streptomycin, administration is by intramuscular injection or intravenous administration. In some such embodiments, the administration is not via oral administration.

In some embodiments of the methods described herein, when the aminoglycoside antibiotic is gentamicin, administration is via intravenous administration, intramuscular administration, or topical administration to treat infections. In some such embodiments, the administration is not via oral administration.

In some embodiments of the methods described herein, when the aminoglycoside antibiotic is Kanamycin A, administration is via oral, intravenous, and intramuscular administration.

In some embodiments of the methods described herein, when the aminoglycoside antibiotic is tobramycin, administration is via parenteral administration, including, for example, intramuscular and intravenous injection. Tobramycin can be detected in tissues and body fluids after parenteral administration.

In some embodiments, when the aminoglycoside antibiotic is netilmicin, administration is by injection or infusion.

In some embodiments, when the aminoglycoside antibiotic is arbekacin, administration is via parenteral administration, such as intramuscular or intravenous administration. Normal duration of IM or IV arbekacin aminoglycoside antibiotic therapy is 7-10 days, although a longer duration can be necessary in some cases.

In some embodiments, when the aminoglycoside antibiotic is amikacin, administration is via intravenous or intramuscular route. There is currently no oral form available as amikacin is not absorbed orally. In some embodiments, liposomal amikacin for inhalation can be used for the treatment of respiratory diseases, such as, for example, cystic fibrosis, *Pseudomonas aeruginosa*, non-tubercular mycobacterial infections, and bronchiectasis. Side effects of amikacin are similar to other aminoglycosides. Kidney damage and hearing loss are the most important effects. Because of this potential, blood levels of the drug and markers of kidney function (creatinine) can be monitored. Moreover, doses of amikacin can be adjusted specifically based upon serum creatinine clearance in clinical settings.

In some embodiments, when the aminoglycoside antibiotic is neomycin, topical administration or oral administration is used. In preferred embodiments, neomycin is not administered intravenously, as neomycin is extremely nephrotoxic. In those embodiments, where neomycin is administered intravenously, the dose is less than 0.025 mg per dose.

In some embodiments, when the aminoglycoside antibiotic is framycetin, topical administration or oral administration is used. Framycetin has poor systemic absorption, and can be used in topical preparations for infections of the skin, nose, ears, and eyes, often in combination with other antibacterial drugs and corticosteroids. It can also be used for gastrointestinal infections, in some embodiments.

In some embodiments, when the aminoglycoside antibiotic is paromomycin, administration is via intramuscular injection or oral administration.

Pharmaceutical Formulations

Therapeutic formulations of aminoglycoside antibiotics and/or PMF stimulating compounds can be prepared, in some aspects, by mixing an aminoglycoside antibiotics and/or PMF stimulating compound having the desired degree of purity with one or more pharmaceutically acceptable carriers, excipients or stabilizers (Remington's Pharmaceutical Sciences 16th edition, Osol, A. Ed. (1980)), in the form of lyophilized formulations or aqueous solutions, either individually in some embodiments, or in combination, e.g., a therapeutic formulation comprising alone an effective amount of an aminoglycoside antibiotic and an effective amount of at least one PMF stimulating compound. Such therapeutic formulations of the aminoglycoside antibiotics and/or PMF stimulating compounds described herein include formulation into pharmaceutical compositions or pharmaceutical formulations for parenteral administration, e.g., intravenous; mucosal, e.g., intranasal; enteral, e.g., oral; topical, e.g., transdermal; ocular, or other mode of administration.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the activity of, carrying, or transporting the aminoglycoside antibiotics and/or PMF stimulating compounds, from one organ, or portion of the body, to another organ, or portion of the body.

Some non-limiting examples of acceptable carriers, excipients, or stabilizers that are nontoxic to recipients at the dosages and concentrations employed, include pH buffered solutions such as phosphate, citrate, and other organic acids; antioxidants, including ascorbic acid and methionine; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, HDL, LDL, or immunoglobulins; hydrophilic polymers, such as polyvinylpyrrolidone; amino acids such as glycine, glutamine, asparagine, histidine, arginine, or lysine; monosaccharides, disaccharides, and other carbohydrates including mannose, starches (corn starch or potato starch), or dextrins; cellulose, and its derivatives, such as sodium carboxymethyl cellulose, methylcellulose, ethyl cellulose, microcrystalline cellulose and cellulose acetate; chelating agents such as EDTA; sugars such as sucrose, glucose, lactose, mannitol, trehalose or sorbitol; salt-forming counter-ions such as sodium; metal complexes (e.g. Zn-protein complexes); glycols, such as propylene glycol; polyols, such as glycerin; esters, such as ethyl oleate and ethyl laurate; agar; buffering agents, such as magnesium hydroxide and aluminum hydroxide; alginic acid; pyrogen-free water; isotonic saline; Ringer's solution; polyesters, polycarbonates and/or polyanhydrides; C2-C12 alcohols, such as ethanol; powdered tragacanth; malt; and/or non-ionic surfactants such as TWEEN™, PLURONICS™ or polyethylene glycol (PEG); and/or other non-toxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments, therapeutic formulations or compositions comprising an aminoglycoside antibiotics and/or PMF stimulating compound comprises a pharmaceutically acceptable salt, typically, e.g., sodium chloride, and preferably at about physiological concentrations. Optionally, the formulations described herein can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

In some embodiments of the aspects described herein, an aminoglycoside antibiotic and/or PMF stimulating compound, can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (4) intravaginally or intrarectally, for example, as a pessary', cream or foam; (5) sublingually; (6) ocularly; (7) transdermally; (8) transmucosally; or (9) nasally. Additionally, an aminoglycoside antibiotic and/or PMF stimulating compound, can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquids such as suspensions (e.g., aqueous or non-aqueous liquid suspensions, oil-in-water emulsions, or water-in-oil liquid emulsions), solutions, and elixirs; and sterile solids (e.g., crystalline or amorphous solids) that can be reconstituted to provide liquid dosage forms.

In some embodiments, parenteral dosage forms of the compositions comprising an aminoglycoside antibiotic and/or PMF stimulating compound, can be administered to a subject with a chronic infection or at risk for chronic infection by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, controlled-release parenteral dosage forms, and emulsions.

Suitable vehicles that can be used to provide parenteral dosage forms described herein are well known to those skilled in the art. It is understood by one of ordinary skill in the art, that much higher concentrations of the PMF stimulating compounds, such as glucose, must be provided in any therapeutic formulation, than is normally found when the compound is present as part of a vehicle in a dosage form. Examples of such vehicles include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Topical dosage forms of the aminoglycoside antibiotics and/or PMF stimulating compounds, are also provided in some embodiments, and include, but are not limited to, creams, lotions, ointments, gels, shampoos, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990). and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer an aminoglycoside antibiotic and/or PMF stimulating compound, include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466.465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms of the aminoglycoside antibiotics and/or PMF stimulating compounds described herein are well known to those skilled in the pharmaceutical arts, and depend on the particular tissue or organ to which a given pharmaceutical composition or dosage form will be applied. In addition, depending on the specific tissue to be treated, additional components may be used prior to, in conjunction with, or subsequent to treatment with an aminoglycoside antibiotic and/or PMF stimulating compound. For example, penetration enhancers can be used to assist in delivering the active ingredients to or across the tissue.

In some embodiments, the compositions comprising an aminoglycoside antibiotic and/or PMF stimulating compound, are formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Due to their ease of administration, tablets and capsules represent the most advantageous solid oral dosage unit forms, in which case solid pharmaceutical excipients are used. If desired, tablets can be coated by standard aqueous or nonaqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. In some embodiments, oral dosage forms are not used for the aminoglycoside antibiotic.

Typical oral dosage forms of the compositions comprising an aminoglycoside antibiotic and/or PMF stimulating compound are prepared by combining the pharmaceutically acceptable salt of an aminoglycoside antibiotic and/or PMF stimulating compound, in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Binders suitable for use in the pharmaceutical formulations described herein include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical formulations described herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions described herein is typically present in from about 50 to about 99 weight percent of the pharmaceutical composition.

Disintegrants are used in the oral pharmaceutical formulations described herein to provide tablets that disintegrate when exposed to an aqueous environment. A sufficient amount of disintegrant that is neither too little nor too much to detrimentally alter the release of the active ingredient(s) should be used to form solid oral dosage forms of the aminoglycoside antibiotics and/or PMF stimulating compounds described herein. The amount of disintegrant used varies based upon the type of formulation, and is readily discernible to those of ordinary skill in the art. Disintegrants that can be used to form oral pharmaceutical formulations include, but are not limited to, agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form oral pharmaceutical formulations of the aminoglycoside antibiotics and/or PMF stimulating compounds described herein, include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL® 200, manufactured by W. R. Grace Co. of Baltimore, Md.), a coagulated aerosol of synthetic silica (marketed by Degussa Co. of Piano, Tex.), CAB-O-SIL® (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

In other embodiments, lactose-free pharmaceutical formulations and dosage forms are provided, wherein such compositions preferably contain little, if any, lactose or other mono- or di-saccharides. As used herein, the term "lactose-free" means that the amount of lactose present, if any, is insufficient to substantially increase the degradation rate of an active ingredient. Lactose-free compositions of the disclosure can comprise excipients which are well known in the art and are listed in the USP (XXI)/NF (XVI), which is incorporated herein by reference.

The oral formulations of the aminoglycoside antibiotics and/or PMF stimulating compound, further encompass, in some embodiments, anhydrous pharmaceutical compositions and dosage forms comprising the aminoglycoside antibiotics and/or PMF stimulating compounds described herein as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Anhydrous pharmaceutical compositions and dosage forms described herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. Anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

An aminoglycoside antibiotic and/or PMF stimulating compound can, in some embodiments of the methods described herein, be administered directly to the airways in the form of an aerosol or by nebulization. Accordingly, for use as aerosols, in some embodiments, an aminoglycoside antibiotic and/or PMF stimulating compound, can be packaged in a pressurized aerosol container together with suitable propellants, for example, hydrocarbon propellants like propane, butane, or isobutane with conventional adjuvants. In other embodiments, the aminoglycoside antibiotic and/or PMF stimulating compoundcan be administered in a non-pressurized form such as in a nebulizer or atomizer.

The term "nebulization" is well known in the art to include reducing liquid to a fine spray. Preferably, by such nebulization small liquid droplets of uniform size are produced from a larger body of liquid in a controlled manner. Nebulization can be achieved by any suitable means, including by using many nebulizers known and marketed today. As is well known, any suitable gas can be used to apply pressure during the nebulization, with preferred gases being those which are chemically inert to the aminoglycoside antibiotics and/or PMF stimulating compounds described herein. Exemplary gases include, but are not limited to, nitrogen, argon or helium.

In other embodiments, an aminoglycoside antibiotic and/or PMF stimulating compound, can be administered directly to the airways in the form of a dry powder. For use as a dry powder, an aminoglycoside antibiotic and/or PMF stimulating compound can be administered by use of an inhaler. Exemplary inhalers include metered dose inhalers and dry powdered inhalers.

Suitable powder compositions include, by way of illustration, powdered preparations of an aminoglycoside antibiotic and/or PMF stimulating compound, thoroughly intermixed with lactose, or other inert powders acceptable for, e.g., intrabronchial administration. The powder compositions can be administered via an aerosol dispenser or encased in a breakable capsule which may be inserted by the subject into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic an diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug. Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

In some embodiments, the active ingredients of the formulations comprising aminoglycoside antibiotics and/or PMF stimulating compounds described herein, can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments of these aspects, the aminoglycoside antibiotics and/or PMF stimulating compounds, can be administered to a subject by controlled- or delayed-release means. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. (Kim, Cherng-ju, Controlled Release Dosage Form Design, 2 (Technomic Publishing, Lancaster, Pa.: 2000)). Controlled-release formulations can be used to control, for example, an aminoglycoside antibiotic's onset of action, duration of action, plasma levels within the therapeutic window, and peak blood levels. In particular, controlled- or extended-release dosage forms or formulations can be used to ensure that the maximum effectiveness of the aminoglycoside antibiotic and/or PMF stimulating compound, is achieved while minimizing potential adverse effects and safety concerns, which can occur both from under-dosing a drug (i.e., going below the minimum therapeutic levels) as well as exceeding the toxicity level for the drug.

A variety of known controlled- or extended-release dosage forms, formulations, and devices can be adapted for use with the aminoglycoside antibiotics and/or PMF stimulating compound described herein Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated ins entirety herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, DUOLITE® A568 and DUOLITE® AP143 (Rohm & Haas, Spring House, Pa. USA).

In some embodiments of the aspects, the aminoglycoside antibiotics and/or PMF stimulating compounds for use in the various therapeutic formulations and compositions, and methods thereof, described herein, are administered to a subject by sustained release or in pulses. Pulse therapy is not a form of discontinuous administration of the same amount of a composition over time, but comprises administration of the same dose of the composition at a reduced frequency or administration of reduced doses. Sustained release or pulse administrations are particularly preferred in chronic conditions, as each pulse dose can be reduced and the total amount of a compound, such as, for example, an aminoglycoside antibiotic administered over the course of treatment to the patient is minimized.

The interval between pulses, when necessary, can be determined by one of ordinary skill in the art. Often, the interval between pulses can be calculated by administering another dose of the composition when the composition or the active component of the composition is no longer detectable in the subject prior to delivery of the next pulse. Intervals can also be calculated from the in vivo half-life of the composition. Intervals may be calculated as greater than the in vivo half-life, or 2, 3, 4, 5 and even 10 times greater the composition half-life. Various methods and apparatus for pulsing compositions by infusion or other forms of delivery to the patient are disclosed in U.S. Pat. Nos. 4,747,825; 4,723,958; 4,948,592; 4,965,251 and 5,403,590.

In some embodiments, sustained-release preparations comprising the aminoglycoside antibiotics and/or PMF stimulating compounds, can be prepared. Suitable examples of sustained-release preparations include semipermeable matrices of solid hydrophobic polymers containing the inhibitor, in which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(−)-3-hydroxybutyric acid.

The formulations comprising the aminoglycoside antibiotics and/or PMF stimulating compounds described herein, to be used for in vivo administration are preferably sterile. This is readily accomplished by filtration through, for example, sterile filtration membranes, and other methods known to one of skill in the art.

The following exemplary methods were used to demonstrate proton-motive force inducing metabolites potentiated aminoglycosides against bacterial persisters, and can be used, for example to identify addition PMF stimulating coumpunds and adjuvants for use in the methods and compositions described herein.

For *E. coli* (K12 EMG2 strain) persister assays, as described herein, samples were grown to stationary phase in Luria-bertani (LB) broth. Cultures were then treated for 4 hours with 5 μg/mL ofloxacin. Previous work has demonstrated that treatment under these conditions for 3 hours eliminates all susceptible non-persister cells. We verified that remaining cells were persisters by increasing the amount of added ofloxacin to 20 μg/mL and noted no further decrease in viability. Persistence was further verified by demonstrating that none of the bactericidal antibiotics used in this study (ofloxacin, ampicillin, and gentamicin) caused killing of cells when added without metabolites. Samples were then washed with 10 mL 1× filtered PBS and re-suspended in M9 minimal media. Metabolites (Glucose, mannitol, fructose, and pyruvate) and aminoglycoside antibiotics (10 μg/mL gentamicin, 50 μg/mL streptomycin, and 30 μg/mL kanamycin) were added, and samples were incubated at 37° C., 300 RPM, and 80% humidity. Resuspension of samples in defined minimal media allowed precise and specific testing of the effect of different metabolites on persister viability, without the possible confounding factors that a more complex media would present. For *S. aureus* persister (ATCC 25923 strain) experiments, cells were grown at 37° C. and 300 RPM in LB broth to an OD600 of 0.3. Cells were then diluted 1:1000 in 25 mL LB and grown for 16 hours at 37° C. and 300 RPM in 250 mL flasks. Cultures were treated with carbon source and antibiotic. Previous work has shown that, approximately all, stationary phase *S. aureus* cells are persistent.

At specified time points, 10 μL aliquots of samples were removed, serially diluted, and spot-plated onto LB agar plates to determine colony forming units/mL (CFU/mL). Only dilutions that yielded between 10-100 colonies were counted. Survival was determined by dividing a replicate's CFU/mL at each time point by the initial CFU/mL for the replicate.

The following methods were used to demonstrate proton-motive force inducing metabolites potentiated aminoglycosides against persistent bacteria under anaerobic conditions, and can be used, for example to identify addition PMF stimulating compounds and adjuvants for use in the methods and compositions described herein.

*E. coli* cultures were grown to an optical density (OD600) of 0.3, and then diluted 1:1000 in 25 mL anaerobic LB with 10 mM NaNO$_3$ and grown for 16 hours at 37° C., 200 RPM, 1.5-2.0% hydrogen, <50 ppm oxygen in 250 mL flasks. Cultures were then treated with metabolite (10 mM glucose, mannitol, and fructose) and aminoglycoside (10 μg/mL gentamicin) in the presence and absence of an additional 10 mM NaNO$_3$. The additional NaNO$_3$ was added to determine if increasing the concentration of the terminal electron acceptor, which boosts proton-motive force, increases aminoglycoside potentiation.

The following methods were used to demonstrate proton-motive force inducing metabolites potentiated aminoglycosides against bacterial biofilms:

Overnight cultures grown in LB were diluted 1:200 into pre-warmed LB which was then added to MBEC plates (Innovotech) at 150 μL per well. Plates were incubated at 35° C., 150 RPM for 24 hours, then pegs were washed in a microtiter plate with 200 μL 1×PBS per well. Pegs were then added to a microtiter plate containing 200 μL M9 minimal salts (for *E. coli*) or sterofiltered, stationary phase media (for *S. aureus*) plus metabolites (10 mM mannitol and fructose) and aminoglycoside antibiotic (10 μg/mL gentamicin). Plates were incubated at 35° C., 150 RPM for 4 hours, then pegs were washed twice in microtiter plates with 200 μL 1×PBS per well. To dislodge biofilm cells, pegs were placed in a microtiter plate with 145 μL 1×PBS per well and sonicated in water bath for 30 minutes at 40 kHz. Serial dilutions and spot plating were performed to determine viable CFU/peg. For determination of the dependence of *E. coli* biofilm elimination on pH, we carried out the above procedure in M9 salts buffered to appropriate pH with citric acid as opposed to KH$_2$PO$_4$, which is typically used for M9.

The following methods were used to demonstrate proton-motive force inducing metabolites potentiated aminoglycosides in a chronic urinary-tract infection model in mice:

Female Charles River Balb/C mice (weighing 22-26 g) received surgical implantation in the urinary tract of 6 mm PESO catheter tubing that had been incubated in cultures of uropathogenic *E. coli* for 24 hours to form biofilms. Forty-eight hours after surgery, mice received no treatment or twice-daily, intravenous treatment with gentamicin (1 mg/Kg) or mannitol (1.5 g/Kg) and gentamicin (1 mg/Kg) for three days. Seven to eight mice were included in each group. Twenty-four hours after the last treatment, catheter tubing was extracted to determine biofilm viability and kidneys were removed to determine bacterial load.

Some aspects and embodiments disclosed herein can be illustrated by, for example, any of the following numbered paragraphs:

1. A method for treating a chronic or persisting bacterial infection, the method comprising administering to a subject having or at risk for a chronic or persisting bacterial infection an effective amount of an aminoglycoside antibiotic and an effective amount of at least one proton motive force (PMF) stimulating compound as an adjuvant.

2. A method for treating a chronic or persisting bacterial infection, comprising: administering to a subject having a chronic or persisting bacterial infection and undergoing treatment with an aminoglycoside antibiotic, an effective amount of at least one proton motive force stimulating compound as an adjuvant.

3. The method of any one of paragraphs 1 or 2, wherein the aminoglycoside antibiotic is streptomycin, gentamicin, kanamycin A, or tobramycin.

4. The method of any one of paragraphs 1 or 2, wherein the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin 5. The method of any one of paragraphs 1-4, wherein the PMF stimulating compound is a compound that enters upper glycolysis in bacteria.

6. The method of any one of paragraphs 1-4, wherein the PMF stimulating compound is a sugar.

7. The method of paragraph 6, wherein the sugar is glucose, mannitol, fructose, or a combination thereof.

8. The method of any one of paragraphs 1-7, wherein the PMF stimulating compound is a glycolysis product of a sugar.

9. The method of paragraph 6, wherein the glycolysis product is pyruvate.

10. The method of any one of paragraphs 1-9, wherein the PMF stimulating compound is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

11. The method of any one of paragraphs 1 or 2, wherein the aminoglycoside antibiotic is gentamicin and the at least one PMF stimulating compound is mannitol.

12. The method of any one of paragraphs 1 or 2, wherein the aminoglycoside antibiotic is gentamicin and the at least one PMF stimulating compound is fructose.

13. The method of any one of paragraphs 1 or 2, wherein the aminoglycoside antibiotic is tobramycin and the at least one PMF stimulating compound is mannitol.

14. The method of any one of paragraphs 1-13, wherein the bacterial infection comprises one or more gram positive or gram negative organisms.

15. The method of paragraph 13, wherein the bacterial infection comprises one or more of *Escherichia coli* or *Staphylococcus aureus*.

16. The method of paragraph 13, wherein the bacterial infection comprises one or more of species of *Pseudomonas, Proteus, Serratia, Citrobacter, Enterobacter, Klebsiella, Pseudomonas, Acinetobacter*, or *Enterobacter*.

17. The method of any one of paragraphs 1-16, wherein the bacterial infection is a hospital-acquired infection.

18. The method of paragraph 17, wherein the hospital-acquired infection is caused by methicillin-resistant *Staphylococcus aureus* or multidrug resistant *Pseudomonas aeruginosa*.

19. The method of any one of paragraphs 1-18, wherein the bacterial infection is characterized by biofilm formation.

20. The method of any one of paragraphs 1-19, wherein the infection is recurrent.

21. The method of any one of paragraphs 1-20, wherein the subject having or at risk for a chronic or persisting infection has a urinary tract infection; infective endocarditis; an infection of the skin, nose, ears, and/or eyes; external burns; an infection associated with cystic fibrosis; a prosthetic valve infection; a native valve infection' an infection associated with endometritis; an infections associated with febrile neutropenia; an intraabdominal infections; meningitis; an infections associated with osteomyelitis; an infection associated with pelvic inflammatory disease; an infection associated with peritonitis; an infection associated with pneumonia; an infections associated with pyelonephritis; an infection associated with skin or soft tissue; an infection associated with surgery, or an infection associated with tularemia.

22. The method of any one of paragraphs 1-21, wherein the subject having or at risk for a chronic or persisting infection is an immunocompromised subject.

23. The method of paragraph 22, wherein the immunocompromised subject is Human Immunodeficiency Virus-positive; a subject with cystic fibrosis; or a subject having chronic obstructive pulmonary disease.

24. The method of any one of paragraphs 1-23, wherein the subject having or at risk for a chronic or persisting infection has had, is having, or will have an invasive medical procedure.

25. The method of any one of paragraphs 1-24, wherein the subject having or at risk for a chronic or persisting infection has an in-dwelling medical device.

26. The method of any one of paragraphs 1-25, wherein the aminoglycoside antibiotic and PMF stimulating compound are administered topically.

27. The method of any one of paragraphs 1-26, wherein the aminoglycoside antibiotic and PMF stimulating compound are administered intravenously.

28. The method of any one of paragraphs 1-27, wherein the aminoglycoside antibiotic and PMF stimulating compound are administered intramuscularly.

29. The method of any one of paragraphs 1-28, wherein the aminoglycoside antibiotic is not administered via oral administration.

30. A method of inhibiting or delaying biofilm formation or colonization on a surface, the method comprising contacting a surface with an effective amount of an aminoglycoside antibiotic and an effective amount one or more PMF stimulating compounds 31. The method of paragraph 30, wherein the aminoglycoside antibiotic is streptomycin, gentamicin, kanamycin A, or tobramycin.

32. The method of paragraph 30, wherein the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin 33. The method of any one of paragraphs 30-32, wherein the one or more PMF stimulating compounds is a compound that enters upper glycolysis in bacteria.

34. The method of any one of paragraphs 30-33, wherein the one or more PMF stimulating compounds is a sugar.

35. The method of paragraph 34, wherein the sugar is glucose, mannitol, fructose, or a combination thereof.

36. The method of any one of paragraphs 30-35, wherein the one or more PMF stimulating compounds is a glycolysis product of a sugar.

37. The method of paragraph 36, wherein the glycolysis product is pyruvate.

38. The method of any one of paragraphs 30-37, wherein the one or more PMF stimulating compounds is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

39. The method of paragraph 30, wherein the aminoglycoside antibiotic is gentamicin and the one or more PMF stimulating compounds is mannitol.

40. The method of paragraph 30, wherein the aminoglycoside antibiotic is gentamicin and the one or more PMF stimulating compounds is fructose.

41. The method of any one of paragraphs 1 or 2, wherein the aminoglycoside antibiotic is tobramycin and the one or more PMF stimulating compounds is mannitol.

42. The method of any one of paragraphs 30-41, wherein the biofilm comprises one or more gram positive or gram negative organisms.

43. The method of any one of paragraphs 30-42, wherein the surface is a surface of an in-dwelling medical device.

44. The use of an aminoglycoside antibiotic and one or more proton motive force (PMF) stimulating compounds for treating a chronic infection.

45. The use of one or more proton motive force (PMF) stimulating compounds for treating a chronic infection in a subject administered an aminoglycoside antibiotic.

46. The use of paragraphs 44 or 45, wherein the aminoglycoside antibiotic is streptomycin, gentamicin, kanamycin A, or tobramycin.

47. The use of any one of paragraphs 37-39, wherein the aminoglycoside antibiotic is neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or paromomycinlividomycin 48. The use of any one of paragraphs 44-47, wherein the one or more PMF stimulating compounds is a compound that enters upper glycolysis in bacteria.

49. The use of any one of paragraphs 44-48, wherein the one or more PMF stimulating compounds is a sugar.

50. The use of paragraph 49, wherein the sugar is glucose, mannitol, fructose, or a combination thereof.

51. The use of any one of paragraphs 44-50, wherein the one or more PMF stimulating compounds is a glycolysis product of a sugar.

52. The use of paragraph 51, wherein the glycolysis product is pyruvate.

53. The use of any one of paragraphs 44-52, wherein the one or more PMF stimulating compounds is lactate, glucosamine, sorbitol, n-acetyl glucosamine, n-acetyl muramic acid, maltose, galactosamine, trehaloseribose, arabinose, gluconate, glycerol, galactarate, analogs or derivatives thereof, or any combination thereof.

54. The use of any one of paragraphs 44-45, wherein the aminoglycoside antibiotic is gentamicin and the at least one PMF stimulating compound is mannitol.

55. The use of any one of paragraphs 44-45, wherein the aminoglycoside antibiotic is gentamicin and the at least one PMF stimulating compound is fructose.

56. The use of any one of paragraphs 44-45, wherein the aminoglycoside antibiotic is tobramycin and the one or more PMF stimulating compounds is mannitol.

57. The use of any one of paragraphs 44-56, wherein the chronic infection comprises one or more gram positive or gram negative organisms.

58. The use of paragraph 57, wherein the chronic infection comprises one or more of *Escherichia coli* or *Staphylococcus aureus*.

59. The use of paragraph 57, wherein the chronic infection comprises one or more of species of *Pseudomonas, Proteus, Serratia, Citrobacter, Enterobacter, Klebsiella, Pseudomonas, Acinetobacter*, or *Enterobacter*.

60. The use of any one of paragraphs 44-59, wherein the chronic infection is a hospital-acquired infection.

61. The use of paragraph 60, wherein the hospital-acquired infection is caused by methicillin-resistant *Staphylococcus aureus* or multidrug resistant *Pseudomonas aeruginosa*.

62. The use of any one of paragraphs 44-61, wherein the chronic infection is a urinary tract infection; infective endocarditis; an infection of the skin, nose, ears, and/or eyes; external burns; an infection associated with cystic fibrosis; a prosthetic valve infection; a native valve infection' an infection associated with endometritis; an infections associated with febrile neutropenia; an intraabdominal infections; meningitis; an infections associated with osteomyelitis; an infection associated with pelvic inflammatory disease; an infection associated with peritonitis; an infection associated with pneumonia; an infection associated with pyelonephritis; an infection associated with skin or soft tissue; an infection associated with surgery, or an infection associated with tularemia.

63. The use of any one of paragraphs 44-62, wherein the chronic infection is characterized by biofilm formation.

64. The use of any one of paragraphs 44-63, wherein the chronic infection is recurrent.

EXAMPLES

Bacterial persistence is a state in which a sub-population of dormant cells, or 'bacterial persisters,' tolerates antibiotic treatment[1-4]. Bacterial persisters have been implicated in biofilms and in chronic and recurrent infections[5-7]. Despite this clinical relevance, there are currently no viable means for eradicating persisters. As described herein, we show that specific metabolic stimuli enable the killing of both Gram-negative (*Escherichia coli*) and Gram-positive (*Staphylococcus aureus*) persisters with aminoglycosides. As demonstrated herein, this potentiation is aminoglycoside specific, does not rely on growth resumption and is effective in both aerobic and anaerobic conditions. It proceeds, in part, by the generation of a proton-motive force which facilitates aminoglycoside uptake. Our results described herein demonstrate that bacterial persisters, although dormant, are primed for metabolite uptake, central metabolism and respiration. We show that aminoglycosides can be used in combination with specific metabolites to treat, for example, *E. coli* and *S. aureus* biofilms. Furthermore, we demonstrate that this approach can improve the treatment of chronic infections in a mouse urinary tract infection model. This work establishes a strategy for eradicating bacterial persisters that is based on metabolism, and demonstrates the importance of the metabolic environment to antibiotic treatment.

Translation occurs at a reduced rate in bacterial persisters[2,8], indicating that they should be susceptible to aminoglycosides, which are ribosome-targeting bactericidal antibiotics[9-13]. However, aminoglycosides have weak activity against dormant bacteria, despite continued translation in these cells[14,15].

Figure 1A:
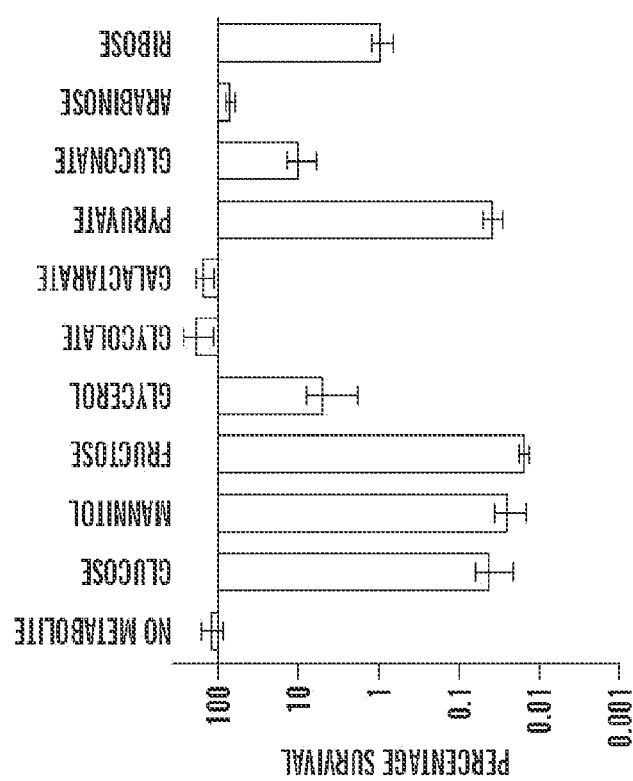

Given the dormancy of bacterial persisters and the known energy requirement for aminoglycoside activity[16], we tested whether metabolic stimulation could potentiate the efficacy of aminoglycosides against bacterial persisters. To test this, we screened metabolites for their ability to potentiate aminoglycosides against *E. coli* persisters. We selected carbon sources to maximize coverage of glycolysis, the pentose-phosphate pathway (PPP) and the Entner-Doudoroff pathway (EDP) (FIGS. 1A, 1B). Bacterial persisters were isolated (as described under "Methods"), re-suspended in minimal media supplemented with individual metabolites and then treated for 2 hours with the aminoglycoside gentamicin.

Figure 6A:
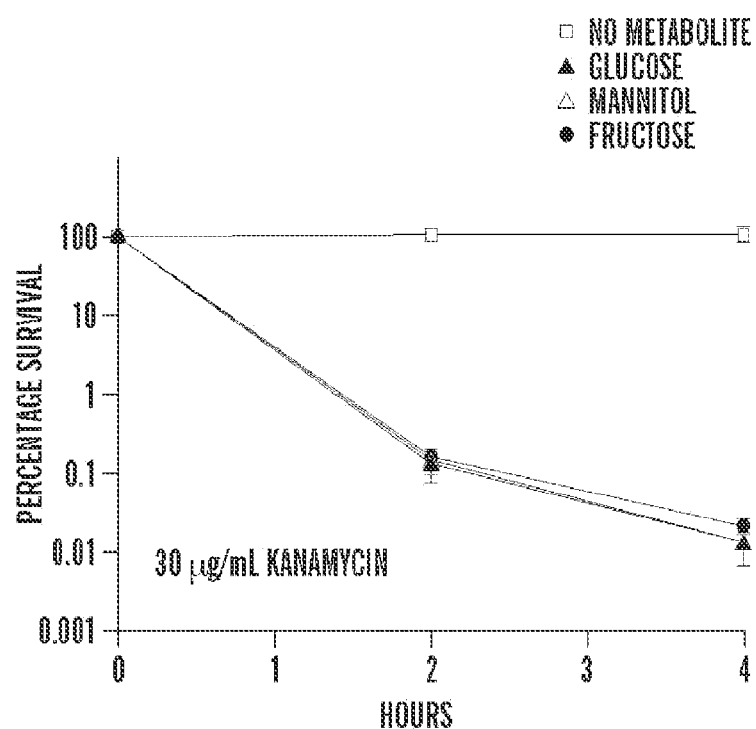
FIGS. 6A-6B demonstrate that Metabolite-enabled persister eradication is general to aminoglycosides. Percent survival of wild-type E. coli persisters treated with no metabolite, glucose, mannitol, and fructose, plus: 6A, 30 µg/mL kanamycin; or 6B, 50 µg/mL streptomycin FIGS. 7A-7J demonstrate metabolite potentiation of gentamicin activity and ability to induce growth in E. coli persisters. Persister cells were incubated for four hours in M9 minimal media plus carbon sources entering metabolism at specific points in glycolysis, the pentose-phosphate pathway, and the entner-douderoff pathway. Solid lines indicate persisters treated with carbon sources; dotted lines indicate persisters treated with 10 µg/mL gentamicin and carbon sources. In all plots, solid black lines indicate no treatment and dotted black lines indicate treatment with 10 µg/mL gentamicin. Plots 7A-7J show survival data for persisters in M9 plus the following carbon sources: 7A, 10 mM glucose; 7B, 10 mM mannitol; 7C, 10 mM fructose; 7D. 20 mM glycerol; 7E, 30 mM glycolate; 7F, 10 mM galactarate; 7G, 20 mM pyruvate; 7H, 10 mM gluconate; 7I, 12 mM arabinose; and 7J, 12 mM ribose.
Figure 6B:
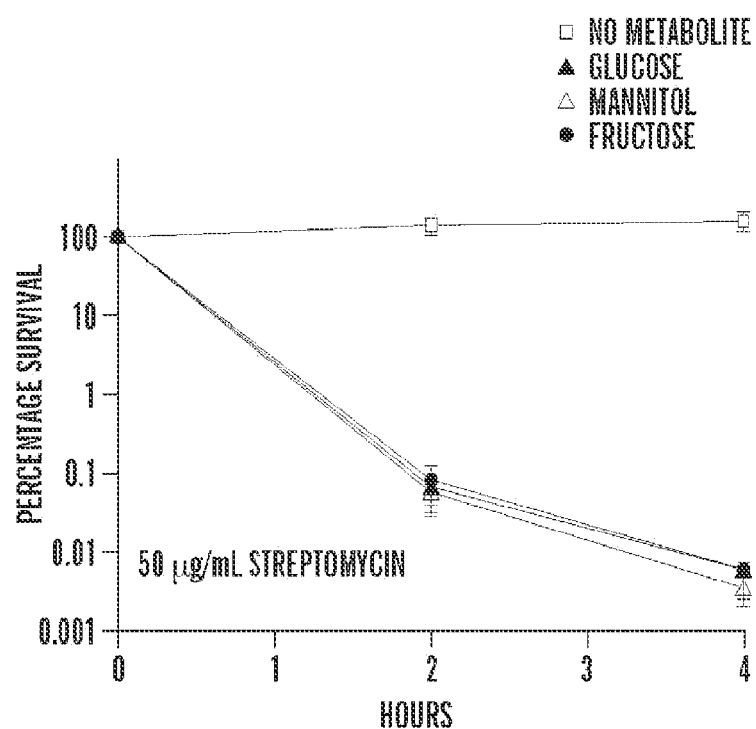
Figure 7D:
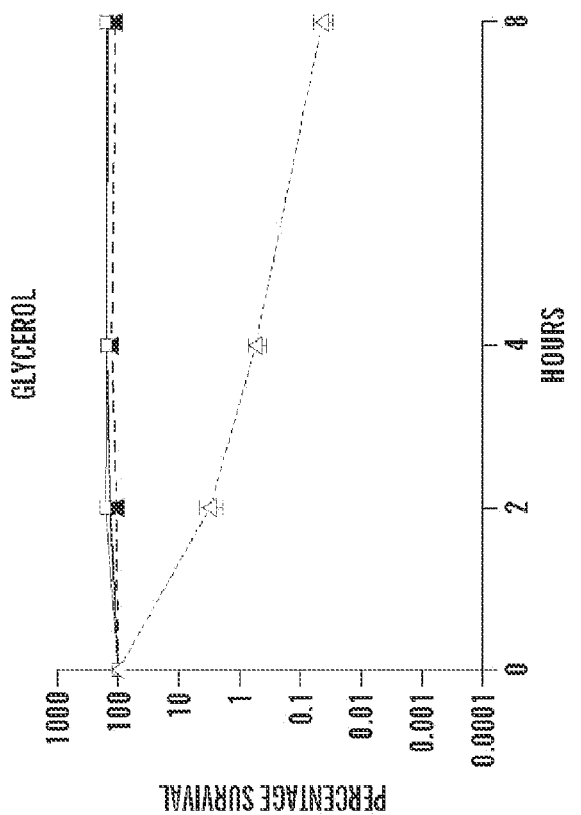
Figure 7C:
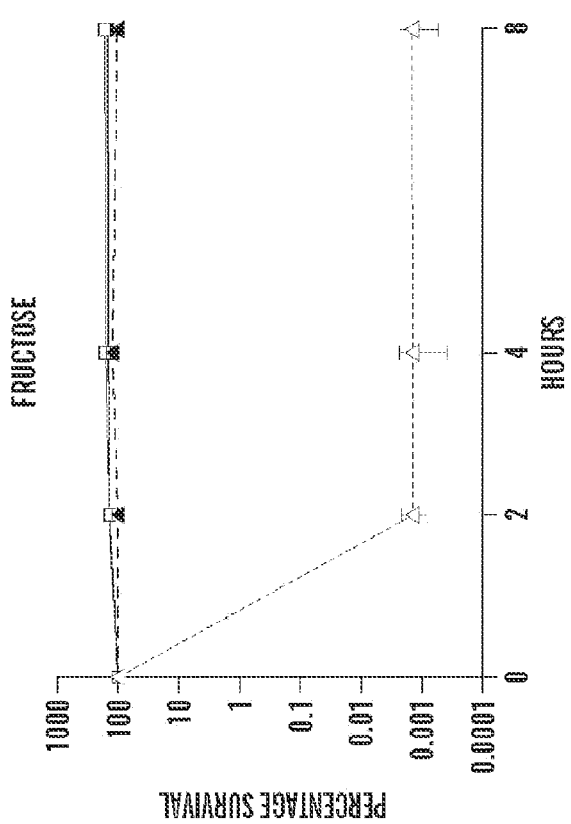
Figure 7J:
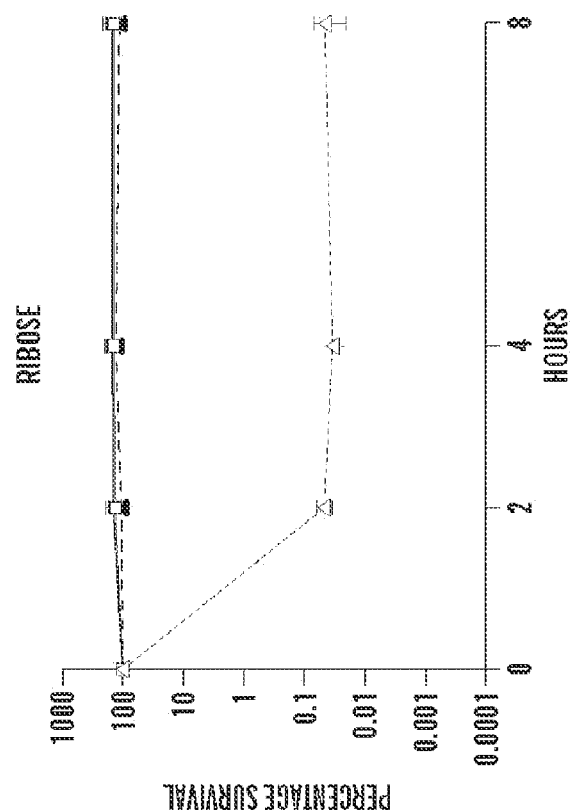
Figure 7I:
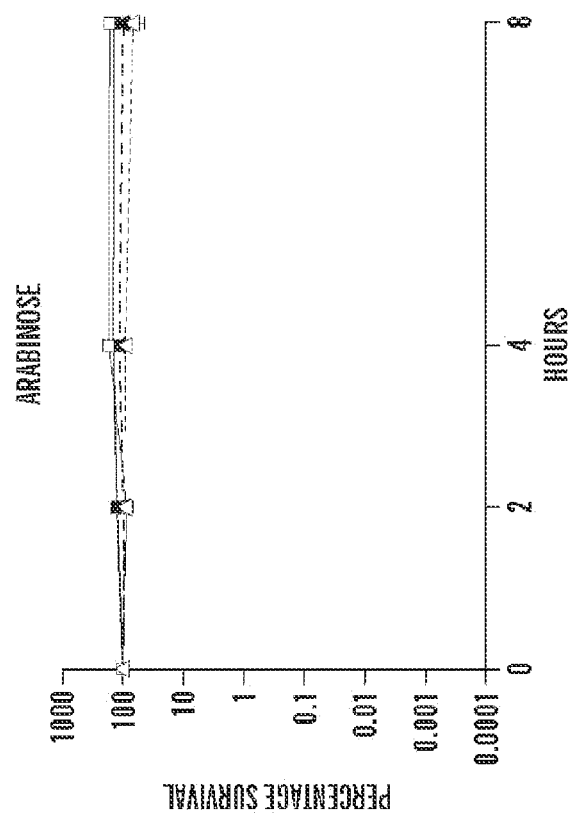
Figure 8H:
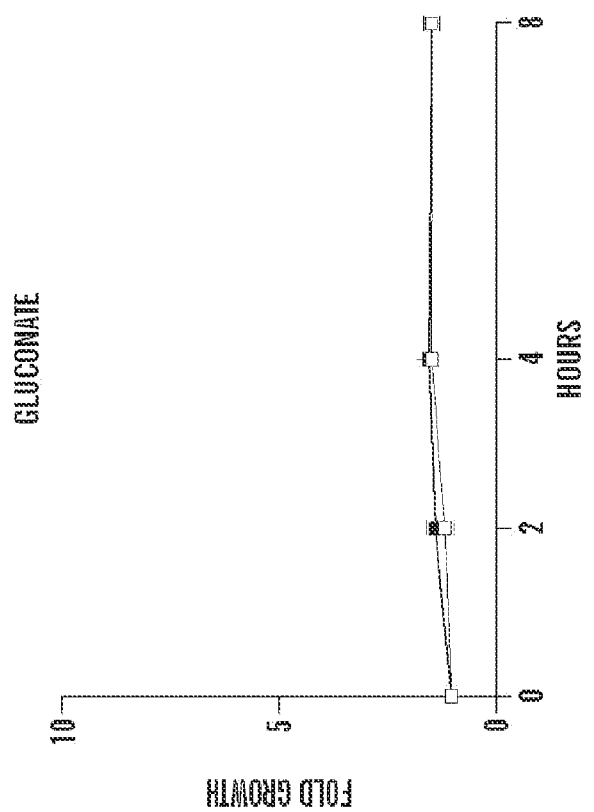
Figure 8G:
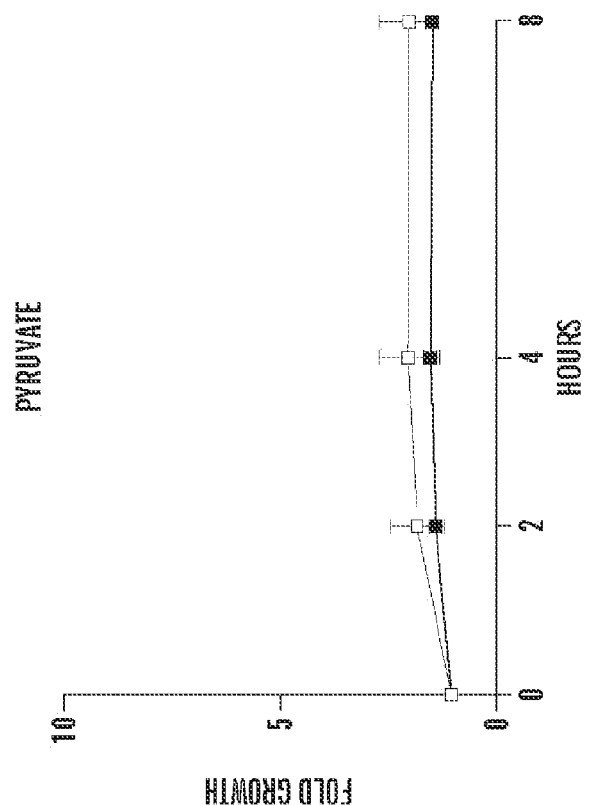
Figure 8J:
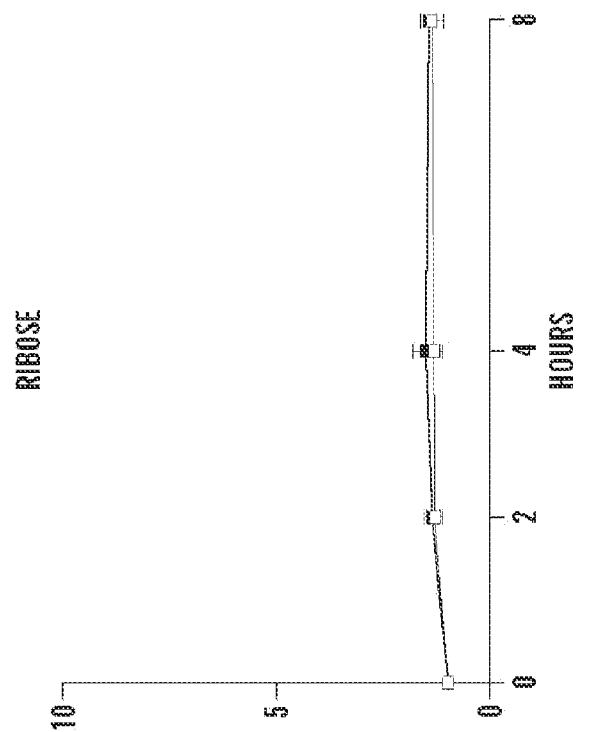
Figure 8I:
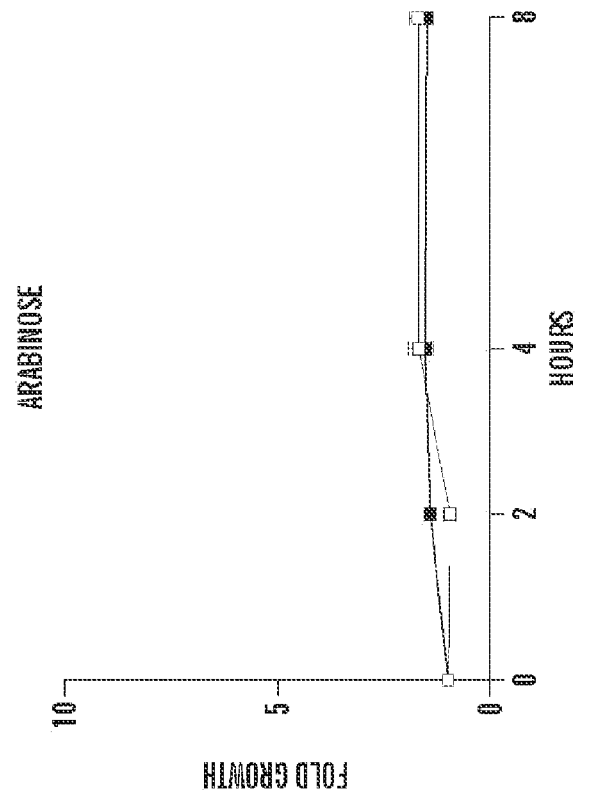
Figure 9A:
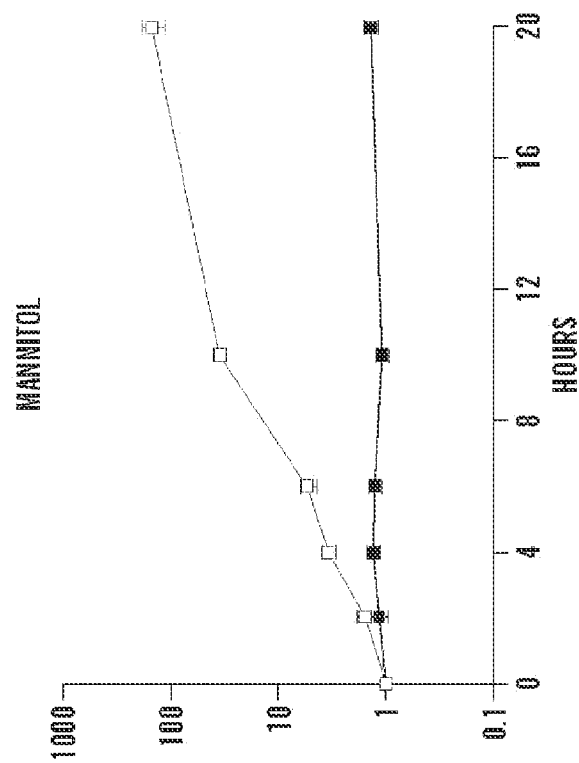
Figure 9B:
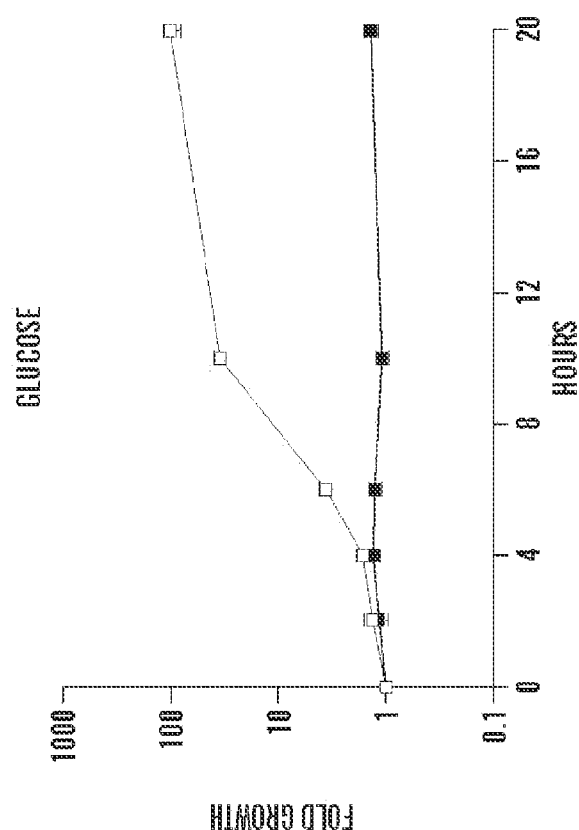
Figure 9D:
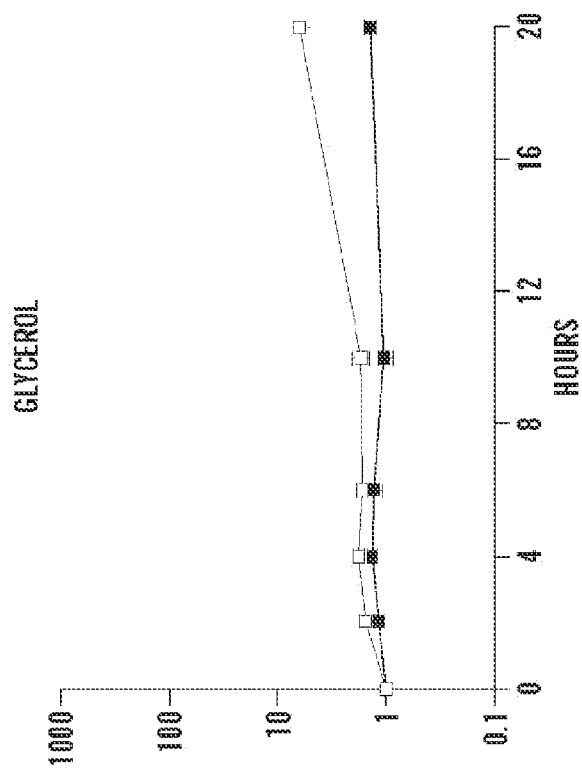
Figure 9C:
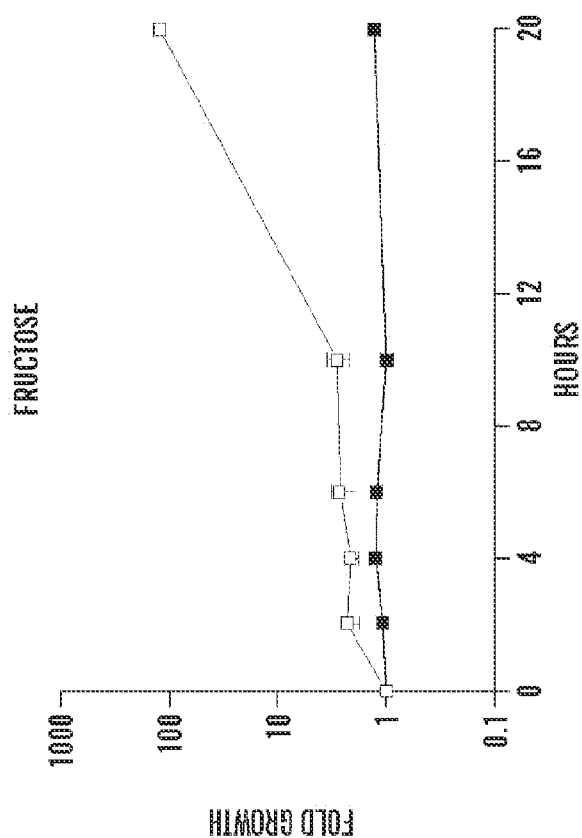
Figure 9F:
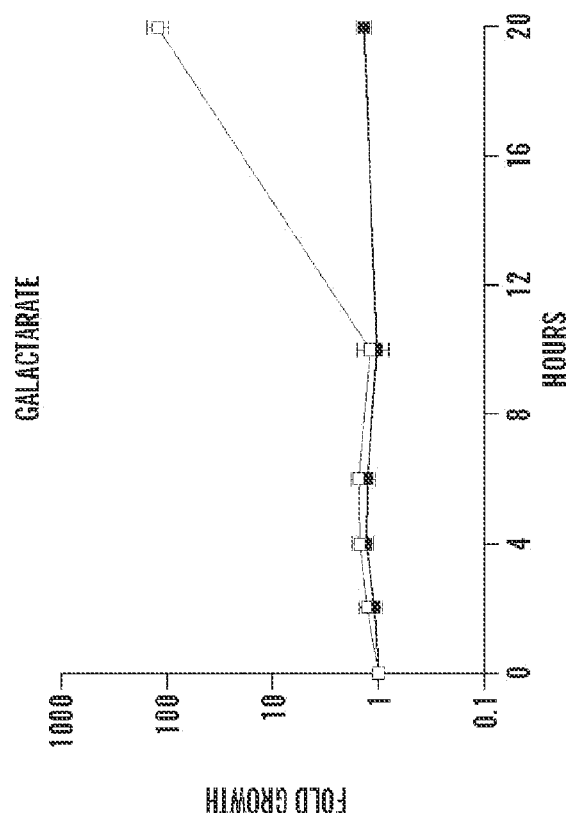
Figure 9E:
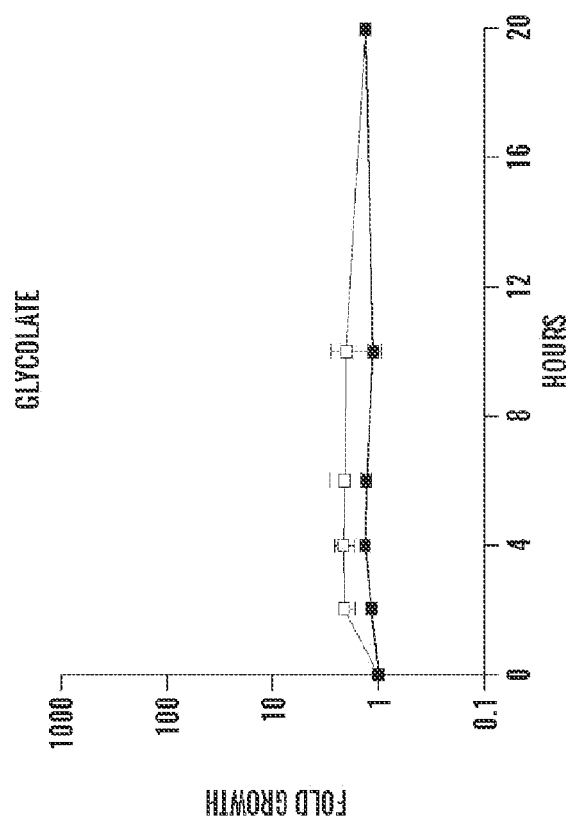
Figure 9J:
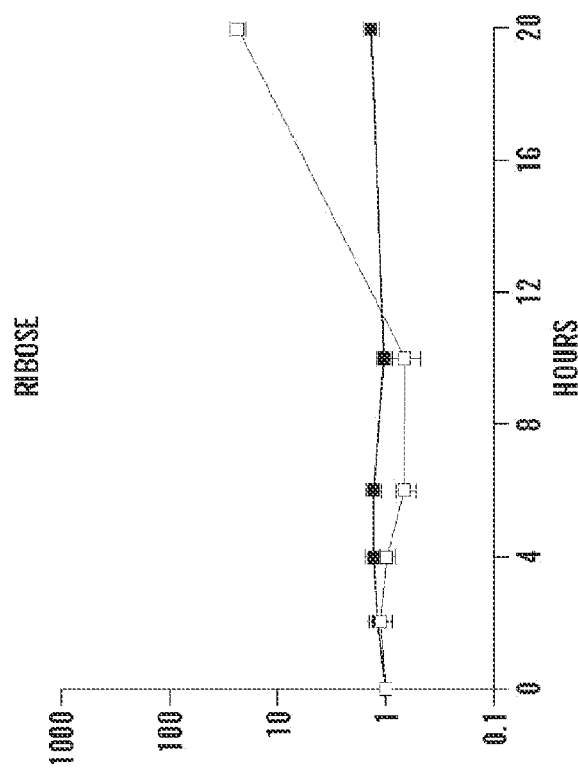
Figure 9I:
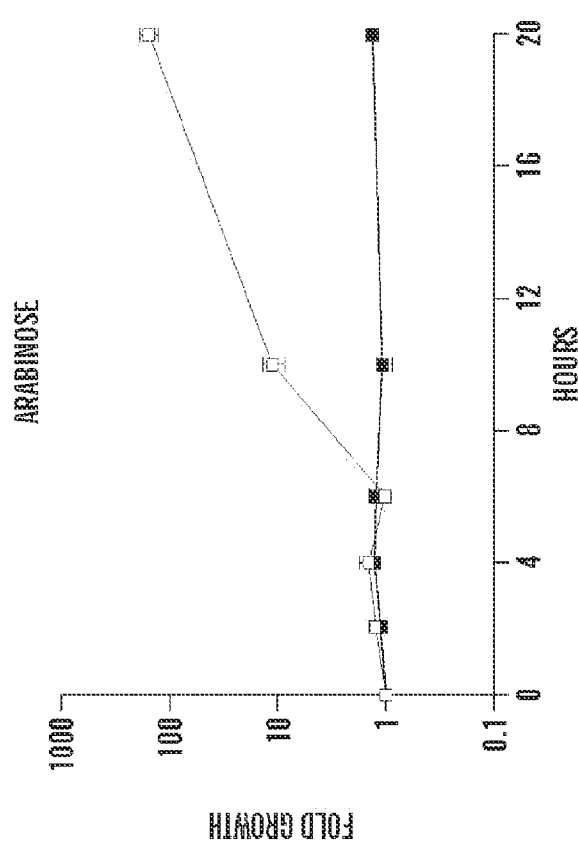
Figure 10B:
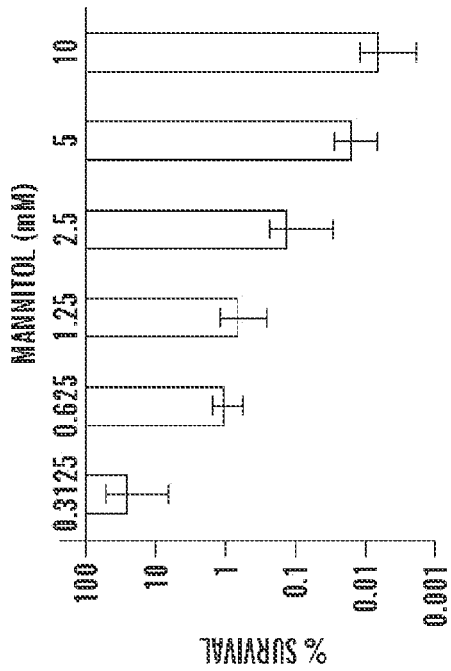
FIGS. 10A-10D demonstrate dependence of metabolite-enabled persister eradication on metabolite concentration. Persister cells were treated with 10 µg/mL gentamicin for four hours in M9 minimal media plus indicated concentrations of metabolites: 10A, glucose; 10B, mannitol; 10C fructose; and 10D, pyruvate.
Figure 10D:
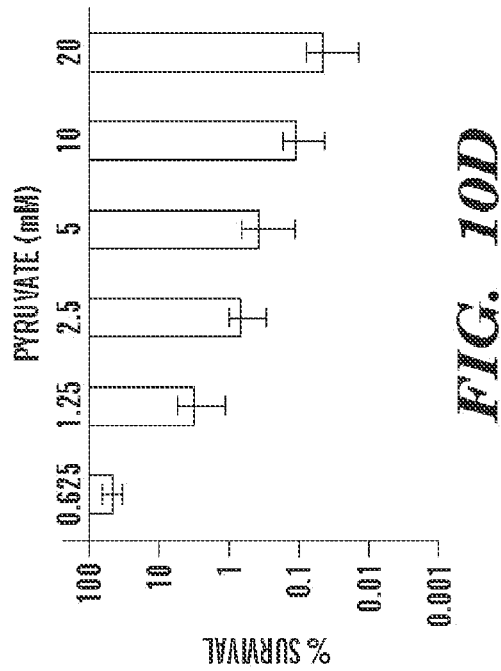
Figure 10A:
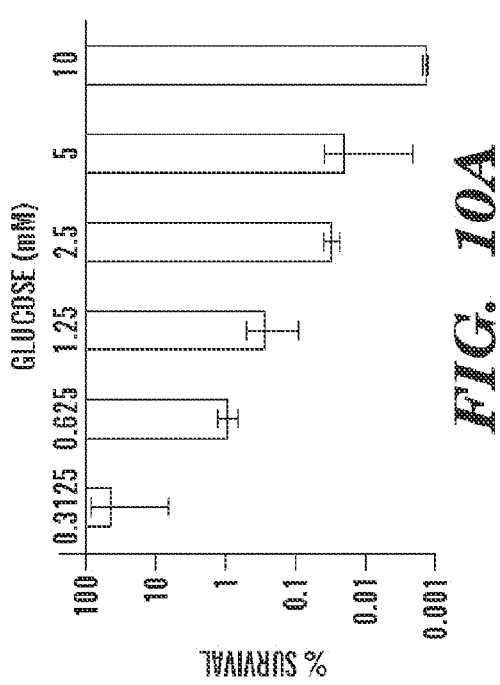
Figure 10C:
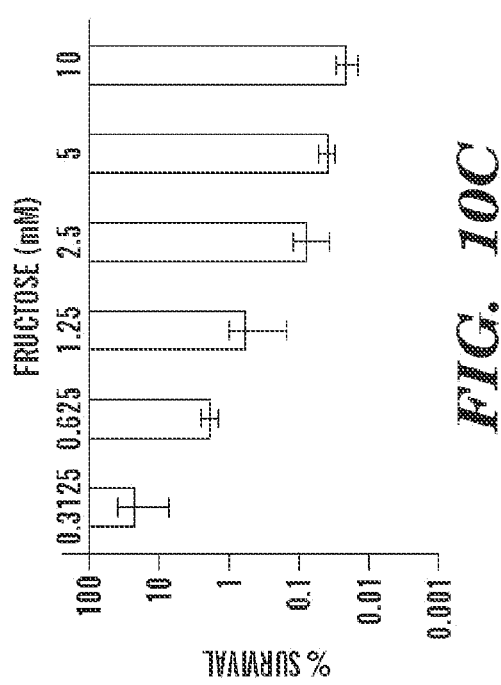
Figure 11:
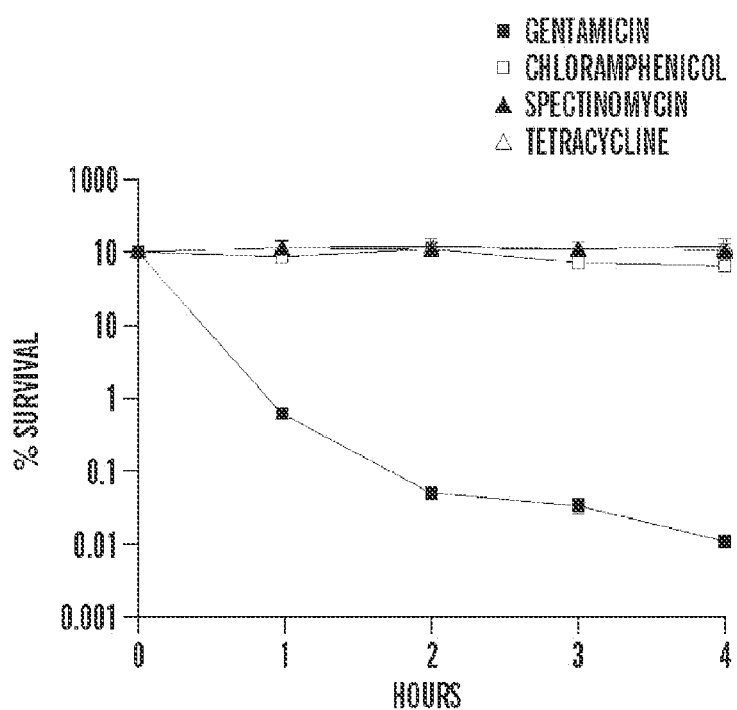
FIG. 11 demonstrates static ribosomal inhibitors do not cause metabolite-enabled killing of persistent E. coli. Percent survival of wild-type E. coli persisters after treatment with 10 mM mannitol and the following ribosomal inhibitors: 10 µg/mL gentamicin, 100 µg/mL spectinomycin, 50 µg/mL chloramphenicol, and 40 µg/mL tetracycline.
Figure 12:
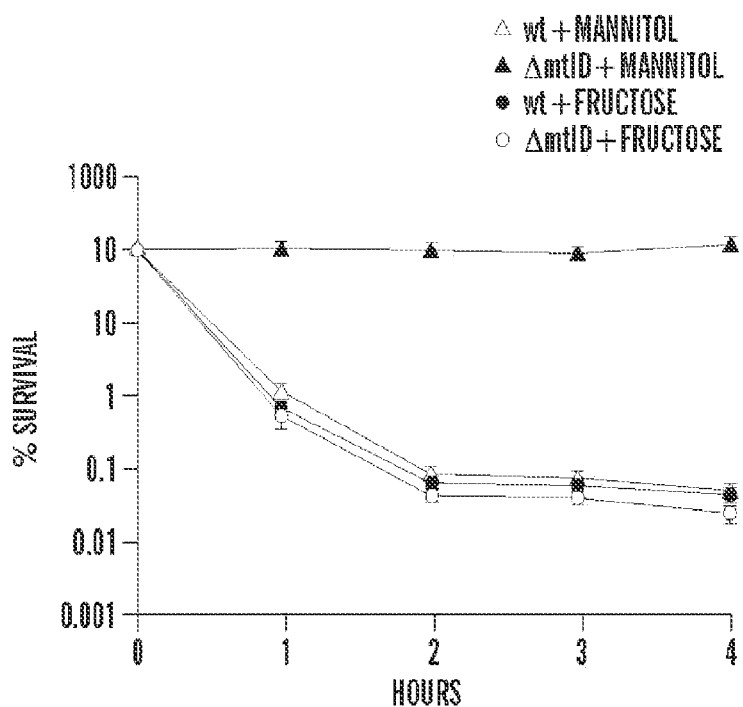
FIG. 12 demonstrates that metabolism of carbon source is required for metabolite-enabled potentiation of aminoglycosides. Survival of wild-type and ΔmtlD E. coli (EMG2) persisters treated with 10 µg/mL gentamicin plus 10 mM mannitol, or 10 mM fructose.
Figure 13F:
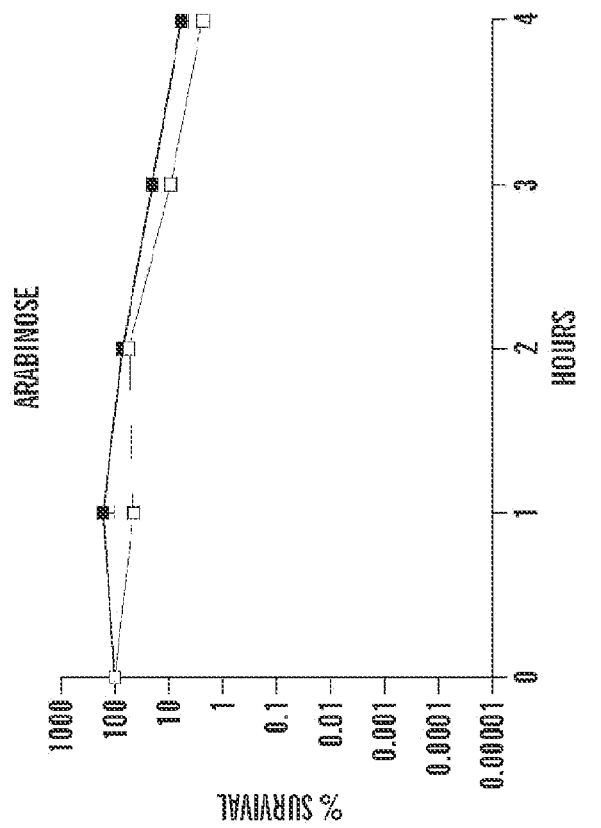
Figure 13E:
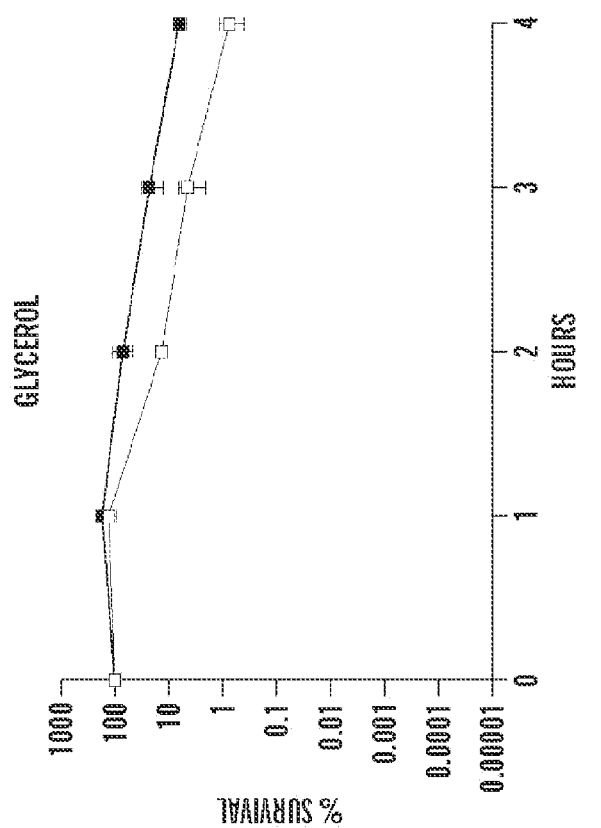

We determined that gentamicin was significantly potentiated against persisters by specific metabolic stimuli (FIGS. 1A, 1B). We demonstrated that metabolites that enter upper glycolysis (glucose, mannitol and fructose), as well as pyruvate, induced rapid killing of persisters by gentamicin, reducing persister viability by three orders of magnitude. In contrast, metabolites that enter lower glycolysis (except for pyruvate) caused little potentiation. Metabolites entering metabolism via the PPP or EDP (arabinose, ribose and gluconate) also showed low potentiation. No killing was observed in the control, demonstrating that the treated cells were persistent to gentamicin in the absence of an added metabolite. We verified that the metabolite-enabled eradication of persisters was general to the aminoglycoside class of antibiotics by testing kanamycin and streptomycin (FIGS. 6A-6B).

Figure 1D:
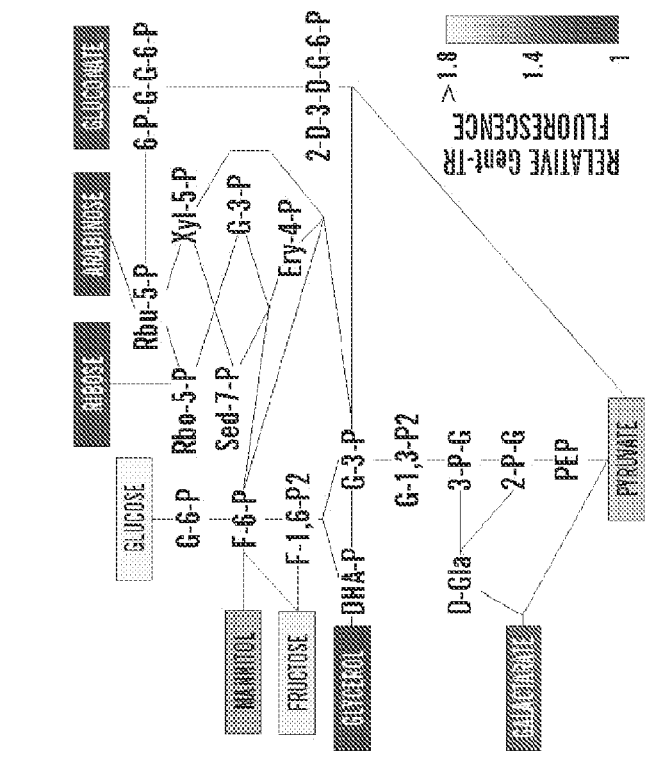
Figure 1C:
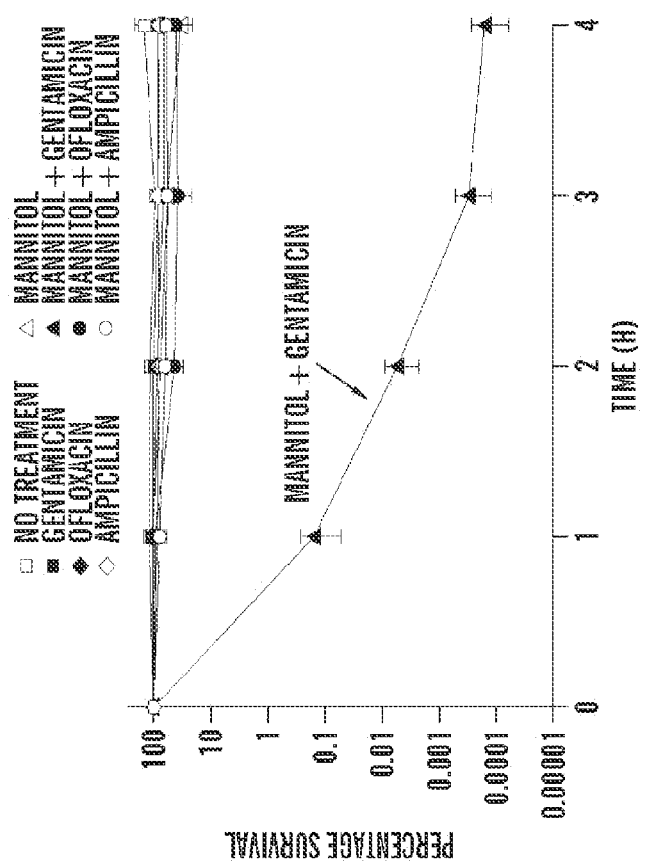

We considered that the potentiating metabolites might cause persisters to revert to normally growing cells, which would render them susceptible to quinolone (DNA-damaging) and β-lactam (cell-wall inhibiting) antibiotics. To test this, we treated bacterial persisters in the presence and absence of mannitol with a member of each of the three major classes of bactericidal antibiotics: aminoglycosides, quinolones and β-lactams. As seen in the metabolite screen, gentamicin rapidly eliminated metabolically stimulated bacterial persisters (FIG. 1C). However, neither the β-lactam ampicillin nor the quinolone ofloxacin showed appreciable killing of persisters in either the presence or the absence of mannitol. This shows that potentiation is aminoglycoside-specific and that cells were persistent to quinolones and β-lactams. It further indicates that metabolic stimuli under these conditions do not rapidly revert persisters to a growth state in which cell-wall synthesis and DNA synthesis are active. To explore this further, we tested the growth of bacterial persisters on the metabolites used for aminoglycoside potentiation and observed negligible growth of persisters 8 h after metabolite addition (FIGS. 7I-7J, FIGS. 8A-8J). Taken together, these data described herein indicate that the metabolic stimuli bolster a process that is specific to aminoglycosides and do not cause persisters to revert to normally growing cells.

Figure 14:
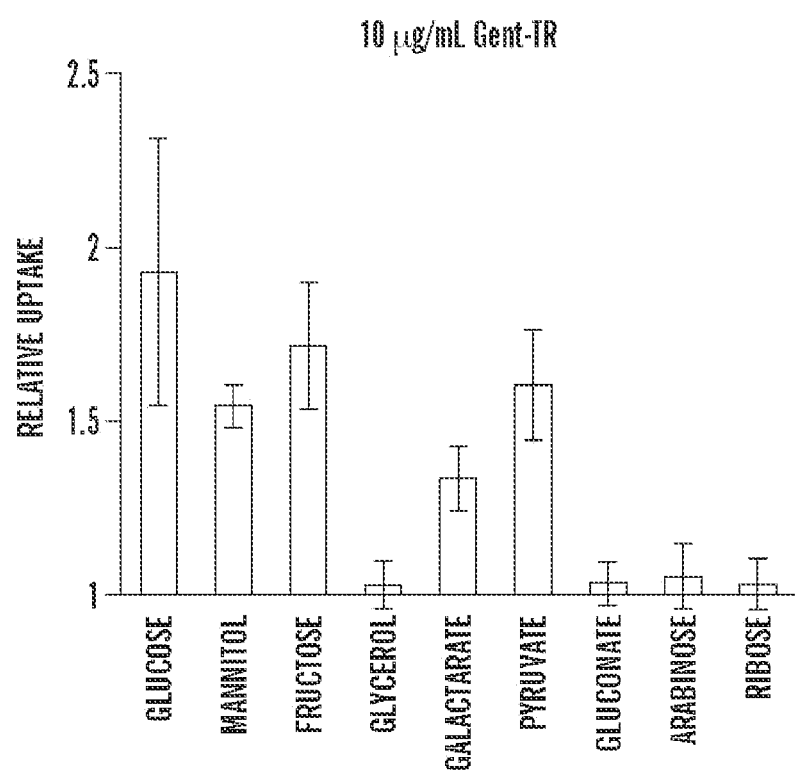
FIG. 14 demonstrates gentamicin uptake induced by carbon sources in stationary phase E. coli. Median uptake of 10 µg/mL gentamicin-Texas Red (Gent-TR) induced by 30 minutes of incubation on carbon sources. Median values were normalized by uptake in the no-carbon control. The normalized median values presented are the average of three independent experiments. Error bars signify the SEM of median values.
Figure 15E:
Figure 15F:
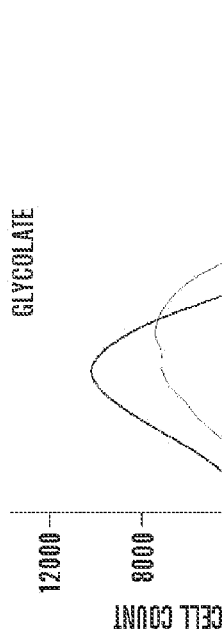
Figure 15G:
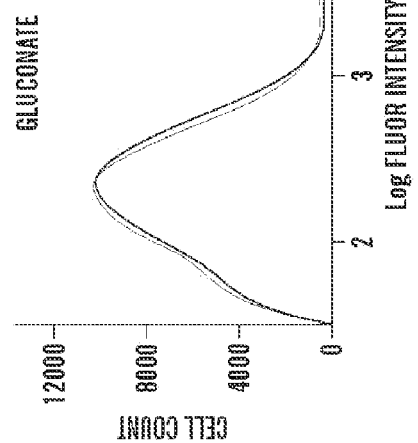
Figure 15H:
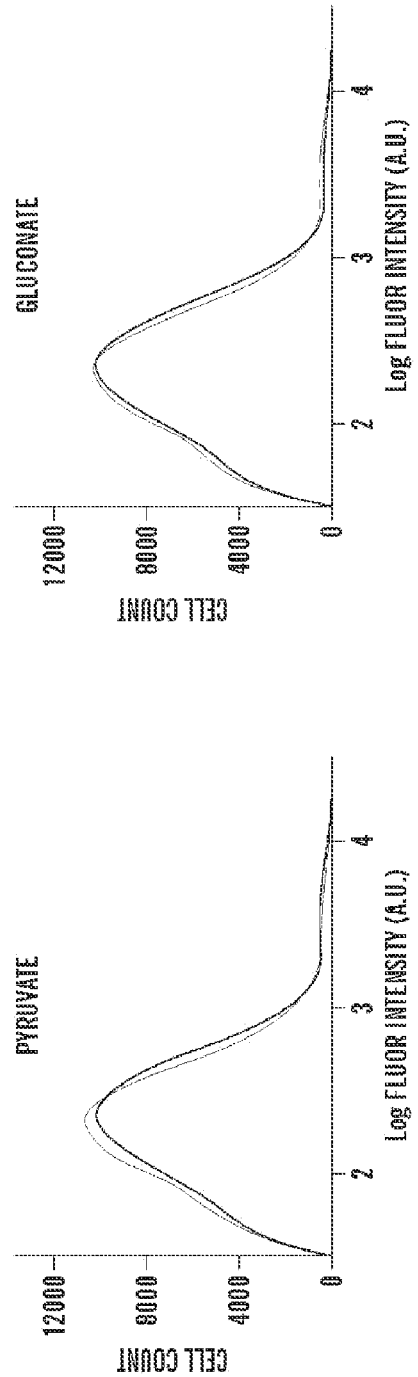
Figure 15J:
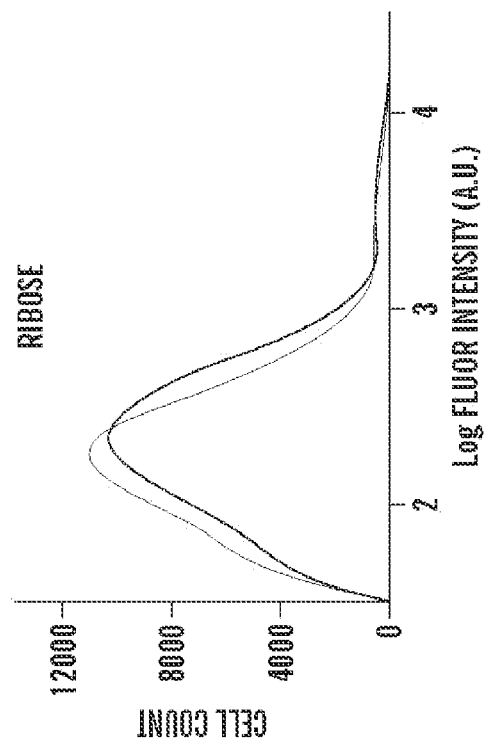
Figure 15I:
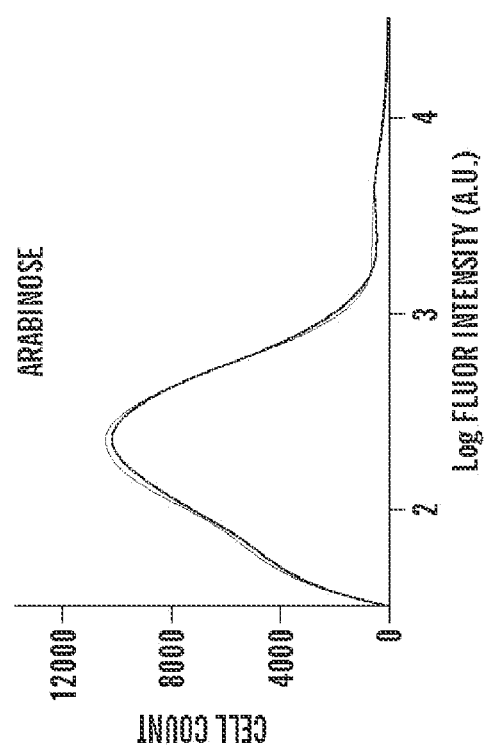

Given that aminoglycoside uptake is energy-dependent[16], we investigated whether the metabolic stimuli screened here could increase aminoglycoside uptake. We measured uptake by fluorescently labelling gentamicin with Texas red and analyzing cells by fluorescence-activated cell sorting (FACS). Cells were pre-incubated with metabolites for 30 min before a 5-min treatment with gentamicin-Texas red (FIG. 1D and FIG. 14). Metabolites that induced substantial killing by aminoglycosides also induced high levels of amino-glycoside uptake, indicating that the increased uptake was responsible for the killing. Furthermore, metabolites that caused low potentiation did not significantly increase aminoglycoside uptake.

Figure 2B:
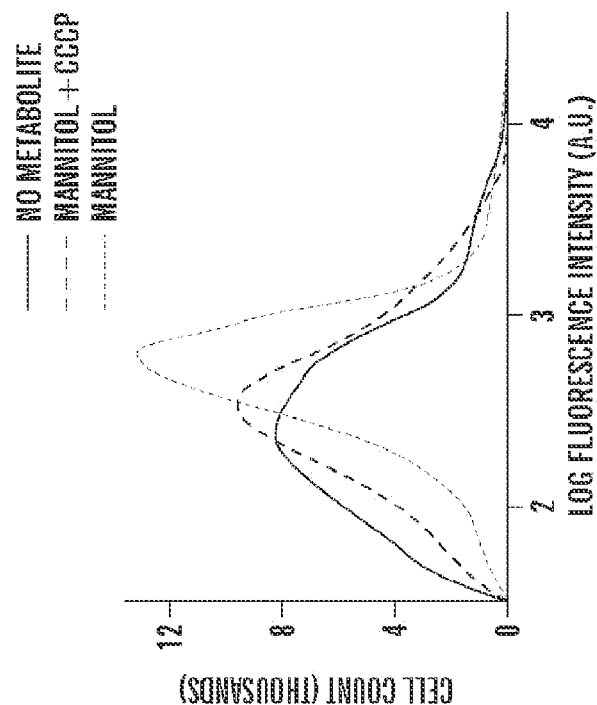
FIGS. 2A-2D demonstrate metabolite-enabled aminoglycoside uptake and bacterial killing requires PMF produced by the oxidative electron transport chain. 2A. Percentage survival of persisters after treatment with gentamicin plus uptake-potentiating metabolites with CCCP (dark grey bars) and without CCCP (light grey bars). 2B. Representative measurement of gentamicin-Texas red uptake by stationary-phase cells after incubation with no metabolite, mannitol or mannitol and CCCP (see also FIGS. 17A-17D). A.U., arbitrary units. 2C. Percentage survival of persisters in wild-type (WT) and cytochrome-inactivated strains after treatment with gentamicin plus mannitol (see also FIGS. 20A-20C). The presence (ticks) or absence (crosses) of functional complexes is indicated below test conditions. 2D. Percentage survival of persisters in wild-type and NADH-dehydrogenase-inactivated strains after treatment with gentamicin plus mannitol (see also FIGS. 23A-23C). The presence or absence of functional complexes is indicated as in 2C. Means s.e.m. are presented throughout (n≥3).
Figure 2A:
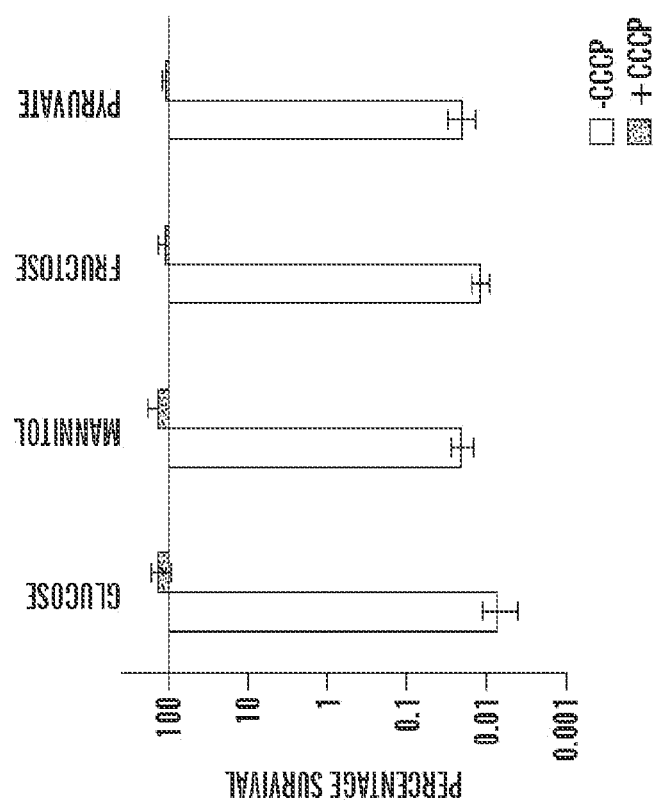
Figure 2C:
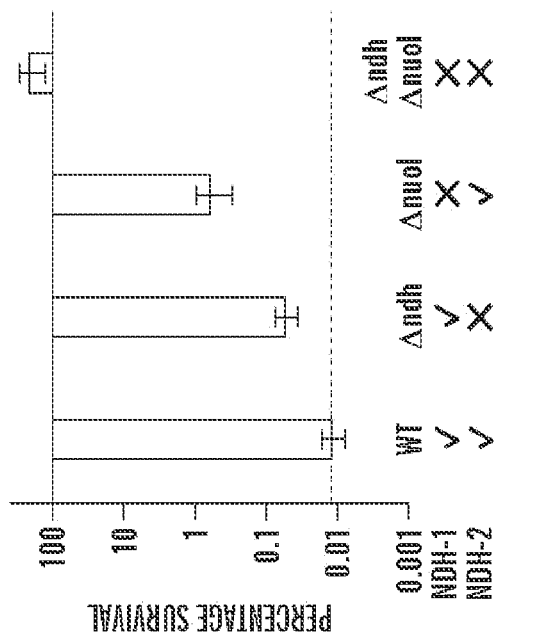
Figure 2D:
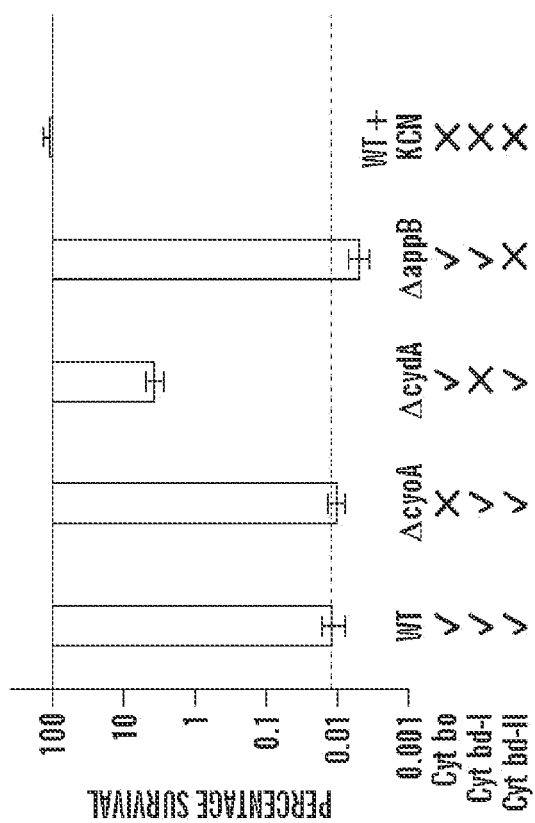
Figure 16:
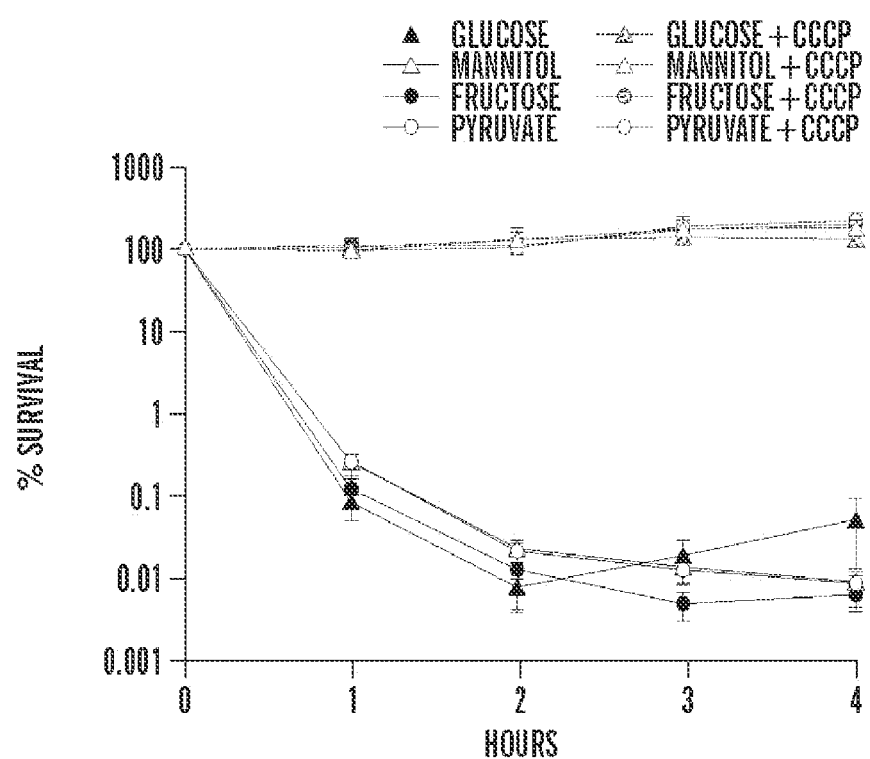
FIG. 16 demonstrates CCCP abolishes metabolite-enabled potentiation in E. coli persisters. Percent survival of wild-type E. coli persisters after treatment with 10 µg/mL gentamicin plus uptake-potentiating carbon sources (solid lines and solid squares) or uptake-potentiating carbon sources with 20 µM CCCP (dashed lines and open squares).
Figure 17A:
FIGS. 17A-17D demonstrate metabolite-enabled aminoglycoside uptake requires PMF. Representative measurements of uptake of 10 µg/mL fluorescently labeled gentamicin (Gent-TR) by stationary phase cells after 30 minutes incubation with no carbon source, carbon source, or carbon source and 20 µM CCCP. The following carbon sources were used: 17A, 10 mM glucose, 17B, 10 mM mannitol, 17C, 10 mM fructose, and 17D, 20 mM pyruvate.
Figure 17B:
Figure 17C:
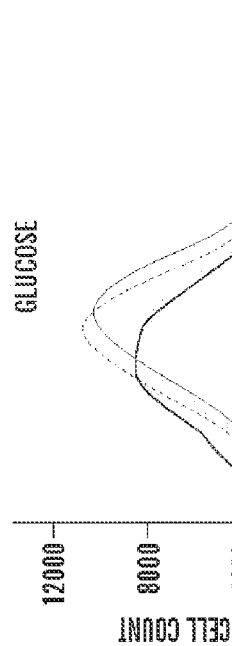
Figure 17D:
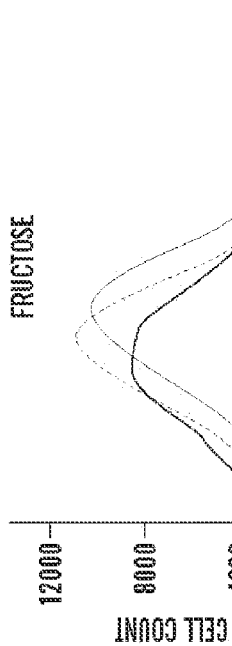
Figure 18:
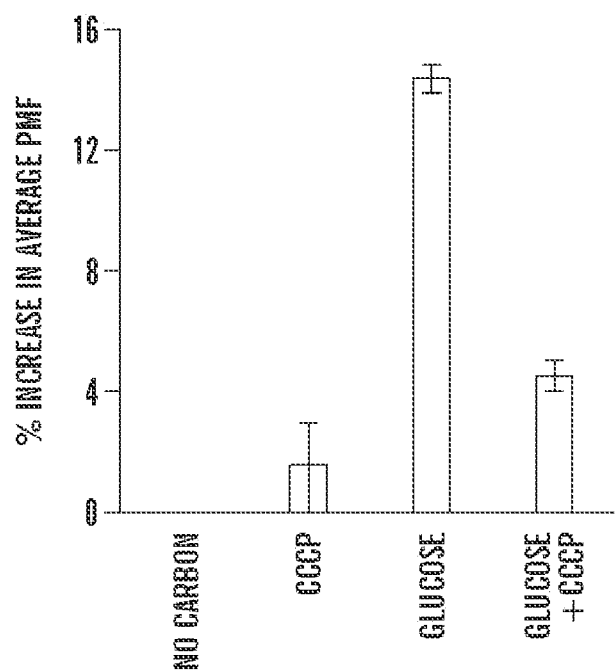
FIG. 18 demonstrates glucose induces PMF in dormant E. coli. Mean percent increase in membrane potential, measured as red/green from DiOC2(3) (see Methods), induced by no treatment, 20 µl CCCP, 10 mM glucose, and 10 mM glucose plus 20 µl CCCP.
Figure 19:
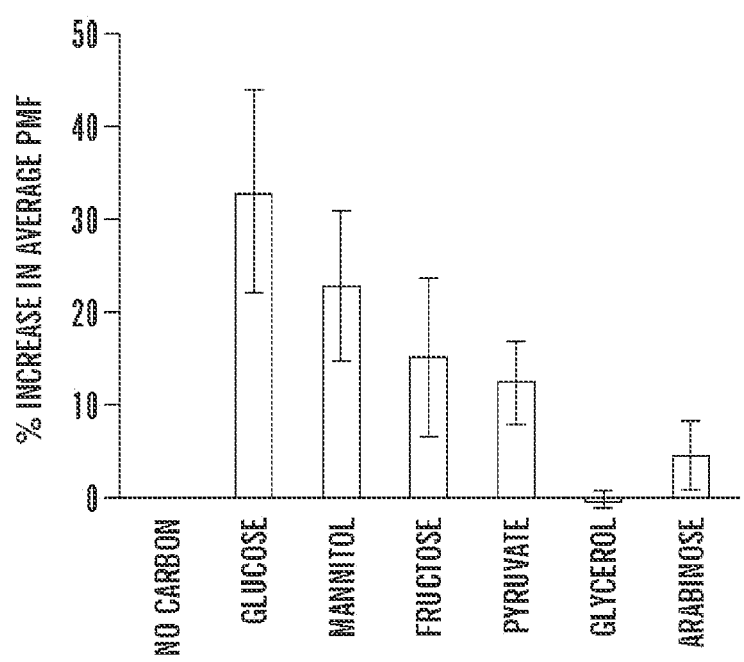
FIG. 19 demonstrates induction of PMF in dormant E. coli by different metabolites. Mean percent increase in membrane potential, measured as red/green from DiOC2(3) (see Methods), induced by no carbon, 10 mM glucose, 10 mM mannitol, 10 mM fructose, 20 mM pyruvate, 20 mM glycerol, and 12 mM arabinose.
Figure 20A:
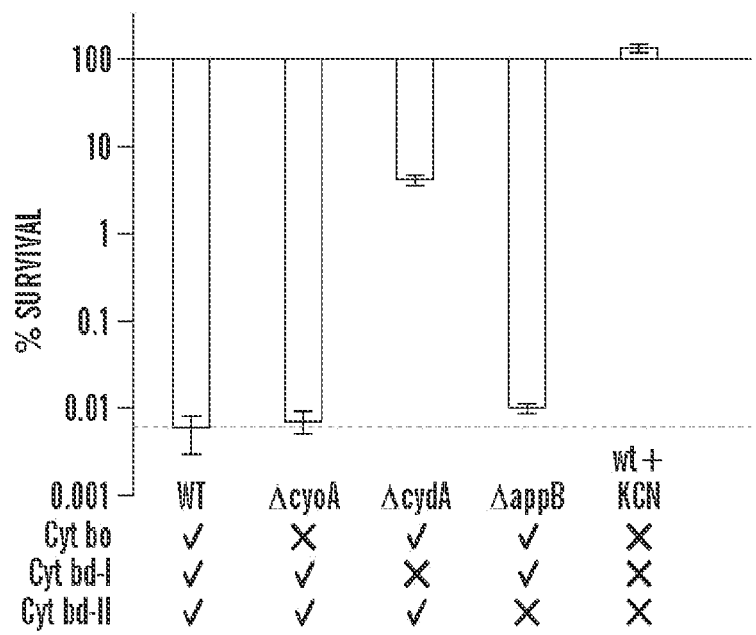
FIGS. 20A-20C demonstrate aerobic respiration is necessary for the observed metabolite-enabled eradication of bacterial persisters. Percent survival of persisters in strains with genetic perturbations to the three E. coli cytochromes after treatment with 10 µg/mL gentamicin plus: 20A, 10 mM glucose, 20B, 10 mM fructose, and 20C, 20 mM pyruvate. The presence (checks) and absence (X's) of functional cytochrome complexes is indicated below the tested conditions.
Figure 20B:
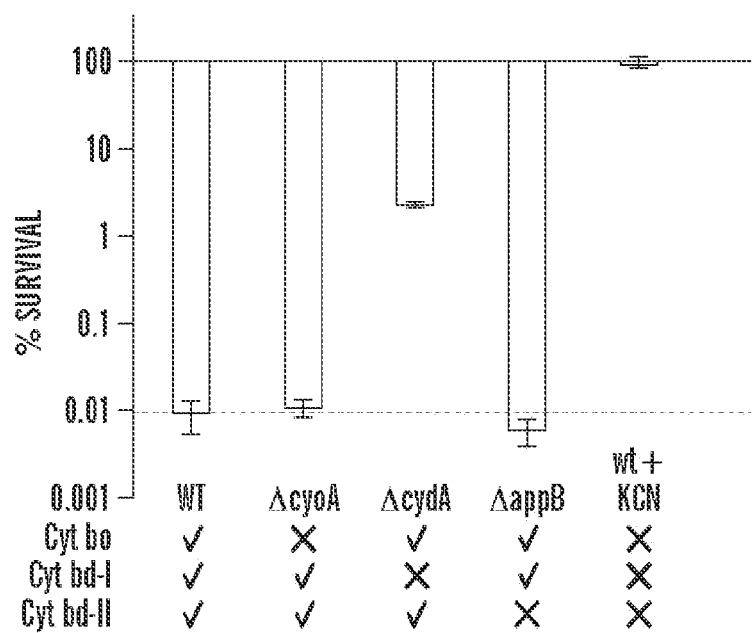
Figure 20C:
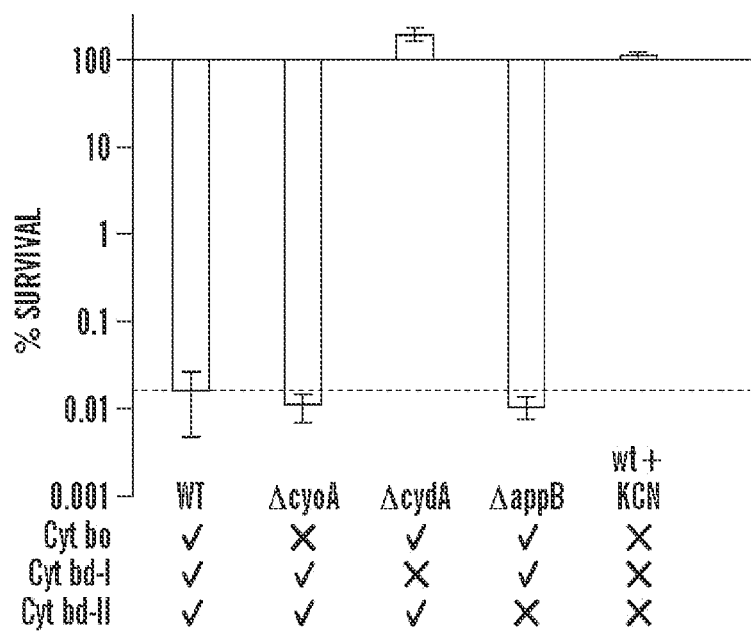

The requirement of proton-motive force (PMF) for aminoglycoside uptake in exponentially growing bacteria has been studied extensively[16]. Although the complete mechanism of aminoglycoside uptake is unclear, it is known that a threshold PMF is required. We reasoned that, although metabolic stimuli do not rapidly stimulate the growth of persisters, they can promote PMF, thereby facilitating the uptake of aminoglycosides and subsequent bacterial killing. To test this, we pre-incubated bacterial persisters with the proton ionophore carbonyl cyanide m-chlorophenyl hydrazone (CCCP), which inhibits PMF, before treating them with metabolites in conjunction with gentamicin. Treatment with CCCP was found to abolish aminoglycoside potentiation by all of the carbon sources, demonstrating that PMF, induced by metabolites, is required for persister elimination (FIG. 2A and FIG. 16). We next verified that the requirement for PMF was due to aminoglycoside uptake. We pre-incubated samples with CCCP and performed gentamicin-Texas red uptake experiments, showing that inhibiting PMF suppressed the metabolite-induced uptake of aminoglycoside (FIG. 2B and FIGS. 17A-17D). Furthermore, using the membrane stain 3,3'-diethyloxacarbocyanine iodide (DiOC2(3)), we verified that metabolites that induced aminoglycoside uptake and bacterial killing were also the ones that induced an elevated PMF (Supplementary FIGS. 14 and 15). These results demonstrate that specific metabolites induce PMF in persisters, thereby facilitating aminoglycoside uptake and bacterial killing.

Figure 21:
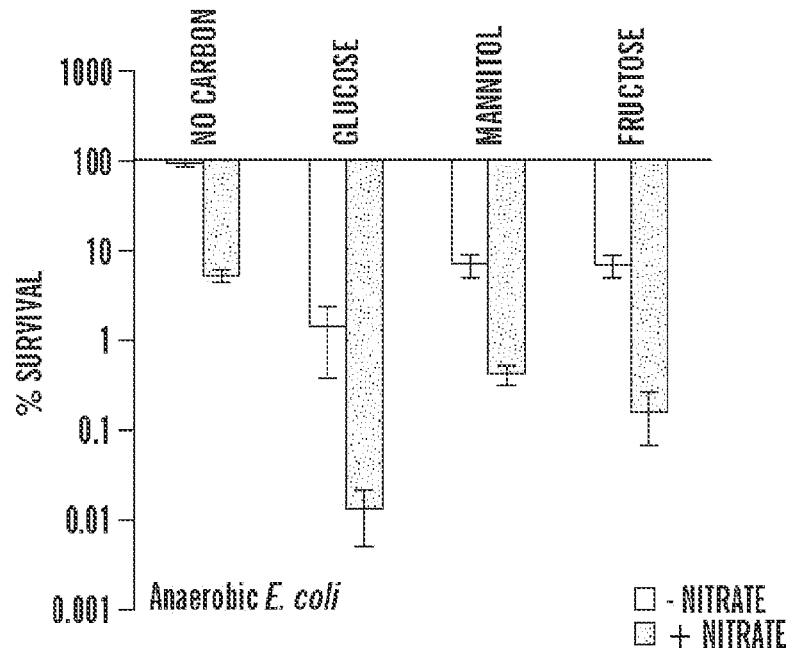
FIG. 21 demonstrates anaerobic metabolite-enabled eradication of dormant bacteria. Percent survival of stationary phase wild-type E. coli (EMG2) after 4-hour treatment with 10 mM indicated carbon source plus 10 µg/mL gentamicin (dark bars) or 10 mM nitrate and 10 µg/mL gentamicin (light bars). Growth and treatment of cultures were conducted in an anaerobic chamber.
Figure 22A:
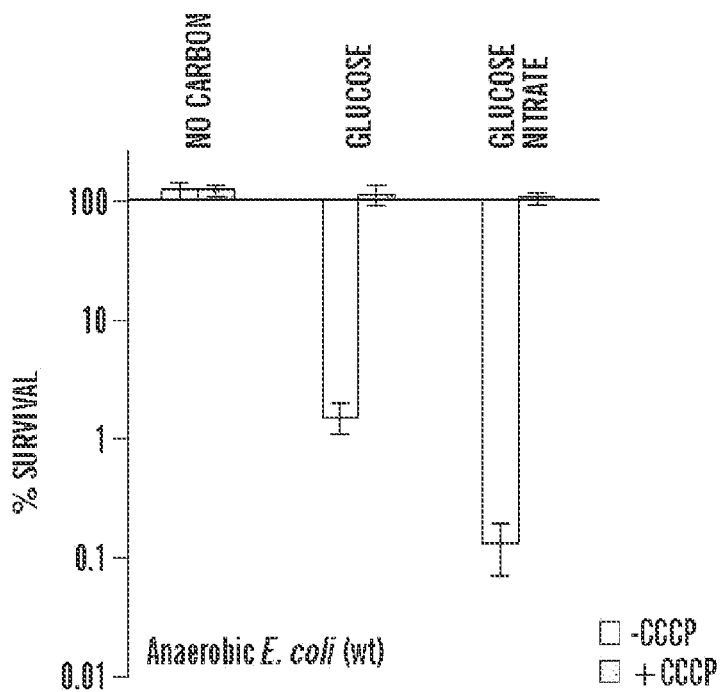
FIGS. 22A-22B demonstrate anaerobic metabolite-enabled eradication of dormant bacteria requires PMF. Percent survival of stationary phase wild-type (22A) and ΔndhΔnuoI (22B) E. coli (EMG2) after 4-hour treatment with 10 µg/mL gentamicin, with (light bars) and without (dark bars) 20 µM CCCP, and with 10 mM glucose and 10 mM nitrate. Growth and treatment of cultures were conducted in an anaerobic chamber.
Figure 22B:
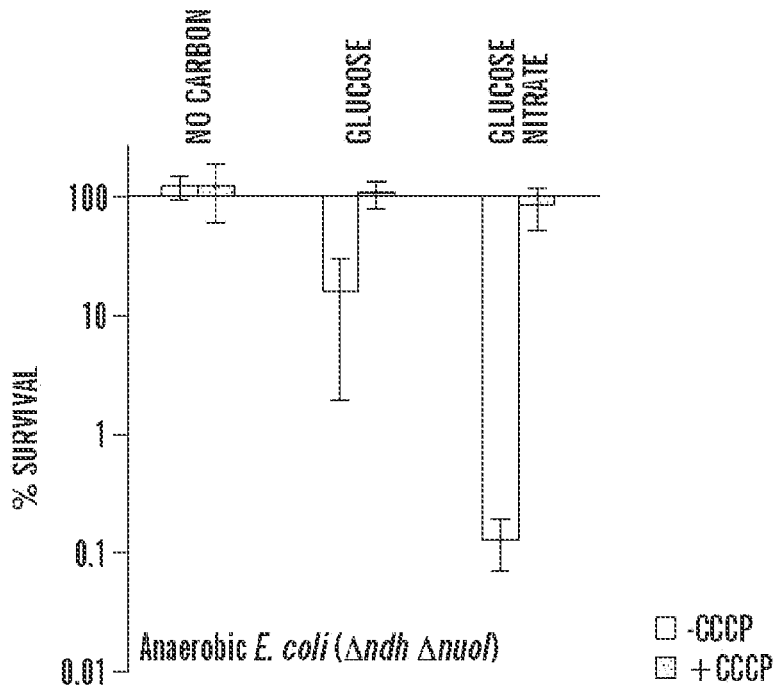
Figure 23A:
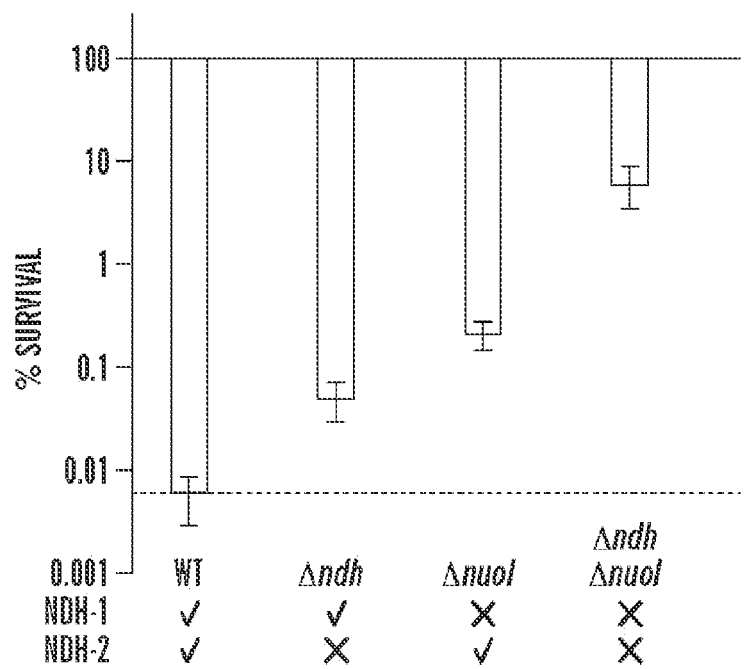
FIGS. 23A-23C demonstrate NADH dehydrogenase activity is important for metabolite-enabled eradication of bacterial persisters by most carbon sources. Percent survival of persisters in strains with genetic perturbations to the two E. coli NADH dehydrogenase complexes after treatment with 10 μg/mL gentamicin plus: 23A, 10 mM glucose, 23B, 10 mM fructose, and 23C, 20 mM pyruvate. The presence (checks) and absence (X's) of functional NADH dehydrogenase complexes is indicated below the tested strains.
Figure 23B:
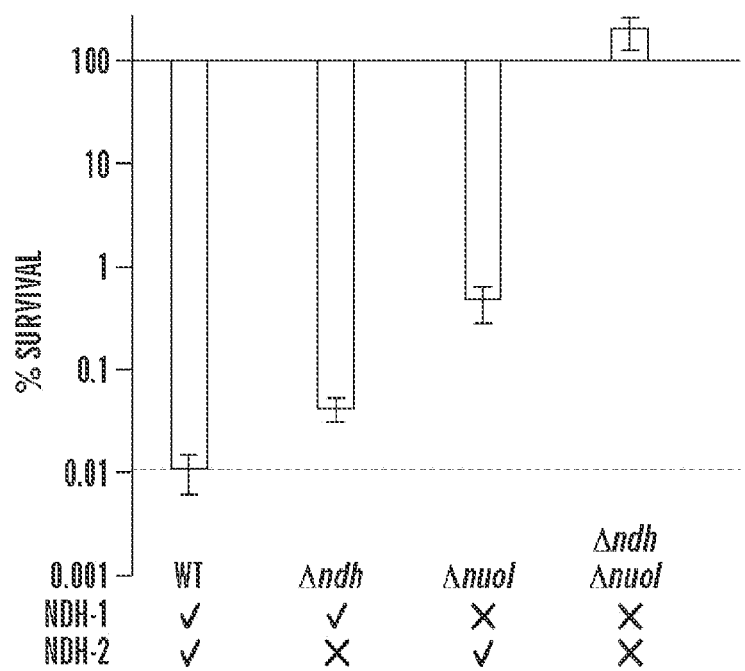
Figure 23C:
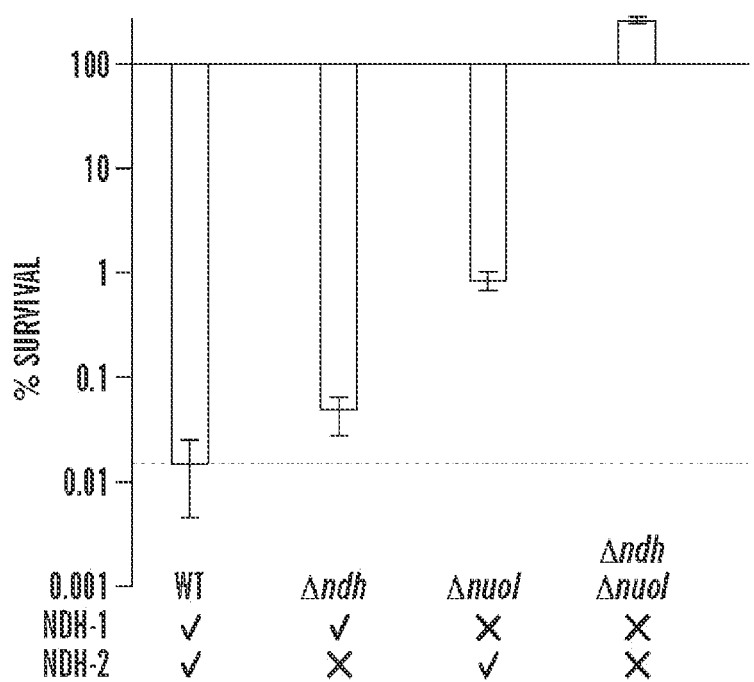

From these results, we reasoned that aerobic respiration is primed in persisters and that it facilitates the metabolic potentiation of aminoglycosides. We tested this using genetic knockout strains inactivated for each of the E. coli cytochrome quinol oxidases (bo, ΔcyoA; bd-I, ΔcydB; bd-II, AappB). We also used potassium cyanide to inhibit all cytochromes simultaneously. Wild-type persisters, with and without potassium cyanide, and enzymatically inactivated persisters were treated for 2 h with gentamicin plus metabolites (FIG. 2C and FIGS. 20A-20C). Treatment with potassium cyanide abolished bacterial killing, consistent with studies of rapidly growing bacteria[17], demonstrating the necessity of aerobic respiration for elimination of persisters by aminoglycosides under these conditions. The AcydB mutation, which abolishes activity of the microaerobic cytochrome bd-I[18,19], suppressed killing by more than two orders of magnitude, possibly owing to the use of cytochrome bd-I in oxygen-depleted and alkaline stationary-phase cultures. Neither ΔcyoA nor ΔappB showed a significant effect on bacterial killing. Although we found that aerobic respiration was required for eradication of bacteria in aerated conditions, we also found that metabolite-enabled eradication occurs anaerobically in conditions that support PMF (FIG. 21, FIGS. 22A-22B).

Figure 24:
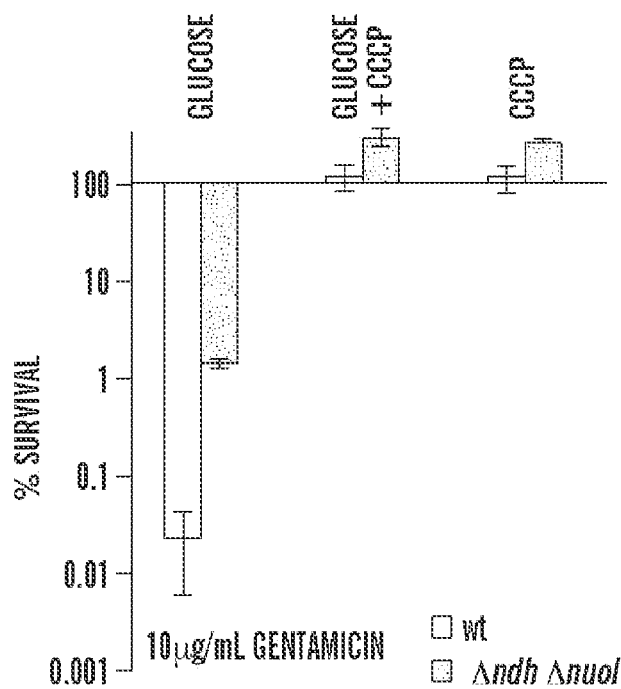
FIG. 24 demonstrates PMF is required for metabolite-enabled eradication of bacterial persisters in the MdhMuoI strain. Percent survival of persisters in the wild-type and ΔndhΔnuoI E. coli strains after treatment with 10 μg/mL gentamicin plus 10 mM glucose, 20 μl CCCP, or both 10 mM glucose and 20 μl CCCP.
Figure 25:
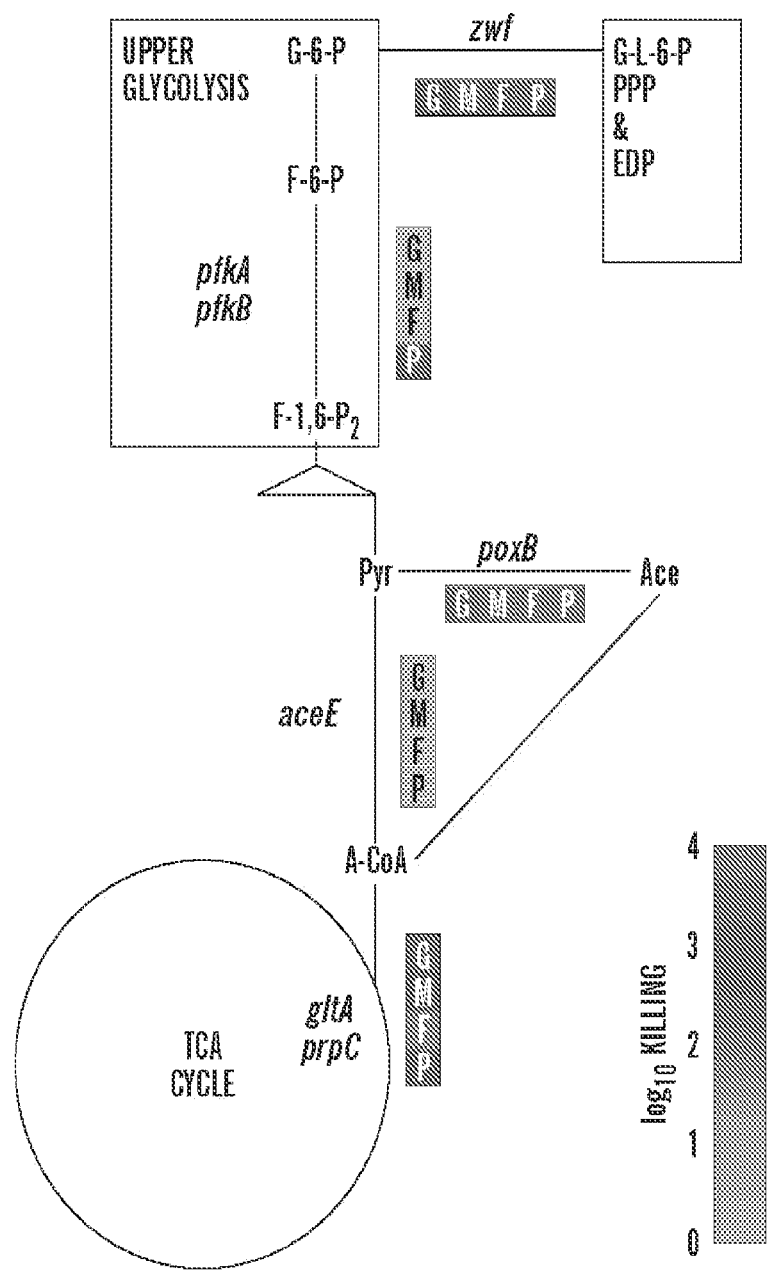
FIG. 25 demonstrates source of NADH production in aminoglycoside killing of E. coli persisters. Heat maps of gentamicin potentiation by carbon sources in genetic knock-outs overlaid on central metabolism. The box around each letter ("G" for glucose, "M" for mannitol, "F" for fructose, and "P" for pyruvate) indicates the aminoglycoside potentiation induced by carbon sources in a knockout strain. The knocked-out enzymatic steps are labeled opposite the heat maps to which they correspond (see also FIGS. 26A-26E).
Figure 26B:
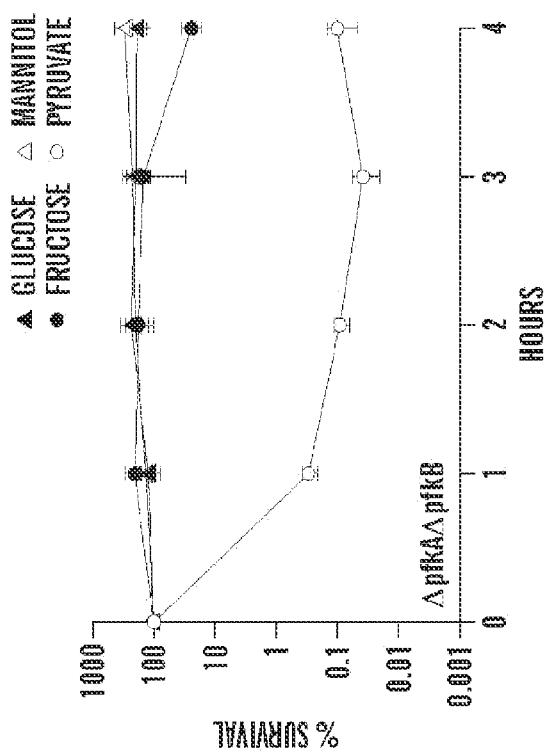
FIGS. 26A-26E demonstrate potentiation of aminoglycoside killing of E. coli persisters by carbon sources in metabolic mutants. Survival of 26A, Δzwf, 26B, ΔpjkAΔpfkB, 26C, ΔpoxB, 26D, ΔgltAΔprpC, and 26E, ΔaceE E. coli (EMG2) persisters treated with 10 μg/M1 gentamicin plus 10 mM glucose, 10 mM mannitol, 10 mM fructose, or 20 mM pyruvate.
Figure 26A:
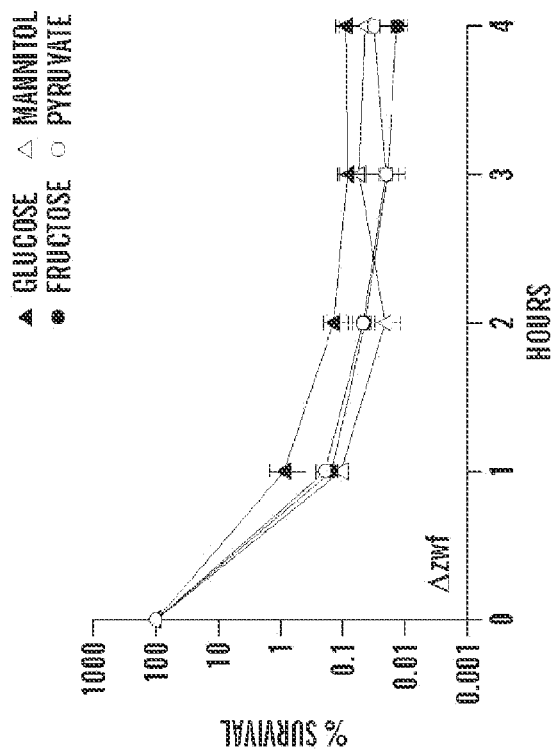
Figure 26D:
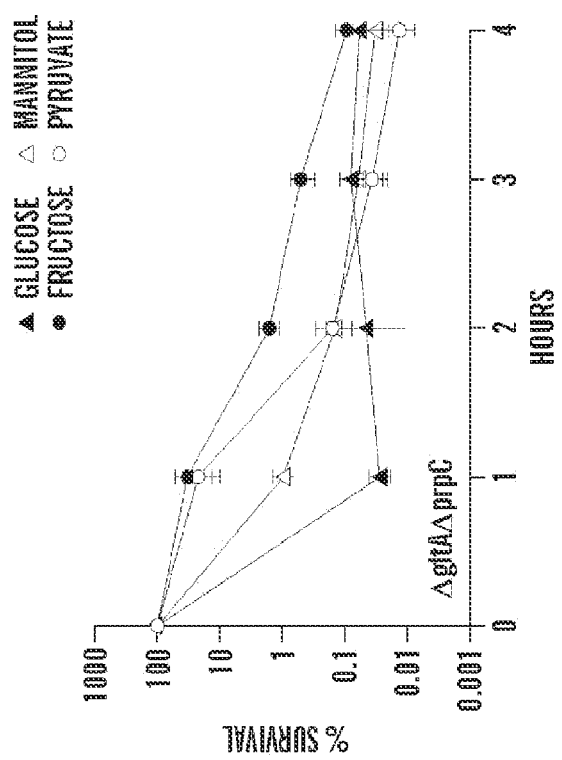
Figure 26C:
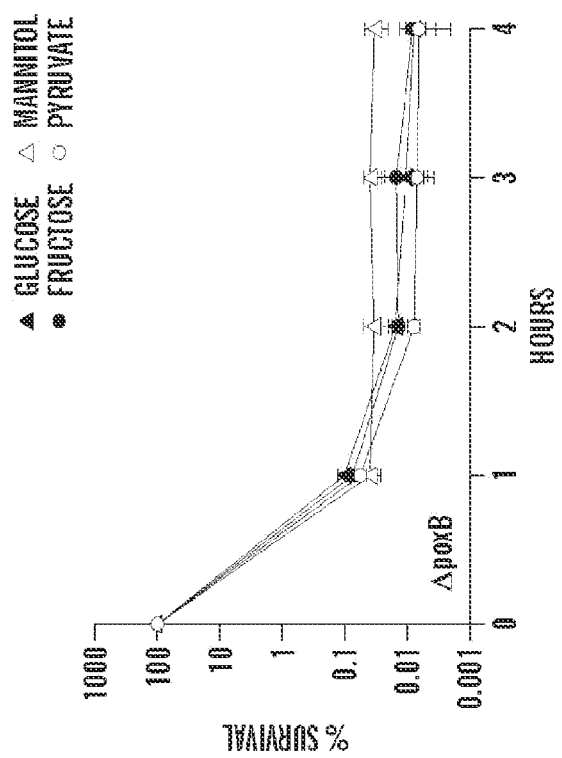
Figure 26E:
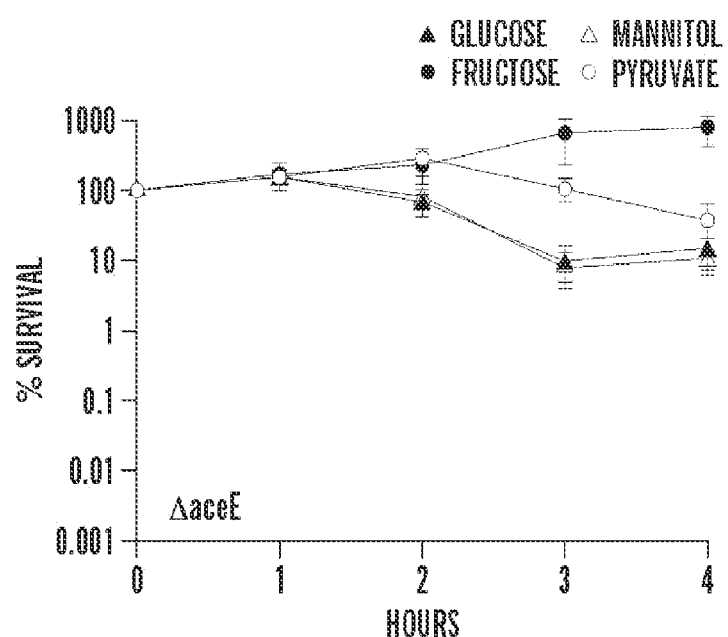
Figure 27A:
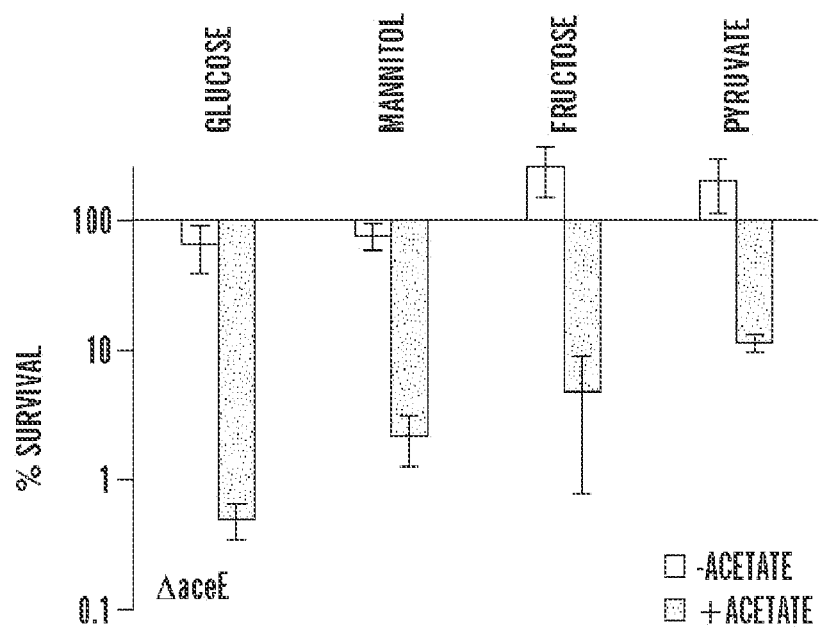
FIGS. 27A-27B demonstrate NADH production by pyruvate dehydrogenase induces aminoglycoside killing of E. coli persisters. 27A, Percent survival of ΔaceE E. coli persisters after 2-hour treatment with 10 μg/mL gentamicin and potentiating carbon source without acetate (light grey bars) or with 10 mM acetate (dark grey bars). 27B, Percent survival of ΔgltAΔprpCΔaceE E. coli after 2-hour treatment with 10 μg/mL gentamicin and potentiating carbon source without acetate (light grey bars) or with 10 mM acetate (dark grey bars) (see also FIG. 24).
Figure 27B:
Figure 28A:
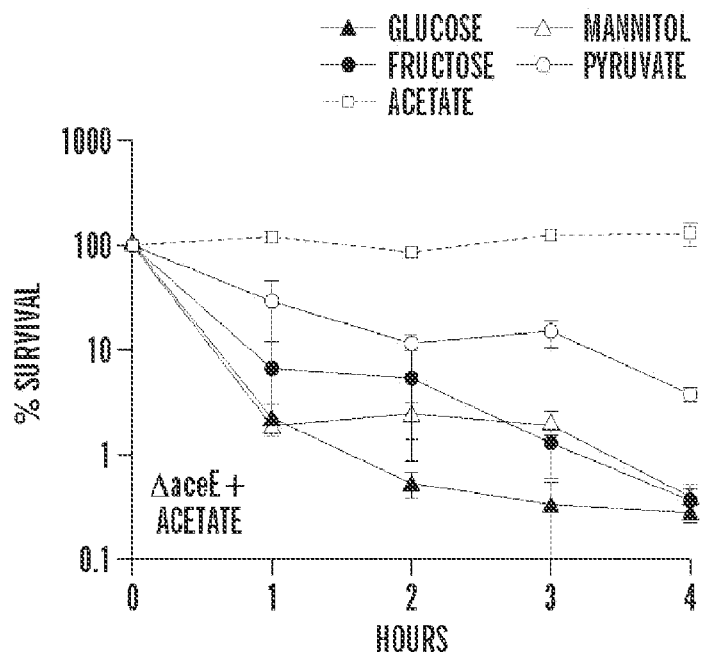
FIGS. 28A-28B demonstrate pyruvate dehydrogenase activity, due to its NADH generation, is important to the observed metabolite-enabled potentiation in persisters. 28A, Survival of ΔaceE persisters after treatment with 10 μg/mL gentamicin, 10 mM acetate, and one of the following carbon sources: 10 mM glucose, 10 mM mannitol, 10 mM fructose, or 20 mM pyruvate. Survival of ΔaceE persisters after treatment with 10 μg/mL gentamicin and 30 MM acetate (black dashed lines and open squares). 28B, Survival of ΔgltAΔprpCΔaceE persisters after treatment with 10 μg/mL gentamicin, 10 mM acetate, and one of the following carbon sources: 10 mM glucose, 10 mM mannitol, 10 mM fructose, or 20 mM pyruvate.
Figure 28B:
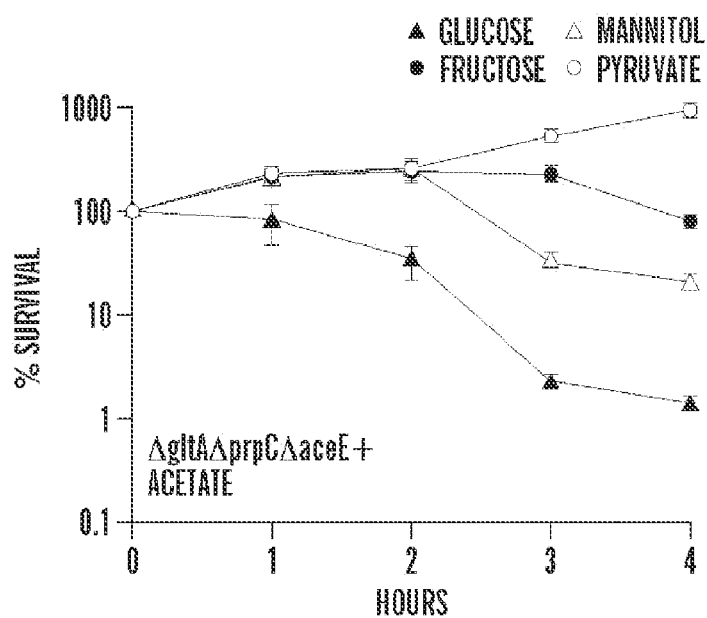
Figure 29:
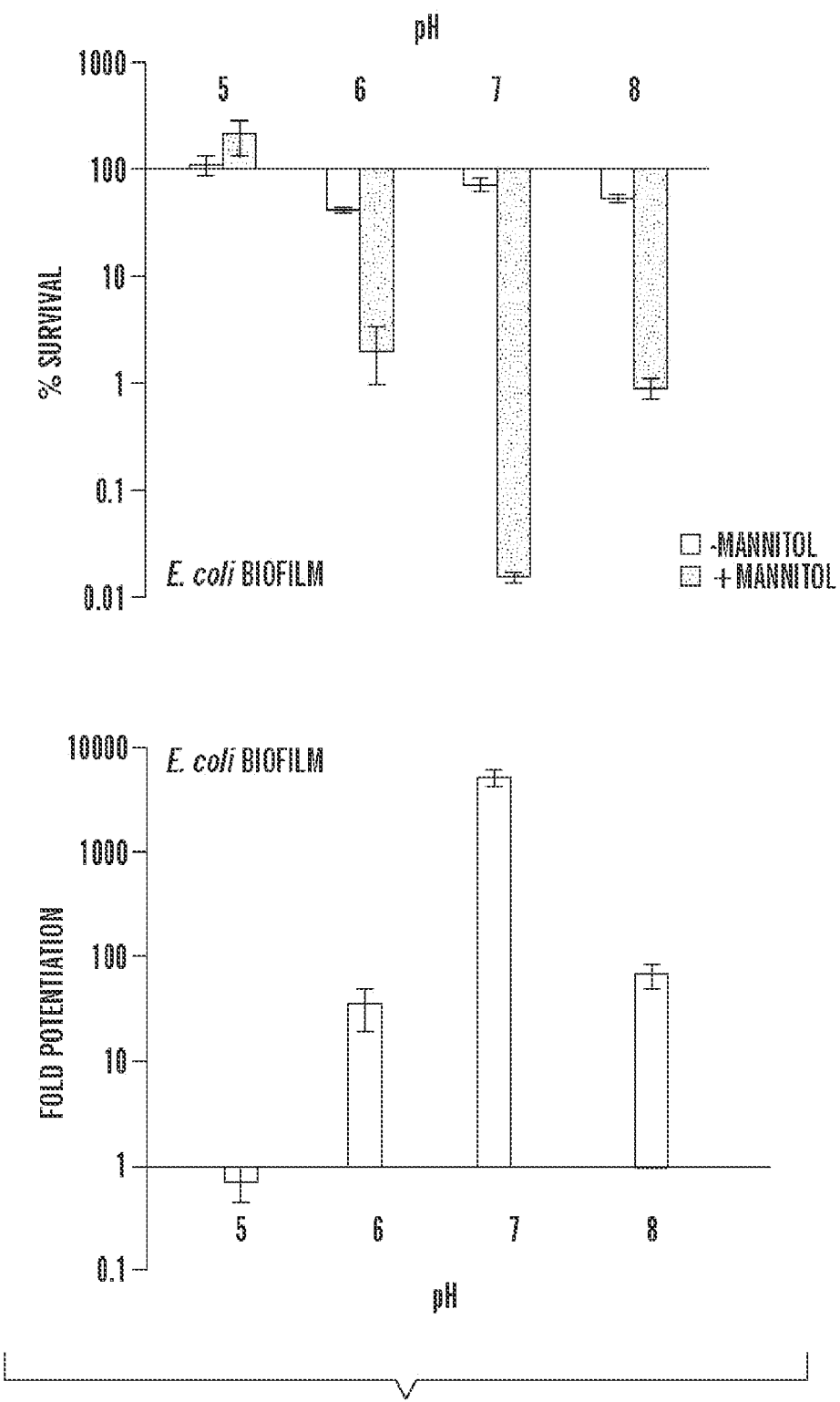
FIG. 29 demonstrates dependence of biofilm eradication on pH. Top. Percent survival of wild-type E. coli (EMG2) biofilms after 4-hour treatment with 10 μg/mL gentamicin or 10 mM mannitol plus 10 μg/mL gentamicin in M9 buffered to the indicated pH. Bottom. Fold gentamicin potentiation induced by 10 mM mannitol against biofilms at indicated pH.
Figure 30:
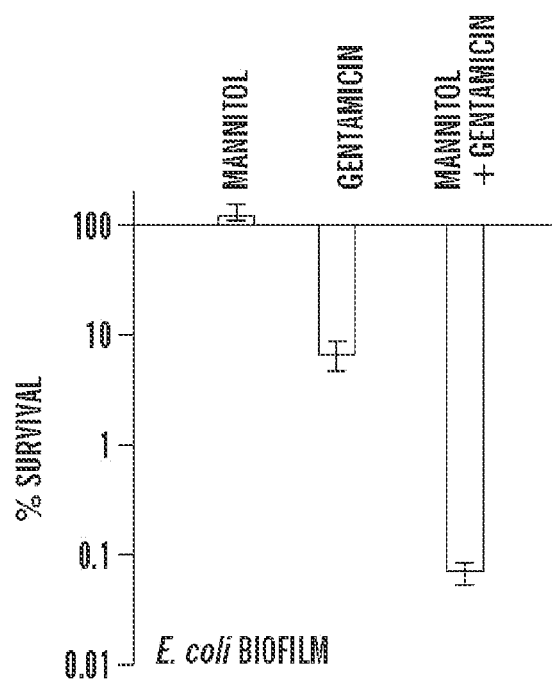
FIG. 30 demonstrates biofilm eradication at longer timescales. Percent survival of wild-type E. coli (EMG2) biofilms after 8-hour treatment with 10 mM mannitol, 10 μg/mL gentamicin or 10 mM mannitol plus 10 μg/mL gentamicin in M9 minimal media.
Figure 31:
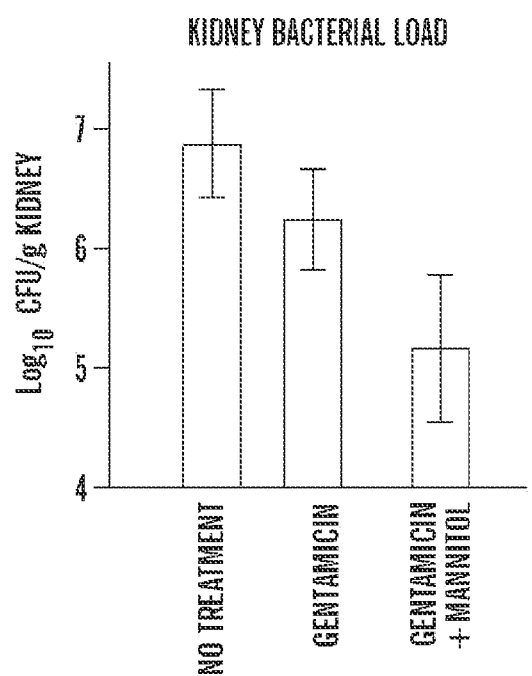
FIG. 31 demonstrates in vivo that mannitol plus gentamicin stops spread of infection to mouse kidneys. Mice had catheters colonized with uropathogenic E. coli biofilms surgically implanted in their urinary tracts. Forty-eight hours after surgery, mice received no treatment or twice-daily, intravenous treatment with gentamicin (1 mg/Kg) or mannitol (1.5 g/Kg) and gentamicin (1 mg/Kg) for three days. Twenty-four hours after the last treatment, kidneys were removed and bacterial load was determined and plotted as log 10 CFU/g kidney.

Because aerobic respiration in E. coli is driven by NADH oxidation, we investigated the role of NADH utilization in this phenotype. Persister cells inactivated for NADH dehydrogenase I (ΔnuoI), NADH dehydrogenase II (Δndh) and both NADH dehydrogenases (ΔndhΔnuoI) were treated for 2 h with gentamicin plus metabolites (FIG. 2D and FIGS. 23A-23C). We found that NADH dehydrogenase activity was important for this phenotype because gentamicin activity against the ΔndhΔnuoI strain was not potentiated by mannitol, fructose or pyruvate, although there was slight potentiation by glucose FIG. 23A). We found that NADH is not essential for killing under all conditions (FIGS. 22A-22B, FIG. 24). Both the ndh and nuoI deletions suppressed killing but the ΔnuoI strain was the more resistant of the two, reflecting the direct contribution of NADH dehydrogenase I to PMF. Using a series of genetic knockouts, we further determined that the enzyme pyruvate dehydrogenase was necessary for the observed phenotype, owing to its generation of NADH, whereas the PPP, EDP and TCA cycle were not necessary FIG. 25, FIGS. 26A-26E, FIGS. 27A-27B, FIGS. 28A-28B).

Figure 3A:
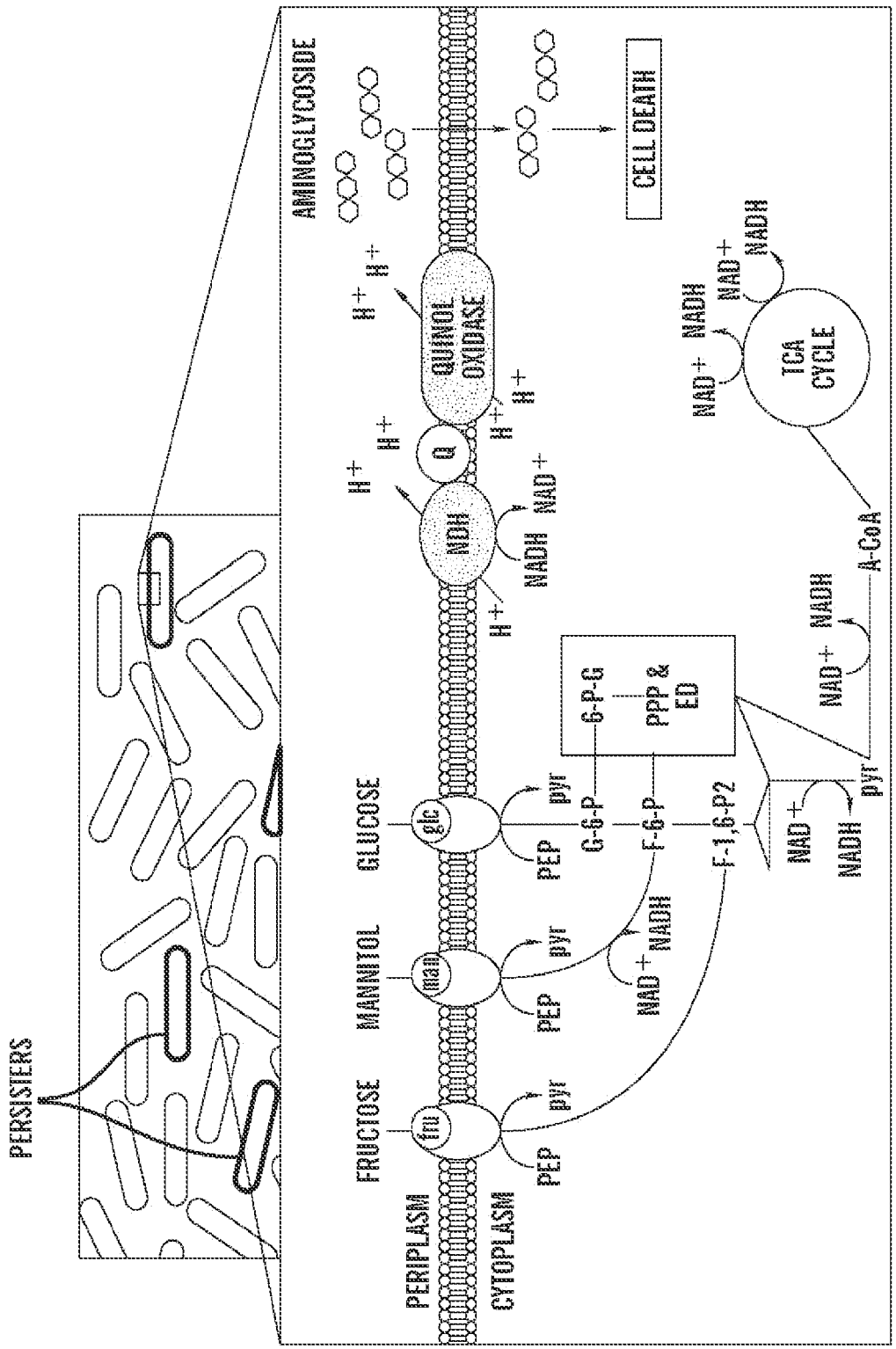

These results showed that persisters are primed for specific biochemical processes that allow PMF induction, including central metabolism. However, in the timescales examined here, this resumption of central metabolism and respiration was not sufficient to support other processes necessary for cellular growth, such as cell-wall biogenesis and DNA replication. Thus, persisters treated with specific metabolites seem to be in an energized but non-dividing state that facilitates their elimination by aminoglycosides. On the basis of these findings, we propose, without wishing to be bound or limited by theory, the following mechanism for metabolite-enabled eradication of persisters by aminoglycosides (FIG. 3A). Certain metabolites—glucose, mannitol, fructose and pyruvate—are transported to the cytoplasm, some by their specific phosphotransferase system enzymes; they enter glycolysis, where their catabolism generates NADH, and this NADH is then oxidized by enzymes in the electron transport chain, which contribute to PMF. The elevated PMF facilitates the uptake of aminoglycosides, which bind to the ribosome and cause cell death via mistranslation.

We next investigated whether this mechanism was applicable to clinically relevant cases, such as bacterial biofilms. We reasoned that metabolic stimulation can be used to facilitate the elimination of biofilm persisters by aminoglycosides. To test this, we grew E. coli biofilms and treated them for 4 h with ofloxacin, mannitol, gentamicin and mannitol plus gentamicin (FIG. 3B). Ofloxacin, which is efficient against Gram-negative biofilms[15,20], reduced biofilm viability by almost two orders of magnitude, indicating that more than 1% of the bacteria in the biofilms were persisters. Mannitol and gentamicin, in combination, reduced biofilm viability by more than four orders of magnitude, representing a reduction in biofilm persisters of 2.5 orders of magnitude. We also tested the ability of fructose to induce biofilm elimination and observed similar results (FIG. 3C).

To determine the clinical relevance of metabolic potentiation of aminoglycosides in vivo, we tested the ability of gentamicin in combination with mannitol to treat chronic, biofilm-associated infection in a mouse model. Catheters colonized with uropathogenic *E. coli* biofilms were implanted in the urinary tracts of mice (FIG. 3D). Two days after surgery, mice received either no treatment or intravenous treatment with gentamicin or gentamicin and mannitol for 3 days, after which the catheters were removed and biofilm viability was determined. Gentamicin alone had no effect, whereas gentamicin in combination with mannitol reduced the viability of the catheter biofilms by nearly 1.5 orders of magnitude (FIG. 3D). We also found that treatment with gentamicin and mannitol inhibited the spread of bacterial infection to the kidneys, as compared to treatment with gentamicin alone and to the untreated control FIG. 3I). These in vivo results demonstrate the feasibility of the approaches and methods described herein for clinical use.

Figure 4B:
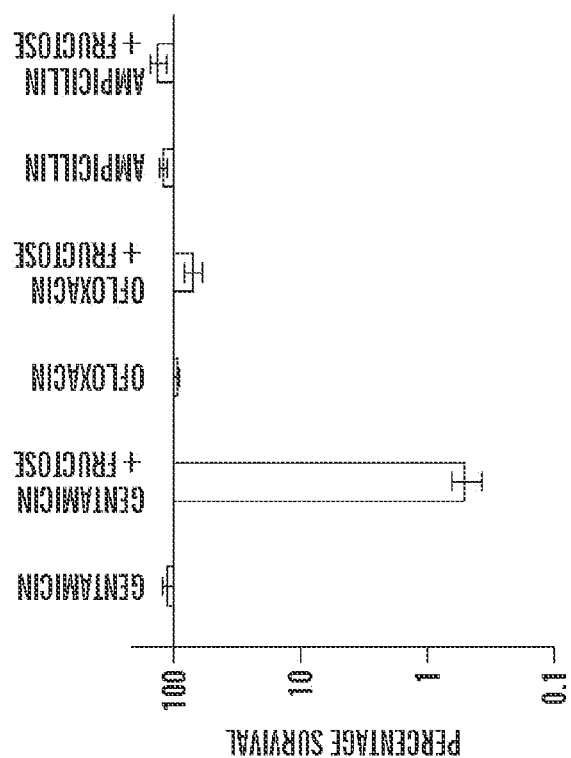
Figure 4A:
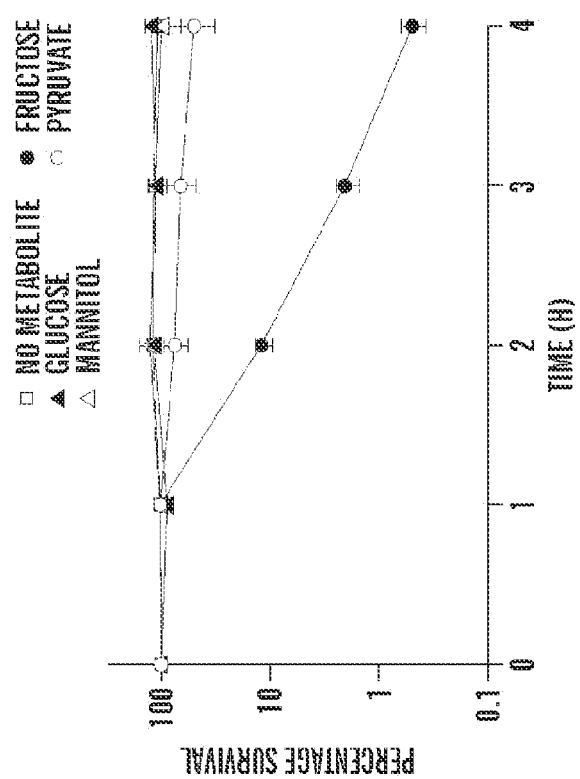

Having shown that certain metabolites can enable aminoglycoside activity in Gram-negative (*E. coli*) bacterial persisters and biofilms, we sought to determine whether a similar phenomenon existed in Gram-positive bacteria. Persisters of the Gram-positive pathogen *S. aureus* were treated with gentamicin in conjunction with metabolites. After an initial hour in which no killing was seen, gentamicin with fructose rapidly eliminated persistent *S. aureus* (FIG. 4A). Interestingly, mannitol, glucose and pyruvate, which showed strong potentiation against *E. coli* persisters, showed little potentiation against *S. aureus*. Expression analysis using *S. aureus* microarrays indicated that this lack of potentiation results from differential expression of metabolite transporters in growing versus dormant *S. aureus* (Table 3). We next tested whether the fructose-enabled killing of *S. aureus* was unique to aminoglycosides or general to other classes of bactericidal antibiotics. As with *E. coli*, we found that metabolite-enabled killing of *S. aureus* persisters was Specific to aminoglycosides (FIG. 4B), indicating that *S. aureus* persisters did not revert to normally growing cells when treated with metabolites.

Given that the activity of aminoglycosides in growing *S. aureus* is dependent on PMF[21, 22], we tested whether the elimination of persisters mediated by fructose also required PMF. We found that the potentiation of aminoglycosides by fructose in *S. aureus*, as in *E. coli*, requires PMF generation (FIG. 4C), indicating that the PMF-requiring mechanism exists in both Gram-negative and Gram-positive bacteria. We also investigated whether gentamicin with fructose could be used to treat *S. aureus* biofilms. We found that the viability of *S. aureus* biofilms was reduced by nearly 1.5 orders of magnitude when treated for 4 h with fructose and gentamicin (FIG. 4D).

To determine whether the observed potentiation was specific to gentamicin or general to aminoglycosides, we tested the effects of adding the upper-glycolytic metabolites glucose, mannitol, and fructose to streptomycin and kanamycin. As seen with gentamicin, streptomycin and kanamycin activity was greatly enabled by these metabolites, and the antibiotics showed no appreciable killing in the absence of carbon source, demonstrating that metabolic potentiation was a general aminoglycoside phenomenon (FIGS. 6A-6B).

Herein we have established an approach for eradicating bacterial persisters which is based on metabolism and is effective against both Gram-negative and Gram-positive bacteria. The metabolite-mediated potentiation occurs, in part, via PMF generation, which we found was necessary for aminoglycoside uptake and killing of persisters. This work adds to a growing understanding of the role of metabolism in killing by bactericidal antibiotics[13,23,24] and broadens our understanding of persister physiology. Moreover, our findings indicate that delivering PMF-stimulating metabolites as adjuvants to aminoglycosides is beneficial in the treatment of chronic bacterial infections, as demonstrated herein using murine models.

Methods

Antibiotics and Chemicals

The following concentrations of antibiotics were used in this study.

10 μg ml$^{-1}$ gentamicin, 30 μg m$^{-1}$ kanamycin, 50 μg ml$^{-1}$ streptomycin, 5 μg ml$^{-1}$ ofloxacin, 100 μg ml$^{-1}$ ampicillin, 40 μg ml$^{-1}$ tetracycline, 50 μg ml$^{-1}$ chloramphenicol and 100 μg ml$^{-1}$ spectinomycin. 20 μM carbonyl cyanide m-chlorophenyl hydrazone (CCCP) was used in experiments to suppress proton-motive force. 1 mM potassium cyanide was used to inhibit aerobic respiration. A stock solution of CCCP was made in dimethylsulphoxide at 500 nM and stored at 4° C. All antibiotics and chemicals were purchased from Sigma and Fisher.

Media and Growth Conditions

All stationary-phase samples were prepared in the following way: cells from frozen stock were grown at 37° C. 300 r.p.m. and 80% humidity in Luria-Bertani (LB) broth to an optical density at 600 nm ($OD_{600}$) of 0.3. Cells were then diluted 1:1,000 in 25 ml LB and grown for 16 h at 37° C., 300 r.p.m. and 80% humidity in 250 ml flasks. This experimental set-up ensured that, regard of the conditions used in assays, the initial population of persisters or stationary-phase cells was prepared in a uniform manner consistent with previous work (Keren, I., Kaldalu, N., Spoering, A., Wang, Y. & Lewis, K. Persister cells and tolerance to antimicrobials. FEMS Microbiol. Lett. 230, 13-18 (2004))[26].

The following concentrations of carbon sources were used in this study: 10 mM glucose, 10 nM mannitol, 10 mM fructose, 20 mM glycerol, 30 mM glycolate, 10 mM galactarate. 20 mM pyruvate, 10 mM gluconate, 12 mM arabinose and 12 mM ribose. 10 mM acetate was used as a supplement and 30 mM acetate was used as a potentiating metabolite in control experiments. Carbon sources were purchased from Sigma or Fisher. In *E. coli* persister assays, samples were re-suspended in M9 minimal media salts plus a carbon source. In all experiments using CCCP, samples were pre-treated for 5 min with the proton ionophore before antibiotic addition.

Strains

The parent strains used in this study were *E. coli* (K12 EMG2) and *S. aureus* (ATCC 25923). All *E. coli* knockouts (see Table 2) were transduced into the EMG2 strain from strains in the KEIO knockout collection using the PI phage method. All strains were cured using pCP20 and standard laboratory procedures before their use in assays.

Persister Assays

For *E. coli* persister assays, samples were grown to stationary phase as described above. Cultures were then treated for 4 h with 5 μg ml$^{-1}$ ofloxacin in the above-stated growth conditions.

Figure 5:
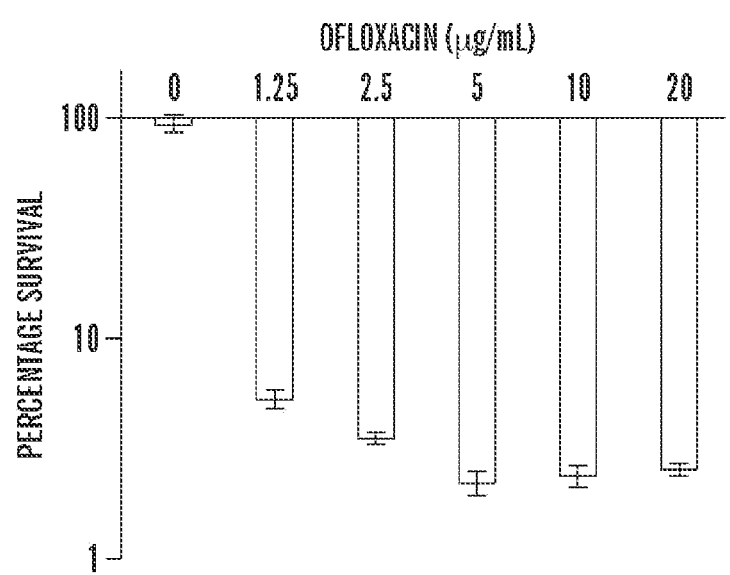
FIG. 5 demonstrates that increasing concentrations of ofloxacin do not decrease survival. Percent survival of stationary phase wild-type E. coli after 4-hour treatment with indicated concentrations of ofloxacin.

Previous work has demonstrated that treatment for 3 h under these conditions eliminates all susceptible non-persister cells[25]. We verified that the remaining cells were persisters by increasing the amount of ofloxacin added to the culture to 20 μg ml$^{-1}$ and noted no further decrease in viability (FIG. 5). Persistence was further verified by demonstrating that none of the bactericidal antibiotics used in this study killed cells when added without a carbon source (FIG. 1C). Samples were then washed with 10 ml of 1× filtered PBS and re-suspended in M9 minimal media. Carbon sources and antibiotics were added and samples were incubated at 37° C. 300 r.p.m. and 80% humidity Re-suspension of samples in defined minimal media allowed us to test the effects of different carbon sources on persister viability precisely and specifically, without the possible confounding factors that a more complex medium would present. For *S. aureus* persister experiments, cells were grown at 37° C. and 300 r.p.m. in LB broth to an $OD_{600}$ of 0.3. Cells were then diluted 1:1.000 in 25 ml LB and grown for 16 h at 37° C. and 300 r.p.m. in 250 ml flasks before treatment with a carbon source and antibiotic. Previous work has shown that almost all stationary-phase *S. aureus* cells are persistent[25].

At specified time points, 10-µl aliquots of samples were removed, serially diluted and spot-plated onto LB agar plates to determine colony-forming units per ml (c.f.u. $ml^{-1}$). Only dilutions that yielded 10-100 colonies were counted Survival was determined by dividing the c.f.u. $ml^{-1}$ of a sample at each time point by the initial c.f.u. $ml^{-1}$ for that sample.

For persister resuscitation experiments (FIGS. 9A-9J), cells that had been treated with ofloxacin, washed and re-suspended in M9 were then diluted 1:100 in M9 plus a carbon source and incubated at 37° C., 300 r.p.m. and 80% humidity.

Gentamicin-Texas Red Uptake

Gentamicin-Texas red was made as previously described[27]. At 4° C., 1 mg of Texas red (Invitrogen) was dissolved in 50 µl of high-quality anhydrous N,N-dimethylformamide The dissolved Texas red was added slowly to 2.3 ml of 10 m $ml^{-1}$ gentamicin solution in 100 mM $K_2CO_3$ at 4° C.

Uptake of gentamicin-Texas red induced by carbon sources in stationary-phase cells was determined by adding concentrated carbon sources (see section on media and growth conditions for concentrations) to stationary-phase cultures and incubating them for 30 min at 37° C., 300 r.p.m. and 80% humidity. Concentrated gentamicin-Texas red was then added to a final concentration of 10 µg $ml^{-1}$ and samples were incubated for 5 min. 100 µl of each sample was then washed with 1 ml of PBS and re-suspended in 1 ml of PBS. 200 µl of the re-suspended sample was then added to 800 µl of PBS in flow tubes. Samples were analysed on a BD FACS Aria II flow cytometer with the following settings; mCherry voltage, 650 V, FSC threshold, 1.000: recorded events, 100,000; gated-out mCherry events. <30.

Membrane Potential Measurements

We used the BACLIGHT BACTERIAL MEMBRANE POTENTIAL KIT (B34950, Invitrogen) to assess changes in proton-motive force induced by metabolites. Membrane potential induced by carbon sources in stationary-phase cells was determined by adding concenrated carbon sources (see section on media and growth conditions for concentrations) and 10 µl $DiOC_2(3)$ (membrane stain) to stationary-phase cultures, followed by incubation for 30 min at 37° C., 300 r.p.m and 80% humidity. 10 µl of culture was added to 1 ml of PBS in flow tubes immediately before analysing Samples were analysed on a BD FACS ARIA II flow cytometer with settings optimized according to the BacLight kit manual. Settings used were: FITC voltage, 250 V; mCherry voltage, 650 V; FSC threshold, 1.000; recorded events, 100,000. FSC and SSC outliers were gated out by visual inspection before data acquisition. The red/green (mCherry/FITC) values for each cell were determined and normalized, then compared to samples without metabolite to determine the relative change in PMF.

Anaerobic Experiments

*Escherichia coli* were grown to an $OD_{600}$ of 0.3, then diluted 1:1.000 in 25 ml anaerobic LB with 10 mM $NaNO_3$ and grown for 16 h at 37° C. 200 r.p.m, 1.5-2.0% hydrogen and <50 p.p.m. oxygen in 250 ml flasks. Cultures were then treated with a carbon source and metabolite in the presence or absence of an additional 10 mM $NaNO_3$. The additional $NaNO_3$ was added to determine whether increasing the concentration of the terminal electron acceptor could increase aminoglycoside potentiation.

Biofilm Assay

Overnight cultures grown in LB were diluted 1:200 into pre-warmed LB which was then added to MBEC plates (Innovotech) at 150 µl per well. Plates were incubated at 35° C., 150 r.p.m. for 24 h, then pegs were washed in a microtitre plate with 200 µl of 1×PBS per well. Pegs were then added to a microtitre plate containing 200 µl M9 minimal salts (for *E. coli*) or sterile-filtered, stationary-phase media (for *S. aureus*), plus a carbon source and antibiotic. Plates were incubated at 35° C., 150 r.p.m. for 4 h, then pegs were washed twice in microtiter plates with 200 µl of 1×PBS per well. To dislodge biofilm cells, pegs were placed in a microtiter plate with 145 µl of 1×PBS per well and sonicated in a water bath for 30 min at 40 kHz. Serial dilutions and spot-plating were performed to determine viable c.f.u. per peg. For determination of the dependence of *E. coli* biofilm elimination on pH, we carried out the above procedure in M9 salts buffered to an appropriate pH with citric acid, as opposed to $KH_2PO_4$, which is typically used for M9

Mouse Chronic Urinary Tract Infection Assay

Female Charles River BALB/c mice (weighing 22-26 g) received surgical implantation in the urinary tract of 6 mm PE50 catheter tubing that had been incubated in cultures of uropathogenic *E. coli* for 24 h to form biofilms 48 h after surgery, mice received either no treatment or twice-daily, intravenous treatment with gentamicin (1 mg $kg^{-1}$) or mannitol (1.5 g $kg^{-1}$) plus gentamicin (1 mg $kg^{-1}$) for 3 days. Seven or eight mice were included in each group. 24 h after the last treatment, catheter tubing was extracted to determine biofilm viability and kidneys were removed to determine bacterial load. Mouse materials were provided by ViviSource Laboratories, a facility approved by the US Department of Agriculture and by the Office of Laboratory Animal Welfare, where all in vim experimental work was performed. The study conformed with ViviSource institutional animal care and use policies and procedural guidelines.

*Staphylococcus aureus* Microarray Analysis

Raw microarray data (.CEL files) for two exponential (GSM524189, GSM524193) and two stationary phase (GSM524362, GSM524363) *S. aureus* cultures were downloaded from the Gene Expression Omnibus (GEO) series GSE20973 (Majerczyk. C. D. et al. Direct targets of CodY in *Staphylococcus aureus*. J. Bacteriol. 192, 2861-2877 (2010). Majerczyk, C. D. et al. Direct targets of CodY in *Staphylococcus aureus*. J. Bacteriol. 192, 2861-2877 (2010)"). The data were processed with RMA express using background adjustment, quantile normalization and median polish summarization to compute RMA expression values[30].

Mean expression values were calculated for both exponential and stationary-phase data and the relative fold changes (stationary/exponential) are reported in Table 3.

Software

MATLAB (Mathworks) was used for processing flow cytometric data, analysing microarray data and generating scaled heat maps using the images function. Microsoft Excel was used to plot survival assays.

TABLE 1

Enzymes inactivated to determine source of NADH generation.

| Enzyme | Gene(s) | Reducing Equivalents |
|---|---|---|
| glucose 6-phosphate-1 dehydrogenase | zwf | NADPH* |
| 6-phosphofructokinase | pfkA pfkB | NADH |

TABLE 1-continued

Enzymes inactivated to determine source of NADH generation.

| Enzyme | Gene(s) | Reducing Equivalents |
|---|---|---|
| citrate/methylcitrate synthase | gltA prpC | NADH |
| pyruvate dehydrogenase | aceE | NADH |

*NADPH can be converted to NADH by pyridine nucleotide transhydrogenase (sthA)

TABLE 2

Check primers for genetic knock-out strains.

| Gene | Forward Primer | Reverse Primer |
|---|---|---|
| mtlD | CTCCTCACGGAGAGGGTTT (SEQ ID NO: 1) | TCAAGCACACGGTTTTCAAA (SEQ ID NO: 2) |
| zwf | CGTAATCGCACGGGTGGATAA (SEQ ID NO: 3) | TTATGACTGAAACGCCTGTAACCG (SEQ ID NO: 4) |
| pfkA | CCAGGGAGGGTAAACGGTCTATG (SEQ ID NO: 5) | GGTTTCAGGGTAAAGGAATCTGCC (SEQ ID NO: 6) |
| pfkB | ATTTCTTCACTTTCCGCTGATTCG (SEQ ID NO: 7) | ATTTCCCTCATCATCCGTCATAGTG (SEQ ID NO: 8) |
| poxB | TGGTCGGGTAACGGTATCAC (SEQ ID NO: 9) | ACCGTTAGTGCCTCCTTTCTCT (SEQ ID NO: 10) |
| gltA | TAAAGCCAGGTTGATGTGCGAA (SEQ ID NO: 11) | AAGTATTGGGTTGCTGATAATTTGAGC (SEQ ID NO: 12) |
| prpC | GACCCTACAAATGATAACAATGACGAGG (SEQ ID NO: 13) | GACGATATCAACGATTTCACGATCAAA (SEQ ID NO: 14) |
| aceE | GTGAGCGTTCTCTGCGTCGTCT (SEQ ID NO: 15) | TCTCTTTCACGGTGCCAGCAA (SEQ ID NO: 16) |
| cyoA | TTCCCGTAAAATGCCCACAC (SEQ ID NO: 17) | TAATGCCAGCGATCGTAACC (SEQ ID NO: 18) |
| cydB | GCCCAAGCAGCCTGAAAA (SEQ ID NO: 19) | CGGTGATTACCCCAAACGAA (SEQ ID NO: 20) |
| appB | TGCAGAAATATGCCCGTCTG (SEQ ID NO: 21) | AGGGTGGAGAGCGAACACAT (SEQ ID NO: 22) |
| ndh | GCGAAGAACATTTTCATTGCTGTA (SEQ ID 23) | GATCGCGCTGTTCCTCAAG (SEQ ID NO: 24) |
| nuoI | TGTCCTTCGGCTGGAAAATC (SEQ ID NO: 25) | CTCGCAAGGTCGCAAGTATG (SEQ ID NO: 26) |
| kanR |  | GGTCCGCCACACCCAGCC (SEQ ID NO: 27) |

TABLE 3

Stationary phase fold regulation of metabolite transporters.

| Gene Name | UniProt Accession # | Exponential Replicate 1 | Exponential Replicate 2 | Stationary Replicate 1 | Stationary Replicate 2 | Fold change (stationary/exponential) | Description |
|---|---|---|---|---|---|---|---|
| crr | Q5HFZ9, P60856, P60857 | 100.18 | 107.50 | 120.26 | 131.12 | 1.21 | Glucose-specific phosphotransferase enzyme IIA component |
| ptsG | Q5HJI3, Q7A807, Q99X32 | 233.59 | 218.12 | 72.59 | 60.48 | 0.29 | PTS system glucose-specific EIICBA component |
| mtlA | Q5HE48, Q7A4B3, Q99SA3 | 5.59 | 4.61 | 3.21 | 3.28 | 0.64 | PTS system mannitol-specific EIICB component |
| mtlF | Q5HE46, P0A0D7, P0A0D8 | 23.64 | 16.75 | 14.62 | 23.53 | 0.94 | Mannitol-specific phosphotransferase enzyme IIA component |

TABLE 3-continued

Stationary phase fold regulation of metabolite transporters.

| Gene Name | UniProt Accession # | Exponential Replicate 1 | Exponential Replicate 2 | Stationary Replicate 1 | Stationary Replicate 2 | Fold change (stationary/ exponential) | Description |
|---|---|---|---|---|---|---|---|
| SACOL2663 | Q5HCQ6, Q7A374, Q99QZ7 | 8.93 | 8.18 | 206.91 | 150.47 | 20.88 | PTS system, fructose-specific IIABC components |

REFERENCES

Balaban, N. Q., Merrin, J., Chait, R., Kowalik, L. & Leibier, S. Bacterial persistence as a phenotypic switch. Science 305, 1622-1625 (2004).

Gefen, O., Gabay, C., Mumcuoglu, M., Engel, G. & Balaban, N. Q. Single-cell protein induction dynamics reveals a period of vulnerability to antibiotics in persister bacteria. Proc. Natl Acad. Sci. USA 105, 6145-6149 (2008).

Gefen, 0. & Balaban, N. Q. The importance of being persistent: heterogeneity of bacterial populations under antibiotic stress. FEMS Microbiol. Rev. 33, 704-717 (2009).

Lewis, K. Persister cells, dormancy and infectious disease. Nature Rev. Microbiol. 5, 48-56 (2007).

Smith, P. A. & Romesberg, F. E. Combating bacteria and drug resistance by inhibiting mechanisms of persistence and adaptation. Nature Chem. Biol. 3, 549-556 (2007).

Levin, B. R. & Rozen, D. E. Non-inherited antibiotic resistance. Nature Rev. Microbiol. 4, 556-562 (2006).

Dhar, N. & McKinney, J. D. Microbial phenotypic heterogeneity and antibiotic tolerance. Curr. Opin. Microbiol. 10, 30-38 (2007).

Shah, D. et al. Persisters: a distinct physiological state of E. coli. BMCMicrobiol. 6, 53 (2006).

Vakulenko, S. B. & Mobashery, S. Versatility of aminoglycosides and prospects for their future. Clin. Microbiol. Rev. 16, 430-450 (2003).

Magnet, S. & Blanchard, J. S. Molecular insights into aminoglycoside action and resistance. Chem. Rev. 105, 477-498 (2005).

Davis, B. D. Mechanism of bactericidal action of aminoglycosides. Microbiol. Rev. 51, 341-350 (1987).

Weisblum, B. & Davies, J. Antibiotic inhibitors of the bacterial ribosome. Bacteriol. Rev. 32, 493-528 (1968).

Kohanski, M. A., Dwyer, D. J., Wierzbowski, J., Cottarel, G. & Collins, J. J. Mistranslation of membrane proteins and two-component system activation trigger antibiotic-mediated cell death. Cell 135, 679-690 (2008).

Keren, I., Shah, D., Spoering, A., Kaldalu, N. & Lewis, K. Specialized persister cells and the mechanism of multi-drug tolerance in Escherichia coli. J. Bacteriol. 186, 8172-8180 (2004).

Spoering, A. L. & Lewis, K. Biofilms and planktonic cells of Pseudomonas aeruginosa have similar resistance to killing by antimicrobials. J. Bacteriol. 183, 6746-6751 (2001).

Taber, H. W., Mueller, J. P., Miller, P. F. & Arrow, A. S. Bacterial uptake of aminoglycoside antibiotics. Microbiol. Rev. 51, 439-457 (1987).

Bryan, L. E. & Kwan, S. Roles of ribosomal binding, membrane potential, and electron transport in bacterial uptake of streptomycin and gentamicin. Antimicrob. Agents Chemother. 23, 835-845 (1983).

Hill, S., Viollet, S., Smith, A. T. & Anthony, C. Roles for enteric d-type cytochrome oxidase in N2 fixation and microaerobiosis. J. Bacteriol. 172, 2071-2078 (1990).

Govantes, F., Albrecht, J. A. & Gunsalus, R. P. Oxygen regulation of the Escherichia coli cytochrome d oxidase (cydAB) operon: roles of multiple promoters and the Fnr-1 and Fnr-2 binding sites. Mol. Microbiol. 37, 1456-1469 (2000).

Walters, M. C. III, Roe, F., Bugnicourt, A., Franklin, M. J. & Stewart, P. S. Contributions of antibiotic penetration, oxygen limitation, and low metabolic activity to tolerance of Pseudomonas aeruginosa biofilms to ciprofloxacin and tobramycin. Antimicrob. Agents Chemother. 47, 317-323 (2003).

Mates, S. M. et al. Membrane potential and gentamicin uptake in Staphylococcus aureus. Proc. Natl Acad. Sci. USA 79, 6693-6697 (1982).

Fraimow, H. S., Greenman, J. B., Leviton, I. M., Dougherty, T. J. & Miller, M. H. Tobramycin uptake in Escherichia coli is driven byeitherelectrical potential orATP. J. Bacteriol. 173, 2800-2808 (1991).

Dwyer, D. J., Kohanski, M. A., Hayete, B. & Collins, J. J. Gyrase inhibitors induce an oxidative damage cellular death pathway in Escherichia coli. Mol. Syst. Biol. 3, 91 (2007).

Kohanski, M. A., Dwyer, D. J., Hayete, B., Lawrence, C. A. & Collins, J. J. A common mechanism of cellular death induced by bactericidal antibiotics. Cell 130, 797-810 (2007).

Keren, I., Kaldalu, N., Spoering, A., Wang, Y. & Lewis, K. Persister cells and tolerance to antimicrobials. FEMS Microbiol. Lett. 230, 13-18 (2004).

Hansen, S., Lewis, K. & Vulic, M. Role of global regulators and nucleotide metabolism in antibiotic tolerance in Escherichia coli. Antimicrob. Agents Chemother. 52, 2718-2726 (2008).

Sandoval, R., Leiser, J. & Molitoris, B. A. Aminoglycoside antibiotics traffic to the Golgi complex in LLC-PK1 cells. J. Am. Soc. Nephrol. 9, 167-174 (1998).

Lu, T. K. & Collins, J. J. Dispersing biofilms with engineered enzymatic bacteriophage. Proc. Natl Acad. Sci. USA 104, 11197-11202 (2007).

Majerczyk, C. D. et al. Direct targets of CodY in Staphylococcus aureus. J. Bacteriol. 192, 2861-2877 (2010).

Irizarry, R. A. et al. Summaries of Affymetrix GeneChip probe level data. Nucleic Acids Res. 31, e15 (2003).

Lewis, K. Persister cells, dormancy and infectious disease. Nat Rev Microbiol 5, 48-56 (2007).

Gefen, O. & Balaban, N. Q. The importance of being persistent: heterogeneity of bacterial populations under antibiotic stress. FEMS Microbiol Rev 33, 704-717 (2009).

Bigger, J. W. Treatment of staphylococcal infections with penicillin by intermittent sterilization. Lancet ii, 497-500 (1944).

Jayaraman, R. Bacterial persistence: some new insights into an old phenomenon. J Biosci 33, 795-805 (2008).

Smith, P. A. & Romesberg, F. E. Combating bacteria and drug resistance by inhibiting mechanisms of persistence and adaptation. Nat Chem Biol 3, 549-556 (2007).

Levin, B. R. & Rozen, D. E. Non-inherited antibiotic resistance. Nat Rev Microbiol 4, 556-562 (2006).

Lewis, K. Persister cells and the riddle of biofilm survival. Biochemistry (Mosc) 70, 267-274 (2005).

Kussell, E., Kishony, R., Balaban, N. Q. & Leibler, S. Bacterial persistence: a model of survival in changing environments. Genetics 169, 1807-1814 (2005).

Harrison, J. J. et al. Persister cells mediate tolerance to metal oxyanions in Escherichia coli. Microbiology 151, 3181-3195 (2005).

Keren, I., Kaldalu, N., Spoering, A., Wang, Y. & Lewis, K. Persister cells and tolerance to antimicrobials. FEMS Microbiol Lett 230, 13-18 (2004).

Moyed, H. S. & Bertrand, K. P. hipA, a newly recognized gene of Escherichia coli K-12 that affects frequency of persistence after inhibition of murein synthesis. J Bacteriol 155, 768-775 (1983).

Rotem, E. et al. Regulation of phenotypic variability by a threshold-based mechanism underlies bacterial persistence. Proc Natl Acad Sci USA 107, 12541-12546 (2010).

Korch, S. B., Henderson, T. A. & Hill, T. M. Characterization of the hipA7 allele of Escherichia coli and evidence that high persistence is governed by (p)ppGpp synthesis. Mol Microbiol 50, 1199-1213 (2003).

Spoering, A. L., Vulic, M. & Lewis, K. GlpD and PlsB participate in persister cell formation in Escherichia coli. J Bacteriol 188, 5136-5144 (2006).

McKinney, J. D. et al. Persistence of Mycobacterium tuberculosis in macrophages and mice requires the glyoxylate shunt enzyme isocitrate lyase. Nature 406, 735-738 (2000).

Dorr, T., Vulic, M. & Lewis, K. Ciprofloxacin causes persister formation by inducing the TisB toxin in Escherichia coli. PLoS Biol 8, e1000317.

Hansen, S., Lewis, K. & Vulic, M. Role of global regulators and nucleotide metabolism in antibiotic tolerance in Escherichia coli. Antimicrob Agents Chemother 52, 2718-2726 (2008).

Dorr, T., Lewis, K. & Vulic, M. SOS response induces persistence to fluoroquinolones in Escherichia coli. PLoS Genet 5, e1000760 (2009).

Balaban, N. Q., Merrin, J., Chait, R., Kowalik, L. & Leibler, S. Bacterial persistence as a phenotypic switch. Science 305, 1622-1625 (2004).

Drlica, K. & Zhao, X. DNA gyrase, topoisomerase IV, and the 4-quinolones. Microbiol Mol Biol Rev 61, 377-392 (1997).

Drlica, K. Mechanism of fluoroquinolone action. Curr Opin Microbiol 2, 504-508 (1999).

Tomasz, A. The mechanism of the irreversible antimicrobial effects of penicillins: how the beta-lactam antibiotics kill and lyse bacteria. Annu Rev Microbiol 33, 113-137 (1979).

Joers, A., Kaldalu, N. & Tenson, T. The frequency of persisters in Escherichia coli reflects the kinetics of awakening from dormancy. J Bacteriol 192, 3379-3384 (2010).

Keren, I., Shah, D., Spoering, A., Kaldalu, N. & Lewis, K. Specialized persister cells and the mechanism of multidrug tolerance in Escherichia coli. J Bacteriol 186, 8172-8180 (2004).

Shah, D. et al. Persisters: a distinct physiological state of E. coli. BMC Microbiol 6, 53 (2006).

Taber, H. W., Mueller, J. P., Miller, P. F. & Arrow, A. S. Bacterial uptake of aminoglycoside antibiotics. Microbiol Rev 51, 439-457 (1987).

Davis, B. D. Mechanism of bactericidal action of aminoglycosides. Microbiol Rev 51, 341-350 (1987).

Campbell, B. D. & Kadner, R. J. Relation of aerobiosis and ionic strength to the uptake of dihydrostreptomycin in Escherichia coli. Biochim Biophys Acta 593, 1-10 (1980).

Guest, J. R., Roberts, R. E. & Stephens, P. E. Hybrid plasmids containing the pyruvate dehydrogenase complex genes and gene-DNA relationships in the 2 to 3 minute region of the Escherichia coli chromosome. J Gen Microbiol 129, 671-680 (1983).

Costerton, J. W., Stewart, P. S. & Greenberg, E. P. Bacterial biofilms: a common cause of persistent infections. Science 284, 1318-1322 (1999).

Singh, R., Ray, P., Das, A. & Sharma, M. Penetration of antibiotics through Staphylococcus aureus and Staphylococcus epidermidis biofilms. J Antimicrob Chemother 65, 1955-1958 (2010).

Mah, T. F. & O'Toole, G. A. Mechanisms of biofilm resistance to antimicrobial agents. Trends Microbiol 9, 34-39 (2001).

Walters, M. C., 3rd, Roe, F., Bugnicourt, A., Franklin, M. J. & Stewart, P. S. Contributions of antibiotic penetration, oxygen limitation, and low metabolic activity to tolerance of Pseudomonas aeruginosa biofilms to ciprofloxacin and tobramycin. Antimicrob Agents Chemother 47, 317-323 (2003).

Lewis, K. Persister Cells. Annu Rev Microbiol 64, 357-372 (2010).

Olson, M. E., Ceri, H., Morck, D. W., Buret, A. G. & Read, R. R. Biofilm bacteria: formation and comparative susceptibility to antibiotics. Can J Vet Res 66, 86-92 (2002).

Rediske, A. M. et al. Pulsed ultrasound enhances the killing of Escherichia coli biofilms by aminoglycoside antibiotics in vivo. Antimicrob Agents Chemother 44, 771-772 (2000).

Lu, T. K. & Collins, J. J. Dispersing biofilms with engineered enzymatic bacteriophage. Proc Natl Acad Sci USA 104, 11197-11202 (2007).

Spoering, A. L. & Lewis, K. Biofilms and planktonic cells of Pseudomonas aeruginosa have similar resistance to killing by antimicrobials. J Bacteriol 183, 6746-6751 (2001).

Majerczyk, C. D. et al. Direct targets of CodY in Staphylococcus aureus. J Bacteriol 192, 2861-2877 (2010).

We claim:

1. A method for treating a chronic or persisting bacterial infection, the method comprising administering to a subject having or at risk for a chronic or persisting bacterial infection an effective amount of an aminoglycoside antibiotic and an effective amount of at least one proton motive force (PMF) stimulating compound selected from fructose and pyruvate as an adjuvant.

2. A method for treating a chronic or persisting bacterial infection, comprising: administering to a subject having a chronic or persisting bacterial infection and undergoing treatment with an aminoglycoside antibiotic, an effective amount of at least one proton motive force stimulating compound selected from mannitol, fructose and pyruvate as an adjuvant.

3. The method of claim 1, wherein the aminoglycoside antibiotic is streptomycin, gentamicin, kanamycin A, tobramycin, neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or lividomycin.

4. The method of claim 1, wherein the aminoglycoside antibiotic is gentamicin and the at least one PMF stimulating compound is fructose.

5. The method of claim 1, wherein the aminoglycoside antibiotic is tobramycin and the at least one PMF stimulating compound is pyruvate.

6. The method of claim 1, wherein the bacterial infection comprises one or more gram positive or gram negative organisms.

7. The method of claim 1, wherein the bacterial infection comprises one or more of *Escherichia coli* or *Staphylococcus aureus*.

8. The method of claim 1, wherein the bacterial infection comprises one or more of species of *Pseudomonas, Proteus, Serratia, Citrobacter, Enterobacter, Klebsiella, Pseudomonas, Acinetobacter,* or *Enterococcus*.

9. The method of claim 1, wherein the subject has a urinary tract infection; infective endocarditis; an infection of the skin, nose, ears, and/or eyes; external burns; an infection associated with cystic fibrosis; a prosthetic valve infection; a native valve infection; an infection associated with endometritis; an infection associated with febrile neutropenia; an intraabdominal infection; meningitis; an infection associated with osteomyelitis; an infection associated with pelvic inflammatory disease; an infection associated with peritonitis; an infection associated with pneumonia; an infection associated with pyelonephritis; an infection associated with skin or soft tissue; an infection associated with surgery, or an infection associated with tularemia.

10. A method of inhibiting or delaying biofilm formation or colonization on a surface of a counter, a bench top, a medical or laboratory equipment, a tool, a medical device, or an in-dwelling medical device, the method comprising contacting the surface with an effective amount of an aminoglycoside antibiotic and an effective amount one or more PMF stimulating compounds selected from fructose and pyruvate.

11. The method of claim 10, wherein the surface is the surface of an in-dwelling medical device.

12. The method of claim 1, wherein the PMF stimulating compound is mannitol or pyruvate and is administered at a concentration of at least 5 mM.

13. The method of claim 1, wherein the aminoglycoside antibiotic and PMF stimulating compound are administered topically, intraveously, intramuscularly, or via oral administration.

14. The method of claim 13, wherein the aminoglycoside antibiotic and PMF stimulating compound are administered intravenously.

15. The method of claim 14, wherein the PMF stimulating compound is administered at a concentration of at least 25 mM.

16. The method of claim 15, wherein the PMF stimulating compound is adminstered at a concentration of at least 100 mM.

17. A method for treating a chronic or persisting bacterial infection associated with an in-dwelling medical device, the method comprising administering to a subject having said infection an effective amount of an aminoglycoside antibiotic and an effective amount of at least one proton motive force (PMF) stimulating compound selected from mannitol, glucose, fructose, and pyruvate as an adjuvant.

18. The method of claim 17, wherein the aminoglycoside antibiotic is gentimicin and the PMF stimulating compound is mannitol.

19. The method of claim 17, wherein the aminoglycoside antibiotic is gentimicin and the PMF stimulating compound is pyruvate.

20. The method of claim 17, wherein the PMF stimulating compound is mannitol or pyruvate and is administered at a concentration of at least 5 mM.

21. The method of claim 17, wherein the aminoglycoside antibiotic and PMF stimulating compound are administered topically, intravenously, intramuscularly, or via oral administration.

22. The method of claim 17, wherein the aminoglycoside antibiotic and PMF stimulating compound are administered intravenously.

23. The method of claim 17, wherein the PMF stimulating compound is administered at a concentration of at least 25 mM.

24. The method of claim 17, wherein the PMF stimulating compound is adminstered at a concentration of at least 100 mM.

25. The method of claim 2, wherein the aminoglycoside antibiotic is streptomycin, gentamicin, kanamycin A, tobramycin, neomycin B, neomycin C, framycetin, paromomycin, ribostamycin, amikacin, arbekacin, bekanamycin (kanamycin B), dibekacin, spectinomycin, hygromycin B, paromomycin sulfate, netilmicin, sisomicin, isepamicin, verdamicin, astromicin, neamine, ribostamycin, or lividomycin.

26. The method of claim 2, wherein the aminoglycoside antibiotic is gentamicin and the at least one PMF stimulating compound is fructose.

27. The method of claim 2, wherein the aminoglycoside antibiotic is tobramycin and the at least one PMF stimulating compound is pyruvate.

28. The method of claim 2, wherein the bacterial infection comprises one or more gram positive or gram negative organisms.

29. The method of claim 2, wherein the bacterial infection comprises one or more of *Escherichia coli* or *Staphylococcus aureus*.

30. The method of claim 2, wherein the bacterial infection comprises one or more of species of *Pseudomonas, Proteus, Serratia, Citrobacter, Enterobacter, Klebsiella, Acinetobacter,* or *Enterococcus*.

31. The method of claim 2, wherein the subject has a urinary tract infection; infective endocarditis; an infection of the skin, nose, ears, and/or eyes; external burns; an infection associated with cystic fibrosis; a prosthetic valve infection; a native valve infection; an infection associated with endometritis; an infection associated with febrile neutropenia; an intraabdominal infection; meningitis; an infection associated with osteomyelitis; an infection associated with pelvic inflammatory disease; an infection associated with peritonitis; an infection associated with pneumonia; an infection associated with pyelonephritis; an infection associated with skin or soft tissue; an infection associated with surgery, or an infection associated with tularemia.

32. The method of claim 2, wherein the infection is associated with Cystic fibrosis.

33. The method of claim 2, wherein the infection is a urinary tract infection.

34. The method of claim 2, wherein the infection is associated with an in-dwelling medical device.

35. The method of claim 2, wherein the infection is a hospital-acquired infection.

36. The method of claim 2, wherein the aminoglycoside antibiotic is gentimicin and the PMF stimulating compound is mannitol.

37. The method of claim 2, wherein the aminoglycoside antibiotic is gentimicin and the PMF stimulating compound is pyruvate.

38. The method of claim 2, wherein the PMF stimulating compound is mannitol or pyruvate and is administered at a concentration of at least 5 mM.

39. The method of claim 2, wherein the aminoglycoside antibiotic and PMF stimulating compound are administered topically, intravenously, intramuscularly, or via oral administration.

40. The method of claim 2, wherein the aminoglycoside antibiotic and PMF stimulating compound are administered intravenously.

41. The method of claim 2, wherein the PMF stimulating compound is administered at a concentration of at least 25 mM.

42. The method of claim 2, wherein the PMF stimulating compound is adminstered at a concentration of at least 100 mM.

43. The method of claim 2, wherein the aminoglycoside and the PMF stimulating compound are co-formulated or administered simultaneously.

44. The method of claim 2, wherein the aminoglycoside and PMF stimulating compound are in a single formulation and administered by the inhalation route.

45. The method of claim 1, wherein the aminoglycoside and PMF stimulating compound are in a single formulation and administered by the inhalation route.

46. The method of claim 1, wherein the patient has chronic obstructive pulmonary disease (COPD).

47. The method of claim 1, wherein the patient has bronchiectasis.

48. The method of claim 1, wherein the patient has a mycobacterial infection, wherein the infection is not tuberculosis.

* * * * *

SEQUENCE LISTING

<160> NUMBER OF SEQ ID NOS: 27

<210> SEQ ID NO 1
<211> LENGTH: 19
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
ctcctcacgg agagggttt                                                      19

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
tcaagcacac ggttttcaaa                                                     20

<210> SEQ ID NO 3
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
cgtaatcgca cgggtggata a                                                   21

<210> SEQ ID NO 4
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ttatgactga aacgcctgta accg                                                24

<210> SEQ ID NO 5
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ccagggaggg taaacggtct atg                                                 23

<210> SEQ ID NO 6
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 6
ggtttcaggg taaaggaatc tgcc                                                24
```

<210> SEQ ID NO 7
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
atttcttcac tttccgctga ttcg                                          24

<210> SEQ ID NO 8
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
atttccctca tcatccgtca tagtg                                         25

<210> SEQ ID NO 9
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
tggtcgggta acggtatcac                                               20

<210> SEQ ID NO 10
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
accgttagtg cctcctttct ct                                            22

<210> SEQ ID NO 11
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
taaagccagg ttgatgtgcg aa                                            22

<210> SEQ ID NO 12
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 12
aagtattggg ttgctgataa tttgagc                                           27

<210> SEQ ID NO 13
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13
gaccctacaa atgataacaa tgacgagg                                          28

<210> SEQ ID NO 14
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14
gacgatatca acgatttcac gatcaaa                                           27

<210> SEQ ID NO 15
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
gtgagcgttc tctgcgtcgt ct                                                22

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
tctctttcac ggtgccagca a                                                 21

<210> SEQ ID NO 17
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ttcccgtaaa atgcccacac                                                   20

<210> SEQ ID NO 18
<211> LENGTH: 20

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
taatgccagc gatcgtaacc                                                  20

<210> SEQ ID NO 19
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
gcccaagcag cctgaaaa                                                    18

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
cggtgattac cccaaacgaa                                                  20

<210> SEQ ID NO 21
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
tgcagaaata tgcccgtctg                                                  20

<210> SEQ ID NO 22
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
agggtggaga gcgaacacat                                                  20

<210> SEQ ID NO 23
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
```

```
gcgaagaaca ttttcattgc tgta                                                    24

<210> SEQ ID NO 24
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gatcgcgctg ttcctcaag                                                          19

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
tgtccttcgg ctggaaaatc                                                         20

<210> SEQ ID NO 26
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
ctcgcaaggt cgcaagtatg                                                         20

<210> SEQ ID NO 27
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
ggtccgccac acccagcc                                                           18
```